US011845759B2

(12) United States Patent
Chang et al.

(10) Patent No.: US 11,845,759 B2
(45) Date of Patent: Dec. 19, 2023

(54) OPIOID COMPOUNDS AND USES THEREOF

(71) Applicant: RHODES TECHNOLOGIES, Coventry, RI (US)

(72) Inventors: Ping Chang, Waterford, CT (US); Raymond Glowaky, Killingworth, CT (US); Michael David Rogers, Maryland Heights, MO (US)

(73) Assignee: RHODES TECHNOLOGIES, Coventry, RI (US)

( * ) Notice: Subject to any disclaimer, the term of this patent is extended or adjusted under 35 U.S.C. 154(b) by 0 days.

(21) Appl. No.: 16/971,733

(22) PCT Filed: Feb. 22, 2019

(86) PCT No.: PCT/US2019/019280
§ 371 (c)(1),
(2) Date: Aug. 21, 2020

(87) PCT Pub. No.: WO2019/165298
PCT Pub. Date: Aug. 29, 2019

(65) Prior Publication Data
US 2021/0061815 A1 Mar. 4, 2021

Related U.S. Application Data

(60) Provisional application No. 62/634,507, filed on Feb. 23, 2018.

(51) Int. Cl.
*C07D 489/08* (2006.01)
*A61K 31/485* (2006.01)
*A61P 25/36* (2006.01)
*A61K 9/00* (2006.01)

(52) U.S. Cl.
CPC .......... *C07D 489/08* (2013.01); *A61K 9/0053* (2013.01); *A61P 25/36* (2018.01)

(58) Field of Classification Search
CPC ...... C07D 489/08; A61K 31/485; A61P 25/04
USPC ............................................ 546/44; 514/282
See application file for complete search history.

(56) References Cited

U.S. PATENT DOCUMENTS

| | | | | |
|---|---|---|---|---|
| 1,731,152 | A | 10/1929 | Schopf | |
| 2,203,121 | A | 6/1940 | Philipp et al. | |
| 3,828,050 | A | 8/1974 | Buckett et al. | |
| 4,100,288 | A | 7/1978 | Merz et al. | |
| 4,140,755 | A | 2/1979 | Sheth et al. | |
| 4,141,897 | A | 2/1979 | Olofson et al. | |
| 4,167,558 | A | 9/1979 | Sheth et al. | |
| 4,322,426 | A | 3/1982 | Hermann et al. | |
| 5,169,638 | A | 12/1992 | Dennis et al. | |
| 5,232,704 | A | 8/1993 | Franz et al. | |
| 5,672,360 | A | 9/1997 | Sackler et al. | |
| 5,952,495 | A | 9/1999 | Huang et al. | |
| 5,968,551 | A | 10/1999 | Oshlack et al. | |
| 6,090,411 | A | 7/2000 | Pillay et al. | |
| 6,294,195 | B1 | 9/2001 | Oshlack et al. | |
| 6,635,279 | B2 | 10/2003 | Kolter et al. | |
| 7,157,100 | B2 | 1/2007 | Doshi et al. | |
| 7,230,005 | B2 | 6/2007 | Shafer et al. | |
| 7,270,831 | B2 | 9/2007 | Oshlack et al. | |
| 7,514,100 | B2 | 4/2009 | Oshlack et al. | |
| 7,838,028 | B2 | 11/2010 | Grenier et al. | |
| 9,125,947 | B2 * | 9/2015 | Mickle | A61P 25/04 |
| 9,139,612 | B2 * | 9/2015 | Jenkins | A61P 25/36 |
| 9,562,014 | B2 * | 2/2017 | Trawick | A61P 29/00 |
| 9,682,076 | B2 * | 6/2017 | Mickle | A61P 25/30 |
| 10,017,519 | B2 * | 7/2018 | Thottathil | A61P 25/36 |
| 10,988,480 | B2 | 4/2021 | Kupper et al. | |
| 2004/0033253 | A1 | 2/2004 | Shevchuk et al. | |
| 2004/0204434 | A1 | 10/2004 | Shafer et al. | |

(Continued)

FOREIGN PATENT DOCUMENTS

| | | | |
|---|---|---|---|
| CN | 1204649 | A | 1/1999 |
| CN | 102573845 | A | 7/2012 |

(Continued)

OTHER PUBLICATIONS

Nagase, H. et al.: Facile intramolecular O-14 - C7 acetyl transfer in opiate 14-acetate esters. J. Org. Chem., vol. 55, pp. 365-367, 1990.*
Bartho, L., et al., “Involvement of Capsaicin-sensitive Neurones in Hyperalgesia and Enhanced Opioid Antinociception in Inflammation,” Naunyn-Schmiedeberg’s Archives of Pharmacology 342(6):666-670, Springer Verlag, Germany (1990).
Bingham, A.L., et al., “Over One Hundred Solvates of Sulfathiazole,” Chemical Communications 7:603-604, Royal Society of Chemistry, United States (2001).

(Continued)

*Primary Examiner* — Charanjit Aulakh
(74) *Attorney, Agent, or Firm* — STERNE, KESSLER, GOLDSTEIN & FOX, P.L.L.C.

(57) ABSTRACT

This invention relates to novel opioid derivatives of Formula I: or a pharmaceutically acceptable salt or solvate thereof, wherein $R^1$, $R^3$, $R^4$ and Z are as defined herein in the disclosure. The invention also relates to the use of such compounds for the treatment or prevention of, for example, pain.

Formula I

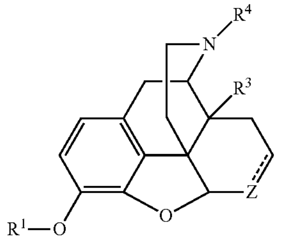

26 Claims, 19 Drawing Sheets

(56) References Cited

U.S. PATENT DOCUMENTS

| | | | |
|---|---|---|---|
| 2005/0080012 A1 | 4/2005 | Mickle et al. |
| 2006/0013876 A1 | 1/2006 | Lohray et al. |
| 2006/0167258 A1 | 7/2006 | Likhotvorik et al. |
| 2008/0312411 A1 | 12/2008 | Wolf et al. |
| 2008/0318905 A1 | 12/2008 | Muhammad et al. |
| 2009/0192095 A1 | 7/2009 | Franklin et al. |
| 2009/0253792 A1 | 10/2009 | Mickle et al. |
| 2010/0286186 A1 | 11/2010 | Franklin et al. |
| 2011/0002990 A1 | 1/2011 | Mickle et al. |
| 2011/0306628 A1 | 12/2011 | Zhang et al. |
| 2011/0313163 A1 | 12/2011 | Hudlicky et al. |
| 2012/0283444 A1 | 11/2012 | Hudlicky et al. |
| 2013/0023553 A1 | 1/2013 | Jude-Fishburn et al. |
| 2015/0050339 A1 | 2/2015 | Mickle et al. |
| 2016/0304529 A1 | 10/2016 | Lewis et al. |
| 2016/0326182 A1 | 11/2016 | Peltier et al. |
| 2017/0015266 A1 | 1/2017 | El-Jawahri et al. |
| 2017/0095734 A1 | 4/2017 | O'Donnell, Sr. |
| 2017/0151228 A1 | 6/2017 | Thottathil |
| 2017/0152266 A1 | 6/2017 | Thottathil |
| 2017/0196851 A1 | 7/2017 | Thottathil |

FOREIGN PATENT DOCUMENTS

| | | | |
|---|---|---|---|
| CN | 105246897 | A | 1/2016 |
| FR | 2657350 | A1 | 7/1991 |
| GB | 2000137 | A | 1/1979 |
| JP | S5231100 | A | 3/1977 |
| JP | S549300 | A | 1/1979 |
| JP | 2006502967 | A | 1/2006 |
| JP | 2006052309 | A | 2/2006 |
| JP | 2006520392 | A | 9/2006 |
| JP | 2012532142 | A | 12/2012 |
| JP | 2012533561 | A | 12/2012 |
| JP | 2014514339 | A | 6/2014 |
| JP | 2017535593 | A | 11/2017 |
| JP | 2017538696 | A | 12/2017 |
| RU | 2215741 | C1 | 11/2003 |
| RU | 2221566 | C1 | 1/2004 |
| WO | WO-9802033 | A1 | 1/1998 |
| WO | WO-03084520 | A2 | 10/2003 |
| WO | WO-2004082620 | A2 | 9/2004 |
| WO | WO-2006035195 | A1 | 4/2006 |
| WO | WO-2010083384 | A2 | 7/2010 |
| WO | WO-2011002991 | A1 | 1/2011 |
| WO | WO-2011002995 | A1 | 1/2011 |
| WO | WO-2011009015 | A1 | 1/2011 |
| WO | WO-2011088140 | A1 | 7/2011 |
| WO | WO-2012008984 | A1 | 1/2012 |
| WO | WO-2012151669 | A1 | 11/2012 |
| WO | WO-2014138740 | A1 | 9/2014 |
| WO | WO-2015082932 | A1 | 6/2015 |
| WO | WO-2016086113 | A1 | 6/2016 |
| WO | WO-2016089951 | A1 | 6/2016 |

OTHER PUBLICATIONS

Caira, M,R., et al., "Preparation and Crystal Characterization of a Polymorph, a Monohydrate, and an Ethyl Acetate Solvate of the Antifungal Fluconazole," Journal of Pharmaceutical Sciences 93(3):601-611, Wiley-Liss, Inc. and American Pharmacists Assn., United States (2004).

D'Amour, F.E. and Smith, D.L., "A Method for Determining Loss of Pain Sensation," Journal of Pharmacology and Experimental Therapeutics 72(1):74-79, The American Society of Pharmacology and Experimental Therapeutics, United States (1941).

Filer, C.N., "Chapter 6: The Preparation and Characterization of Tritiated Neurochemicals," in Isotopes in the Physical and Biomedical Sciences, vol. 1, Labelled Compounds (Part A), Buncel, E. and Jones, J.R. eds., pp. 156-192, Elsevier Science Publishers B.V. (1987).

Foss, J.F., "A Review of the Potential Role of Methylnaltrexone in Opioid Bowel Dysfunction," American Journal of Surgery 182(5A Suppl):19S-26S, Excerpta Medica, United States (2001).

Goodson, Max, "Chapter 6. Dental Applications" in *Medical Applications of Controlled Release*, vol. 2, Langer; R.S and Wise; D.L. eds. pp. 115-138, CRC Press, United States (1984).

Grupp, I.L., et al., "Protection Against Hypoxia-reoxygenation in the Absence of Poly (ADP-ribose) Synthetase in Isolated Working Hearts," Journal of Molecular and Cellular Cardiology 31(1):297-303, Academic Press, England (1999).

Hanson G.R., "Chapter 72. Analgesic, Antipyretic and Anti-Inflammatory Drugs" in Remington: The Science and Practice of Pharmacy, vol. II, Gennaro A.R., ed., 19th Edition, pp. 1196-1221, Mack Printing Company, United States (1995).

Hargreaves, K., et al., "A New and Sensitive Method for Measuring Thermal Nociception in Cutaneous Hyperalgesia," Pain 32(1):77-88, Lippincott Williams & Wilkins, United States (1988).

Hunskaar, S., et al., "Formalin Test in Mice, a Useful Technique for Evaluating Mild Analgesics," Journal of Neuroscience Methods 14(1):69-76, Elsevier/North-Holland Biomedical Press, Netherlands (1985).

Insel, P.A., "Analgesic-Antipyretic and Antiinflammatory Agents and Drugs Employed in the Treatment of Gout," in Goodman & Gilman's the Pharmacological Basis of Therapeutics, 9th Edition, Molinoff, P.B. and Ruddon, R.W., eds., pp. 617-657, McGraw Hill, United States (1996).

International Search Report and Written Opinion for International Application No. PCT/US2019/019280, European Patent Office, Netherlands, dated Jul. 15, 2019.

Kim, S.H., et al., "An Experimental Model for Peripheral Neuropathy Produced by Segmental Spinal Nerve Ligation in the Rat," Pain 50(3):355-363, Lippincott Williams & Wilkins, United States (1992).

Langer, R., "New methods of drug delivery," Science 249(4976):1527-1533, American Association of the Advancement of Science, United States (1990).

Radebaugh, G.W. et al., Chapters 83-89 in Remington's Pharmaceutical Sciences, Alfonso R. Gennaro ed., 19th Edition, pp. 1447-1676, Mack Printing Company, United States (1995).

Ross and Kenakin, "Chapter 2: Pharmacodynamics: Mechanisms of Drug Action and the Relationship Between Drug Concentration and Effect," in Goodman & Gilman's the Pharmacological Basis of Therapeutics, 10th Ed., J.G. Hardman, L.E. Limbird and A. Goodman-Gilman eds., pp. 31-43, McGraw-Hill Publishing, United States (2001).

Seltzer, Z., et al., "A Novel Behavioral Model of Neuropathic Pain Disorders Produced in Rats by Partial Sciatic Nerve Injury," Pain 43(2):205-218, Lippincott Williams & Wilkins, United States (1990).

Sharma, N., et al., "A Comprehensive Review on Floating Drug Delivery System," International Journal of Research in Pharmaceutical and Biomedical Sciences 2(2):428-441, JK Welfare & Pharmascope Foundation, India (2011).

Stein, C., et al., "Unilateral Inflammation of the Hindpaw in Rats as a Model of Prolonged Noxious Stimulation: Alterations in Behavior and Nociceptive Thresholds," Pharmacology, Biochemistry, and Behavior 31(2):445-455, Elsevier, United States (1988).

Torbati, D., et al., "Effect of Hypothermia on Ventilation in Anesthetized, Spontaneously Breathing Rats: Theoretical Implications for Mechanical Ventilation," Intensive Care Medicine 26(5):585-591, Springer-Verlag GmbH & Co., Germany (2000).

Van Tonder, E.C., et al., "Preparation and Physicochemical Characterization of 5 Niclosamide Solvates and 1 Hemisolvate," AAPS PharmSciTech 5(1):E12, American Association of Pharmaceutical Scientists, United States (2004), 10 pages.

Woolfe, G. and Macdonald, A.D., "The Evaluation of the Analgesic Action of Pethidine Hydrochloride (Demerol)," Journal of Pharmacology and Experimental Therapeutics 80(3):300-307, The American Society of Pharmacology and Experimental Therapeutics, United States (1944).

Wuts, P.G.M. and Greene, T.W., "Protection for Phenols and Catechols," in Greene's Protective Groups in Organic Synthesis, 4th Ed., Wuts, P.G.M. and Greene, T.W., eds., pp. 367-430, John Wiley & Sons, Inc., United States (2007).

Wuts, P.G.M. and Greene, T.W., "Protection for the Hydroxyl Group, Including 1,2- and 1,3-Diols," in Greene's Protective Groups in Organic Synthesis, 4th Ed., Wuts, P.G.M. and Greene, T.W., eds., pp. 16-366, John Wiley & Sons, Inc., United States (2007).

(56) References Cited

OTHER PUBLICATIONS

Maurer, H., and K. Pfleger, "Screening procedure for the detection of opioids, other potent analgesics and their metabolites in urine using a computerized gas chromatographic-mass spectrometric technique," Fresenius' Zeitschrift für Analytische Chemie 317(1): 42-52, Springer Publishing, United States (1984).
Von Kelentey, B., et al., "Darstellung und Pharmakologisches Verhalten von Morphinderivaten (I)" [Preparation & pharmacological action of morphine derivatives (I)], Die Pharmazie. 12(9):600-607, Germany (1957).
Hosztafi, S., et al. "Synthesis and analgetic activity of nicotinic esters of morphine derivatives," Arzneimittel-Forschung/Drug Res. 43(11): 1200-1203, Thieme Medical Publishers, Germany (1993).
Small, Lyndon, et al., "The Addition of Organomagnesium Halides to Pseudocodeine Types. II. Preparation of Nuclear Alkylated Morphine Derivatives," Journal of the American Chemical Society 58(8): 1457-1463, American Chemical Society, United States (1936).
Sumwalt, M. et al., "The Respiratory Effects of Morphine, Codeine, and Related Substances X. The Effect of Substituting an Additional Group in Ring-Three." Journal of Pharmacology and Experimental Therapeutics 73(3):258-273, The American Society for Pharmacology and Experimental Therapeutics, United States (1941).
Aceto, M. D., et al., "Dependence Studies of New Compounds in the Rhesus Monkey, Rat and Mouse (2002)," NIDA Res. Monogr. 183:191-227, National Institute on Drug Abuse, United States (2003).
Beni, S., et al., "Preparation of benzoate esters of morphine and its derivatives," Monatshefte fur Chemie—Chemical Monthly 143(10):1431-1440, Springer-Verlag Wien, Austria (2012).
Kreutzberger, C. B., et al., "Vinyl Chloroformate," in *Encyclopedia of Reagents for Organic Synthesis* (*e-EROS*), 3 pages, John Wiley & Sons, Ltd., United States (2001).
STN Database: CAS Registry (STN), CAS Registry No. 792844-31-6 (entered Dec. 6, 2004), STN International, Columbus, OH, accessed Sep. 7, 2021.
STN Database: CAS Registry (STN) CAS Registry No. 790596-36-0 (entered Nov. 29, 2004), STN International, Columbus, OH, assessed Sep. 7, 2021.
STN Database: CAS Registry (STN) CAS Registry No. 759395-35-2 (entered Oct. 8, 2004), STN International, Columbus, OH, assessed Sep. 7, 2021.
STN Database: CAS Registry (STN) CAS Registry No. 747380-46-7 (entered Sep. 17, 2004), STN International, Columbus, OH, assessed Sep. 7, 2021.
STN Database: CAS Registry (STN) CAS Registry No. 740740-41-4 (entered Sep. 6, 2004), STN International, Columbus, OH, assessed Sep. 7, 2021.
STN Database: CAS Registry (STN) CAS Registry No. 30964-43-3 (entered Nov. 16, 1984), STN International, Columbus, OH, assessed Sep. 7, 2021.
STN Database: CAS Registry (STN) CAS Registry No. 30964-42-2 (entered Nov. 16, 1984), STN International, Columbus, OH, assessed Sep. 7, 2021.
STN Database: CAS Registry (STN) CAS Registry No. 30964-38-6 (entered Nov. 16, 1984), STN International, Columbus, OH, assessed Sep. 7, 2021.
STN Database: CAS Registry (STN) CAS Registry No. 30964-34-2 (entered Nov. 16, 1984), STN International, Columbus, OH, assessed Sep. 7, 2021.
STN Database: CAS Registry (STN) CAS Registry No. 30964-32-0 (entered Nov. 16, 1984), STN International, Columbus, OH, assessed Sep. 7, 2021.
STN Database: CAS Registry (STN) CAS Registry No. 30964-30-8 (entered Nov. 16, 1984), STN International, Columbus, OH, assessed Sep. 7, 2021.
STN Database: CAS Registry (STN) CAS Registry No. 30964-28-4 (entered Nov. 16, 1984), STN International, Columbus, OH, assessed Sep. 7, 2021.
STN Database: CAS Registry (STN) CAS Registry No. 76-42-6 (entered Nov. 16, 1984), STN International, Columbus, Ohio, United States.
Nagase, H., et al., "Facile Intramolecular O-14 > C-7 Acetyl Transfer in Opiate 14-Acetate Esters," J. Org. Chem. 55(1):365-367, American Chemical Society, United States (1990).
Wang, Y., et al., "Requirements by FDA for research on abuse deterrence of opioids," Drugs & Clinic 29(11):1311-1317, Springer-Verlag, Germany (2012).
STN Database: CAS Registry (STN) CAS Registry No. 125-29-1 (entered Nov. 16, 1984) STN International, Columbus, Ohio, United States.
Nagase, H., et al., "The facility of formation of a Δ6 bond in dihydromorphinone and related opiates," J Org Chem 54(17):4120-4125, American Chemical Society, United States (Aug. 1989).
Database CAPLUS on STN, Chemical Abstracts Accession No. 1961:43372 English language abstract, Seki, I., "14-Hydroxydihydronormorphinone," Takamine Kenkyusho Nenpo 12:56-62, Sankyo Shinagawa Factory, Tokyo, Japan (1960).

* cited by examiner

1H NMR 04822 1498-62.esp

PROTON_01.esp

PROTON_01.esp

OPIOID COMPOUNDS AND USES THEREOF

BACKGROUND OF THE INVENTION

Field of the Invention

This invention is in the field of medicinal chemistry. In particular, the invention relates to novel opioid compounds.

Related Art

The primary location of pain control is in the central nervous system (CNS). The three primary classes of opioid receptors, μ (mu), κ (kappa), and δ (delta), are distributed throughout the CNS and the periphery (Foss, J. F., *The American Journal of Surgery* 182 (*Suppl. to November* 2001): 19S-26S (2001)). The principal receptor involved in pain management is the μ opioid receptor (Foss, J. F., ibid).

Opioids, also known as opioid agonists, are a group of compounds that bind to the above mentioned opioid receptors, and exhibit opium or morphine-like properties. The opioids are widely administered for a variety of medical indications but primarily they are employed as moderate to strong analgesics. Examples of opioid compounds include, but are not limited to, morphine, oxycodone, hydromorphone, oxymorphone, hydrocodone, levophanol, methadone, meperidine, fentanyl, codeine, propoxyphene, buprenorphine, butorphanol, pentazocine and nalbuphine.

The use of opioid compounds has been reported to have a number of potential side effects, including abuse and diversion.

There have been attempts to reduce the abuse potential of opioids. For example, various opioid receptor antagonists have been developed to block the action of opioid agonists when an overdose occurs. Also, in an attempt to formulate abuse-resistant tablets, various formulations have been developed containing an opioid receptor agonist combined with the opioid antagonist, wherein the antagonist becomes substantially bioavailable upon crushing or tampering with the tablets.

Other alternatives to reduce the abuse potential of opioids include the use of opioid prodrugs. Opioid prodrugs can exhibit different pharmacological properties than opioids, such as those relating to absorption, distribution, and elimination. For example, U.S. Pat. No. 7,230,005 describes converting an opiate analgesic agent to its poorly absorbed ester prodrug or other prodrug derivatives; U.S. Patent Appl. Publication No. 2008/0318905 describes covalently attaching a prodrug moiety to the amine functional group of an abuse-prone parent drug; U.S. Patent Appl. Publication No. 2009/0192095 describes opioid prodrugs comprising an opioid analgesic covalently bonded through a carbamate linkage to a peptide of 1-5 amino acids in length; WO 2011/002991 A1 describes hydrocodone enol-ester conjugates as prodrugs; U.S. Patent Application Publication No. 2017/095734 describes hydrocodone and hydromorphone prodrugs; U.S. Patent Application Publication No. 2017/015266 describes oxycodone prodrugs; and U.S. Patent Application Publication No. 2017/0151228 describes oxymorphone prodrugs.

There remains a need to provide opioid prodrugs, when administered to a patient identified in need thereof, that provide effective analgesia while reducing the potential for abuse or adverse side effects.

SUMMARY OF THE INVENTION

In one aspect, the present disclosure provides compounds represented by Formulae I, II, III, IV, V, and VI, below, and pharmaceutically acceptable salts and solvates thereof, collectively referred to herein as "Compounds of the Disclosure" (each is individually referred to hereinafter as a "Compound of the Disclosure").

In another aspect, the present disclosure provides the use of Compounds of the Disclosure as modulators of one or more opioid receptors. Specifically, the present disclosure provides the use of Compounds of the Disclosure as modulators of μ, δ, κ, and/or ORL-1 opioid receptors, and especially modulators of μ opioid receptors.

In another aspect, the present disclosure provides a method of treating, ameliorating, or preventing a disorder responsive to the modulation of one or more opioid receptors in a patient, comprising administering to the patient an effective amount of a Compound of the Disclosure.

In another aspect, the present disclosure provides use of a Compound of the Disclosure as an analgesic to treat, ameliorate, or prevent pain.

The present invention further provides a method of treating, ameliorating, or preventing pain, comprising administering to a patient in need thereof a therapeutically effective amount of a Compound of the Disclosure. In certain embodiments, the pain is acute pain, chronic pain (which includes but is not limited to, neuropathic pain, postoperative pain, and inflammatory pain), and surgical pain. In a certain embodiment, the Compounds of the Disclosure are useful for treating or preventing chronic pain. In a particular embodiment, the administration is by the oral route. In one embodiment, the compound is formulated in a solid oral dosage form. In another embodiment, the compound is formulated in a liquid oral dosage form. In one embodiment, the dosage form is designed for immediate release. In another embodiment, the dosage form is designed for controlled release.

In another aspect, the present disclosure provides a pharmaceutical composition comprising a Compound of the Disclosure and one or more pharmaceutically acceptable carriers. Such compositions are useful for treating, ameliorating, or preventing pain in a patient. In a particular embodiment, the pharmaceutical composition is an oral dosage form. In one embodiment, the pharmaceutical composition is a solid oral dosage form. In another embodiment, the pharmaceutical composition is a liquid oral dosage form. In one embodiment, the dosage form is designed for immediate release. In another embodiment, the dosage form is designed for controlled release.

In another embodiment, the present invention is directed to methods of treating, ameliorating or preventing pain, comprising administering a pharmaceutical composition of the invention to a patient in need of said treatment, amelioration or prevention. In a particular embodiment, the administration is by the oral route. In one embodiment, the compound is in a solid oral dosage form. In another embodiment, the compound is in a liquid oral dosage form. In one embodiment, the dosage form is designed for immediate release. In another embodiment, the dosage form is designed for controlled release.

In another aspect, the present disclosure provides Compounds of the Disclosure for use in treatment, amelioration, or prevention of a disorder responsive to the modulation of one or more opioid receptors. Preferably, the disorder is responsive to modulation of the μ-opioid receptor.

In another aspect, the present disclosure provides a method of modulating one or more opioid receptors in a patient in need of said modulation, comprising administering to the patient an effective amount of a Compound of the Disclosure.

In another aspect, the present disclosure provides Compounds of the Disclosure for use in treatment, amelioration, or prevention of pain in a patient in need of said treatment, amelioration, or prevention.

In another aspect, the present disclosure provides Compounds of the Disclosure for use in treatment, amelioration, or prevention of pain in a patient, such as acute pain, chronic pain (which includes but is not limited to, neuropathic pain, postoperative pain, and inflammatory pain), or surgical pain.

In another aspect, the present disclosure provides use of Compounds of the Disclosure in the manufacture of a medicament for treating, ameliorating, or preventing a disorder responsive to the modulation of one or more opioid receptors.

In another aspect, the present disclosure provides use of Compounds of the Disclosure in the manufacture of a medicament for modulating of one or more opioid receptors in a patient. Preferably, the μ- or κ-opioid receptor is modulated.

In another aspect, the present disclosure provides Compounds of the Disclosure for use as a medicament.

In another aspect, the present disclosure provides use of a Compound of the Disclosure in the manufacture of a medicament for treating, ameliorating, or preventing pain in a patient, such as acute pain, chronic pain, or surgical pain.

In another aspect, the present disclosure provides a pharmaceutical composition, comprising a Compound of the Disclosure for treating, ameliorating, or preventing a disorder responsive to the modulation of one or more opioid receptors.

The present disclosure further provides methods for preparing a pharmaceutical composition, comprising admixing a Compound of the Disclosure and a pharmaceutically acceptable carrier to form the pharmaceutical composition.

In a further aspect, the invention relates to a kit, comprising a sterile container containing an effective amount of a Compound of the Disclosure and instructions for therapeutic use.

In a further aspect, the present disclosure further provides a method of slowing the onset of activity of an opioid in a mammal in need of opioid therapy, comprising orally administering to the mammal a therapeutically effective amount of a Compound of the Disclosure or a mixture of Compounds of the Disclosure. In one embodiment of this aspect of the disclosure, the Compound of the Disclosure is co-administered with one or more other therapeutic agents. In another embodiment, the method provides slowing the onset of analgesic activity of the opioid.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF THE DRAWINGS

The following drawings are given by way of illustration only, and thus are not intended to limit the scope of the present invention.

DETAILED DESCRIPTION OF THE INVENTION

Figure 1A:
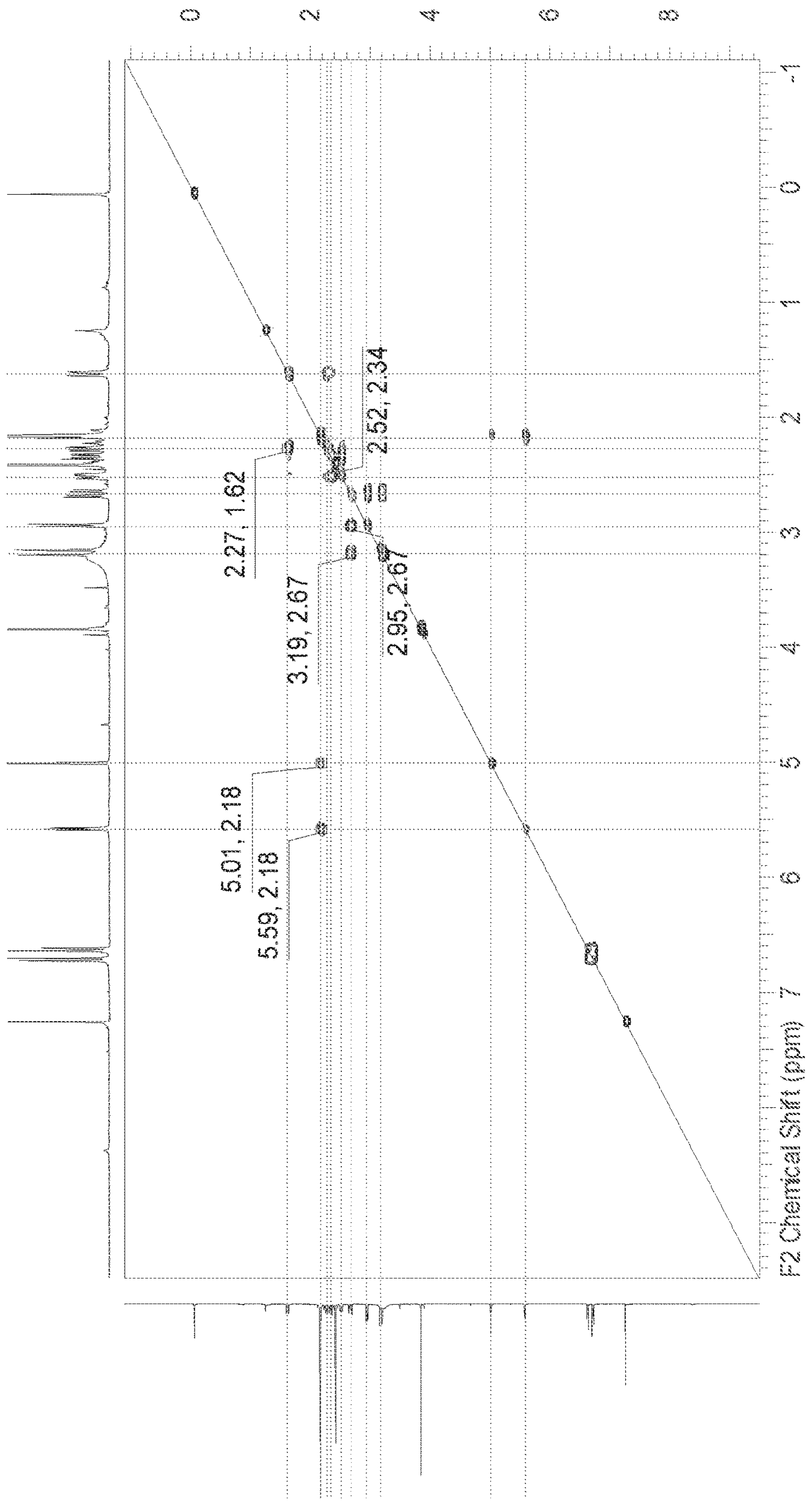
FIGS. 1A, 1B, 1C, and 1D depict the COSY NMR spectrum, a partial $^1$H NMR spectrum, the $^1$H NMR spectrum, and the HPLC chromatogram, respectively, for 6-acetyl oxycodone prepared in Example 1.

One aspect of the present invention provides Compounds of the Disclosure represented by Formula I:

I

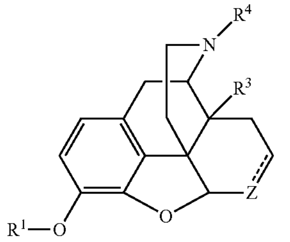

and pharmaceutically acceptable salts and solvates thereof, wherein:

$R^1$ is H; alkyl optionally substituted with 1, 2, or 3 substituents, each independently selected from the group consisting of hydroxy, halo, haloalkyl, amino, alkylamino, dialkylamino, carboxy, alkoxy, and alkoxycarbonyl; -PEG-$R^7$; or a hydroxyl protecting group PG selected from the group consisting of alkyl, arylalkyl, heterocyclo, (heterocyclo)alkyl, acyl, silyl, and carbonate, any of which is optionally substituted;

Z is C—$OR^2$ or C(═O);

 is single bond or a double bond, provided that  is a single bond when Z is C(═O) and  is a double bond when Z is C—$OR^2$;

$R^2$ is —C(═O)$R^5$ or -PEG-$R^7$, wherein $R^5$ is selected from the group consisting of unsubstituted $C_{1-12}$ alkyl, unsubstituted $C_{2-12}$ alkenyl, unsubstituted $C_{2-12}$ alkynyl, —$CH_2$—O—$(CH_2CH_2O)_m$—$R^7$, —O—$(CH_2CH_2O)_n$—$R^7$, —NH—$(CH_2CH_2O)_p$—$R^7$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; and wherein the 6-membered heterocycle group is attached to the carbonyl carbon of $R^2$ through a carbon atom or through a nitrogen atom;

$R^3$ is hydrogen, OH, —Y-PEG-$R^7$, or —OC(═O)$R^6$, wherein

Y is a covalent bond or a linker;

$R^6$ is selected from the group consisting of unsubstituted $C_{1-12}$ alkyl, unsubstituted $C_{2-12}$ alkenyl, unsubstituted $C_{2-12}$ alkynyl, —$CH_2$—O—$(CH_2CH_2O)_m$—$R^7$, —O—$(CH_2CH_2O)_n$—$R^7$, —NH$(CH_2CH_2O)_p$—$R^7$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; and wherein the 6-membered heterocycle group is attached to the carbonyl carbon through a carbon atom or through a nitrogen atom;

provided that $R^3$ is —OC(═O)$R^6$ when Z is C(═O);

$R^7$ is selected form the group consisting of hydrogen, $C_{1-6}$ alkyl, aryl, heteroaryl, cycloalkyl, and heterocyclo, any of which is optionally substituted;

$R^4$ is selected from the group consisting of hydrogen, alkyl, alkenyl, alkynyl, cycloalkyl, and (cycloalkyl) alkyl, any of which is optionally substituted with 1, 2, or 3 substituents, each independently selected from the group consisting of hydroxy, halo, haloalkyl, amino, alkylamino, dialkylamino, carboxy, alkoxy, and alkoxycarbonyl;

m is an integer between 1 and 9 (i.e., is selected from 1, 2, 3, 4, 5, 6, 7, 8, and 9); and n and p are each independently an integer between 1 and 20 (i.e., is selected from 1, 2, 3, 4, 5, 6, 7, 8, 9, 10, 11, 12, 13, 14, 15, 16, 17, 18, 19, and 20); and provided that at least one of $R^2$ and $R^3$ is —C(═O)$R^5$ and —OC(═O)$R^6$, respectively.

In another embodiment, Compounds of the Disclosure are compounds of Formula II:

II

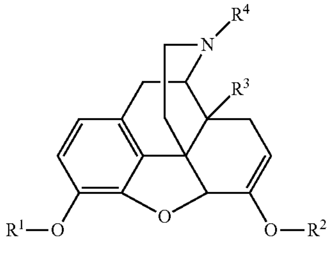

and pharmaceutically acceptable salts and solvates thereof, wherein $R^1$, $R^2$, $R^3$, and $R^4$ are as defined above for Formula I.

In another embodiment, Compounds of the Disclosure are compounds of Formula I or Formula II, and the pharmaceutically acceptable salts and solvates thereof, with the following provisos:

1) the compound is not

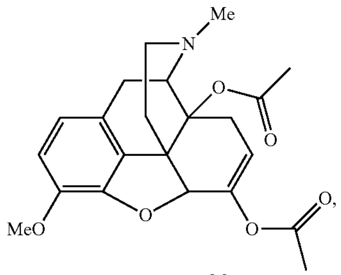

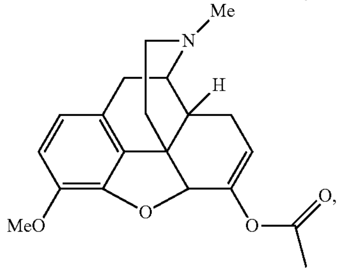

or

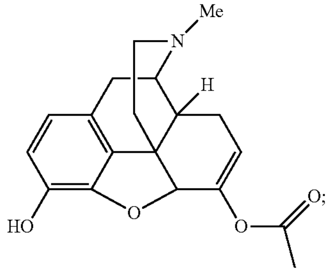

2) when $R^1$ is unsubstituted alkyl, $R^3$ is hydrogen, and $R^4$ is unsubstituted $C_{1-6}$ alkyl, then $R^5$ is other than optionally substituted phenyl or optionally substituted pyridyl; or 3) when $R^1$ is unsubstituted alkyl, $R^4$ is unsubstituted $C_{1-6}$ alkyl, and $R^3$ is —OC(═O)$R^6$, then both $R^5$ and $R^6$ are other than optionally substituted pyridyl.

In another embodiment, Compounds of the Disclosure are compounds of Formula I, and pharmaceutically acceptable salts and solvates thereof, with the following proviso:

4) the compound is not

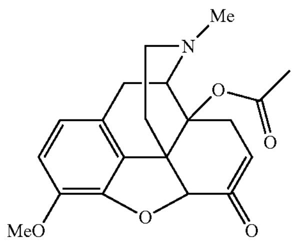

or

-continued

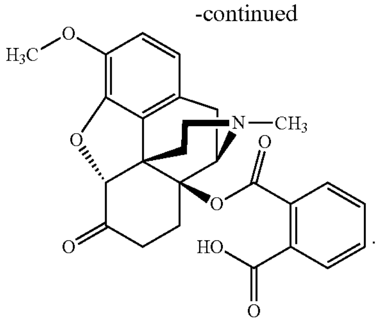

In another embodiment, Compounds of the Disclosure are compounds represented by Formula III:

III

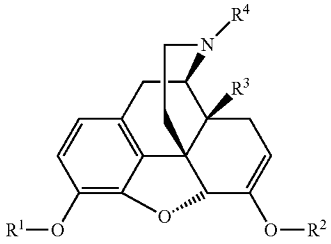

and pharmaceutically acceptable salts and solvates thereof, wherein $R^1$, $R^2$, $R^3$, and $R^4$ are as defined for Formula I.

In another embodiment, Compounds of the Disclosure are compounds represented by Formula IV:

IV

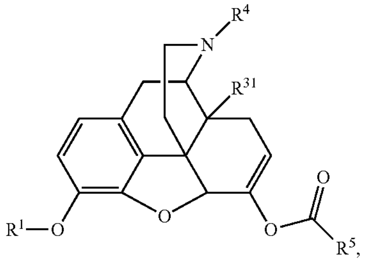

and pharmaceutically acceptable salts and solvates thereof, wherein $R^{31}$ is hydrogen or OH, and $R^1$, $R^4$ and $R^5$ are as defined for Formula I.

In another embodiment, Compounds of the Disclosure are compounds of Formula IV, and the pharmaceutically acceptable salts and solvates thereof, with the following provisos:

1) the compound is not

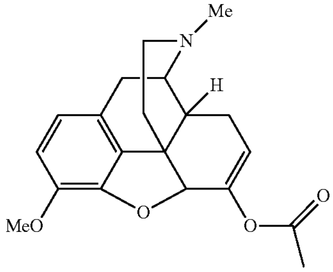

or

-continued

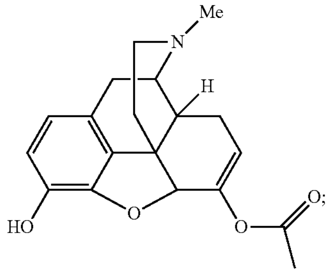

or 2) when $R^1$ is unsubstituted alkyl, $R^{31}$ is hydrogen, and $R^4$ is unsubstituted $C_{1-6}$ alkyl, then $R^5$ is other than optionally substituted phenyl or optionally substituted pyridyl.

In another embodiment, Compounds of the Disclosure are compounds of Formula I or Formula II, wherein $R^2$ is —C(═O)$R^5$, $R^3$ is —OC(═O)$R^6$, and $R^5$ and $R^6$ are the same, represented by Formula V:

V

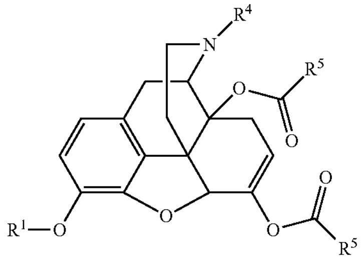

and pharmaceutically acceptable salts and solvates thereof, wherein $R^1$, $R^4$ and $R^5$ are as defined for Formula I.

In another embodiment, Compounds of the Disclosure are compounds of Formula V, and the pharmaceutically acceptable salts and solvates thereof, with the following provisos:

1) the compound is not

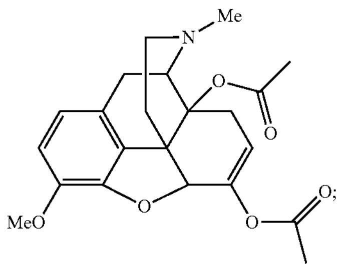 [SMILES: COc1ccc2c3c1OC1C(OC(C)=O)=CCC4(OC(C)=O)C(C2)N(C)CCC314]

or 2) when $R^1$ is unsubstituted alkyl, $R^4$ is unsubstituted $C_{1-6}$ alkyl, then $R^5$ is other than optionally substituted pyridyl.

In still another embodiment, Compounds of the Disclosure are compounds represented by Formula VI:

VI

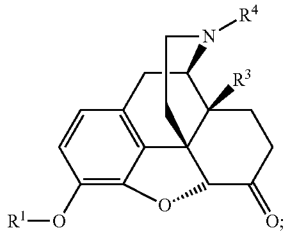

and pharmaceutically acceptable salts and solvates thereof, wherein $R^3$ is —OC(═O)$R^6$, and $R^1$, $R^4$, and $R^6$ are as defined for Formula I.

In another embodiment, Compounds of the Disclosure are compounds of Formula VI, and pharmaceutically acceptable salts and solvates thereof, with the following proviso:

4) the compound is not

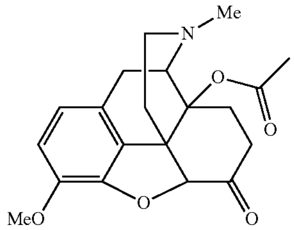

or

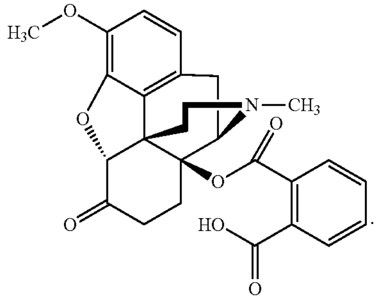

In another embodiment, Compounds of the Disclosure are compounds of any one of Formulae I to VI, wherein $R^1$ is H or alkyl optionally substituted with 1, 2, or 3 substituents, each independently selected from the group consisting of hydroxy, halo, haloalkyl, amino, alkylamino, dialkylamino, carboxy, alkoxy, and alkoxycarbonyl. In another embodiment, $R^1$ is H, unsubstituted $C_{1-10}$ alkyl, or $C_{1-10}$ alkyl substituted with 1 or 2 substituents, each independently selected from the group consisting of hydroxy, halo, halo($C_{1-6}$)alkyl, amino, ($C_{1-6}$ alkyl)amino, di($C_{1-6}$)alkylamino, carboxy, $C_{1-6}$ alkoxy, and $C_{1-6}$ alkoxycarbonyl. In another embodiment, $R^1$ is H, unsubstituted $C_{1-6}$ alkyl, or $C_{1-6}$ alkyl substituted with 1 or 2 substituents, each independently selected from the group consisting of hydroxy, halo, halo($C_{1-4}$)alkyl, amino, ($C_{1-4}$ alkyl)amino, di($C_{1-4}$)alkylamino, carboxy, $C_{1-4}$ alkoxy, and $C_{1-4}$ alkoxycarbonyl, and preferably optionally substituted with 1 or 2 substituents, each independently selected from the group consisting of hydroxy, halo, trifluoromethyl, amino, methylamino, ethylamino, dimethylamino, diethylamino, carboxy, methoxy, ethoxy, methoxycarbonyl, and ethoxycarbonyl.

In another embodiment, Compounds of the Disclosure are compounds of any one of Formulae I to VI, wherein $R^1$ is H or unsubstituted $C_{1-6}$ alkyl. In another embodiment $R^1$ is H. In another embodiment, $R^1$ is unsubstituted $C_{1-4}$ alkyl. In another embodiment, $R^1$ is methyl, ethyl, n-propyl, isopropyl, n-butyl, tert-butyl, iso-butyl, or sec-butyl. In another embodiment, $R^1$ is unsubstituted methyl.

In another embodiment, Compounds of the Disclosure are compounds of any one of Formulae I to VI, wherein $R^1$ is -PEG-$R^7$. "PEG" as used herein, refers to one ethylene oxide unit or an oligomer of 2 or more ethylene oxide subunits. An "oligomer" as used herein refers to a molecule possessing from about 2 to about 50 monomers. In certain embodiments, PEG is $—(CH_2CH_2O)_q—$, wherein q varies from 1 to 50. In another embodiment, q varies from 1 to 10. In another embodiment, q varies from 1 to 5. In another embodiment, q is 1, 2, 3, 4, or 5. In another embodiment, $R^7$ is hydrogen, methyl, ethyl, or benzyl. In another embodiment, $R^7$ is methyl.

In another embodiment, Compounds of the Disclosure are compounds of any one of Formulae I to VI, wherein $R^1$ is a hydroxyl protecting group PG selected from the group consisting of alkyl, arylalkyl, heterocyclo, (heterocyclo)alkyl, acyl, silyl, and carbonate, any of which is optionally substituted.

It will be apparent to a person of ordinary skill in the art in view of this disclosure that certain groups included in the definitions of PG overlap with the other definitions for $R^1$, such as methyl, tert-butyl, etc., and, thus, certain Compounds of the Disclosure having $R^1$ groups that include groups acting as hydroxyl protecting groups can be pharmaceutically active as described herein.

In another embodiment, the hydroxyl protecting group PG is an alkyl group, typically an optionally substituted $C_{1-6}$ alkyl group, and suitably unsubstituted methyl or tert-butyl.

In another embodiment, the hydroxyl protecting group PG is an arylalkyl group. Suitable arylalkyl groups include, for example, an unsubstituted benzyl group, substituted benzyl groups, such as p-methoxybenzyl, and naphthylmethyl.

In another embodiment, the hydroxyl protecting group PG is a heterocyclo group, such as unsubstituted tetrahydropyranyl or optionally substituted tetrahydropyranyl.

In another embodiment, the hydroxyl protecting group PG is a (heterocyclo)alkyl group. Suitable (heterocyclo)alkyl groups include, for example, 4-morpholinyl($C_{1-4}$)alkyl groups, such as, 2-(4-morpholinyl)ethyl.

In another embodiment, the hydroxyl protecting group PG is a silyl group. The term "silyl" as employed herein refers to the group having the following structure:

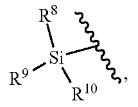

wherein $R^8$, $R^9$, and $R^{10}$ are each independently selected from the group consisting of alkyl, cycloalkyl, aryl, (cycloalkyl)alkyl, or arylalkyl, any of which is optionally substituted. In one embodiment, the silyl group is trimethyl silyl, tert-butyldimethyl silyl, tert-butyldiphenyl silyl, or tri-isopropyl silyl.

In another embodiment, the hydroxyl protecting group PG is an acyl group. The term "acyl" as employed herein refers to the following structure:

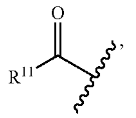

wherein $R^{11}$ is alkyl, cycloalkyl, aryl, (cycloalkyl)alkyl, or arylalkyl, any of which is optionally substituted. The acyl group can be, for example, $C_{1-4}$ alkylcarbonyl (such as, for example, acetyl), arylcarbonyl (such as, for example, benzoyl), levulinoyl, or pivaloyl. In another embodiment, the acyl group is benzoyl.

In another embodiment, the hydroxyl protecting group is a carbonate group. The term "carbonate" as employed herein refers to the following structure:

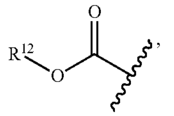

wherein $R^{12}$ is alkyl, alkenyl, cycloalkyl, aryl, (cycloalkyl) alkyl, or arylalkyl, any of which is optionally substituted. Typically, $R^{12}$ is $C_{1-10}$ alkyl (e.g., 2,4-dimethylpent-3-yl), $C_{2-6}$ alkenyl (e.g., ethenyl or prop-2-enyl, i.e., allyl), $C_{3-12}$ cycloalkyl (e.g., adamantyl), phenyl, or benzyl. In one embodiment, the carbonate is benzyloxycarbonyl.

In another embodiment, Compounds of the Disclosure are compounds of any one of Formulae I to VI, wherein $R^1$ is PG, wherein said PG is selected from the group consisting of methyl, tert-butyl, optionally substituted benzyl, optionally substituted benzoyl, acetyl, trimethyl silyl, tert-butyldimethyl silyl, tert-butyldiphenyl silyl, and tri-isopropyl silyl.

In another embodiment, Compounds of the Disclosure are compounds of any one of Formulae I to III, wherein $R^3$ is hydrogen and $R^2$ is —C(═O)$R^5$, wherein $R^5$ is as defined for Formula I.

In another embodiment, Compounds of the Disclosure are compounds of any one of Formulae I to III, wherein $R^3$ is OH and $R^2$ is —C(═O)$R^5$, wherein $R^5$ is as defined for Formula I.

In another embodiment, Compounds of the Disclosure are compounds of any one of Formulae I to III, wherein $R^3$ is —Y-PEG-$R^7$ and $R^2$ is —C(═O)$R^5$, wherein Y, PEG, $R^7$, and $R^5$ are as defined above for Formula I.

In one embodiment, Y is a covalent bond. In another embodiment, Y is a linker. Suitable linkers comprise an ether, amide, urethane, amine, thioether, urea, or a carbon-carbon bond. In certain embodiments, the linker Y is selected from the group consisting of —O—, —O—$CH_2$—, —$CH_2$—O—, —NH—, —S—, —C(═O)—, —C(═O)O—, and —OC(═O)—. In certain embodiments, Y is selected from the group consisting of —O—, —O—$CH_2$—, —$CH_2$—O—, and —NH—. In certain embodiments, Y is —O—. In another embodiment, $R^7$ is hydrogen, methyl, ethyl, or benzyl. In another embodiment, $R^7$ is methyl.

In another embodiment, Compounds of the Disclosure are compounds of any one of Formulae I to III and VI, wherein $R^3$ is —OC(═O)$R^6$, wherein $R^6$ is selected from the group consisting of unsubstituted $C_{1-12}$ alkyl, unsubstituted $C_{2-12}$ alkenyl, unsubstituted $C_{2-12}$ alkynyl, —$CH_2$—O—$(CH_2CH_2O)_m$—$R^7$, —O—$(CH_2CH_2O)_n$—$R^7$, —NH—$(CH_2CH_2O)_p$—$R^7$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; wherein the 6-membered heterocycle is attached to the carbonyl carbon through a carbon atom or through a nitrogen atom; $R^7$ is selected from the group consisting of hydrogen, $C_{1-6}$ alkyl, aryl, heteroaryl, cycloalkyl, and heterocyclo, any of which are optionally substituted; m is an integer between 1 and 9; and n and p are as each independently an integer between 1 and 20. In certain embodiments, $R^7$ is hydrogen, methyl, ethyl, or benzyl. In another embodiment, $R^7$ is methyl.

In another embodiment, Compounds of the Disclosure are compounds of any one of Formulae I to III and VI, wherein $R^3$ is —OC(═O)$R^6$, wherein $R^6$ is selected from the group consisting of unsubstituted $C_{1-6}$ alkyl, unsubstituted $C_{7-12}$ alkyl, unsubstituted $C_{2-6}$ alkenyl, unsubstituted $C_{2-6}$ alkynyl, —$CH_2$—O—$(CH_2CH_2O)_m$—$CH_3$, —O—$(CH_2CH_2O)_n$—$CH_3$, —NH—$(CH_2CH_2O)_p$—$CH_3$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; m is 1, 2, 3, 4, or 5; n and p are each independently selected from the group consisting of 1, 2, 3, 4, 5, 6, 7, 8, 9, and 10; and wherein the 6-membered heterocycle is attached to the carbonyl carbon through a carbon atom or through a nitrogen atom. In another embodiment, $R^6$ is selected from the group consisting of unsubstituted $C_{1-6}$ alkyl, unsubstituted $C_{7-12}$ alkyl, unsubstituted $C_{2-6}$ alkenyl, unsubstituted $C_{2-6}$ alkynyl, —$CH_2$—O—$(CH_2CH_2O)_m$—$CH_3$, —O—$(CH_2CH_2O)_n$—$CH_3$, —NH—$(CH_2CH_2O)_p$—$CH_3$, phenyl, benzyl, phenethyl, pyridyl, $C_{3-6}$ cycloalkyl, ($C_{3-6}$ cycloalkyl)($C_{1-4}$)alkyl, $C_{3-6}$ cycloalkenyl, ($C_{3-6}$ cycloalkenyl)($C_{1-4}$)alkyl, 6-membered heterocycle, and (5- or 6-membered heterocycle)($C_{1-4}$)alkyl, wherein the phenyl, pyridyl, $C_{3-6}$ cycloalkyl, $C_{3-6}$ cycloalkenyl, and heterocycle moiety is optionally substituted with 1, 2, or 3 substituents, each independently selected from the group consisting of $C_{1-4}$ alkyl, hydroxy, halo, halo($C_{1-4}$) alkyl, amino, ($C_{1-4}$)alkylamino, di($C_{1-4}$)alkylamino, carboxy, $C_{1-4}$ alkoxy, and $C_{1-4}$ alkoxycarbonyl, and preferably optionally substituted with 1 or 2 substituents, each independently selected from the group consisting of methyl, hydroxy, halo, trifluoromethyl, amino, methylamino, ethylamino, dimethylamino, diethylamino, carboxy, methoxy, ethoxy, methoxycarbonyl, and ethoxycarbonyl; m is 1, 2, or 3; n and p are each independently selected from the group consisting of 1, 2, 3, 4, 5, and 6; and wherein the 6-membered heterocycle is attached to the carbonyl carbon by a carbon atom.

In another embodiment, Compounds of the Disclosure are compounds of any of Formulae I to III and VI, wherein $R^3$ is —OC(═O)$R^6$, and $R^6$ is unsubstituted $C_{1-6}$ alkyl, unsubstituted $C_{2-6}$ alkenyl, or $C_{2-6}$ alkynyl. In another embodiment, $R^6$ is unsubstituted $C_{1-4}$ alkyl. In another embodiment, $R^6$ is methyl, ethyl, n-propyl, iso-propyl, n-butyl, tert-butyl, iso-butyl, or sec-butyl. In another embodiment, $R^6$ is methyl. In another embodiment, $R^6$ is ethyl, propyl, or n-butyl.

In another embodiment, Compounds of the Disclosure are compounds of any one of Formulae I to III and VI, wherein $R^3$ is —OC(═O)$R^6$, and $R^6$ is unsubstituted $C_{7-12}$ alkyl. In another embodiment, $R^6$ is heptyl, octyl, nonyl, decyl, undecyl, or dodecyl. In another embodiment, $R^6$ is undecyl.

In another embodiment, Compounds of the Disclosure are compounds of any one of Formulae I to III and VI, wherein $R^3$ is —OC(═O)$R^6$ and $R^6$ is —$CH_2$—O—$CH_2CH_2O$—$CH_3$, —$CH_2$—O—$CH_2CH_2O$—$CH_2CH_2O$—$CH_3$, —$CH_2$—O—$(CH_2CH_2O)_3$—$CH_3$, —O—$CH_2CH_2O$—$CH_3$, —O—$CH_2CH_2O$—$CH_2CH_2O$—$CH_3$, or —O—$(CH_2CH_2O)_3$—$CH_3$. In another embodiment, $R^6$ is —$CH_2$—O—$CH_2CH_2O$—$CH_2CH_2O$—$CH_3$.

In another embodiment, Compounds of the Disclosure are compounds of any one of Formulae I to VI, wherein $R^4$ is hydrogen.

In another embodiment, Compounds of the Disclosure are compounds of any one of Formulae I to VI, wherein $R^4$ is alkyl, alkenyl, alkynyl, cycloalkyl, and (cycloalkyl)alkyl, any of which is optionally substituted with 1, 2, or 3 substituents, each independently selected from the group consisting of hydroxy, halo, haloalkyl, amino, alkylamino, dialkylamino, carboxy, alkoxy, and alkoxycarbonyl.

In another embodiment, Compounds of the Disclosure are compounds of any one of Formulae I to VI, wherein $R^4$ is $C_{1-10}$ alkyl, $C_{2-10}$ alkenyl, $C_{2-10}$ alkynyl, $C_{3-6}$ cycloalkyl, or $C_{3-6}$ (cycloalkyl)($C_{1-6}$)alkyl, any of which is optionally substituted with 1, 2, or 3 substituents, each independently selected from the group consisting of hydroxy, halo, halo($C_{1-6}$)alkyl, amino, $C_{1-6}$ alkylamino, di($C_{1-6}$)alkylamino, carboxy, $C_{1-6}$ alkoxy, and $C_{1-6}$ alkoxycarbonyl.

In another embodiment, Compounds of the Disclosure are compounds of any one of Formulae I to VI, wherein $R^4$ is $C_{1-6}$ alkyl, $C_{2-6}$ alkenyl, $C_{2-6}$ alkynyl, $C_{3-6}$ cycloalkyl, or $C_{3-6}$ cycloalkyl($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

In another embodiment, Compounds of the Disclosure are compounds of any one of Formulae I to VI, wherein $R^4$ is $C_{1-4}$ alkyl, $C_{2-4}$ alkenyl, $C_{2-4}$ alkynyl, $C_{3-6}$ cycloalkyl, or $C_{3-6}$ cycloalkyl($C_{1-2}$)alkyl, any of which is optionally substituted with 1 or 2 substituents, each independently selected from the group consisting of hydroxy, halo, halo($C_{1-2}$)alkyl, amino, $C_{1-2}$ alkylamino, di($C_{1-2}$)alkylamino, carboxy, $C_{1-2}$ alkoxy, and $C_{1-2}$ alkoxycarbonyl, and preferably optionally substituted with 1 or 2 substituents, each independently selected from the group consisting of hydroxy, halo, trifluoromethyl, amino, methylamino, ethylamino, dimethylamino, diethylamino, carboxy, methoxy, ethoxy, methoxycarbonyl, and ethoxycarbonyl.

In another embodiment, Compounds of the Disclosure are compounds of any one of Formulae I to VI, wherein $R^4$ is unsubstituted $C_{1-6}$ alkyl, and advantageously unsubstituted $C_{1-4}$ alkyl (such as methyl, ethyl, n-propyl, iso-propyl, n-butyl, or tert-butyl). In another embodiment, $R^4$ is methyl or ethyl. In another embodiment, $R^4$ is methyl.

In another embodiment, Compounds of the Disclosure are compounds of any one of Formulae I to VI, wherein $R^4$ is $C_{3-6}$ (cycloalkyl)($C_{1-4}$)alkyl, such as cyclopropyl($C_{1-4}$)alkyl, cyclobutyl($C_{1-4}$)alkyl, cyclopentyl($C_{1-4}$)alkyl, or cyclohexyl ($C_{1-4}$)alkyl, optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and preferably optionally substituted with 1 or 2 substituents, each independently selected from the group consisting of hydroxy, halo, trifluoromethyl, amino, methylamino, ethylamino, dimethylamino, diethylamino, carboxy, methoxy, ethoxy, methoxycarbonyl, and ethoxycarbonyl. In another embodiment, $R^4$ is unsubstituted cyclopropyl ($C_{1-4}$)alkyl. In another embodiment, Compounds of the Disclosure are compounds of any one of Formulae I to VI, wherein $R^4$ is unsubstituted (cyclopropyl)methyl, 2-(cyclopropyl)ethyl or 3-(cyclopropyl)propyl.

In another embodiment, Compounds of the Disclosure are compounds of any one of Formulae I to VI, wherein $R^4$ is $C_{1-6}$ alkyl, and preferably $C_{1-4}$ alkyl, substituted with 1, 2, or 3 substituents, each independently selected from the group consisting of halo (such as fluoro) and halo($C_{1-4}$)alkyl (such as, for example, trifluoro($C_{1-2}$)alkyl).

In another embodiment, Compounds of the Disclosure are compounds of any one of Formulae I to VI, wherein $R^4$ is $C_{2-6}$ alkenyl (e.g., $C_{2-4}$ alkenyl), which is unsubstituted or substituted with 1, 2, or 3 substituents, each independently selected from the group consisting of halo (such as fluoro) and halo($C_{1-4}$)alkyl (such as, for example, trifluoro($C_{1-2}$) alkyl).

In another embodiment, Compounds of the Disclosure are compounds of any one of Formulae I to III, wherein $R^2$ is —C(═O)$R^5$ and $R^5$ is selected from the group consisting of unsubstituted $C_{1-6}$ alkyl, unsubstituted $C_{7-12}$ alkyl, unsubstituted $C_{2-6}$ alkenyl, unsubstituted $C_{2-6}$ alkynyl, —$CH_2$—O—$(CH_2CH_2O)_m$—$R^7$, —O—$(CH_2CH_2O)_n$—$R^7$, —NH—$(CH_2CH_2O)_p$—$R^7$, phenyl, benzyl, phenethyl, pyridyl, cycloalkyl, (cycloalkyl)alkyl, cycloalkenyl, (cycloalkenyl) alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; wherein the 6-membered heterocycle is attached to the carbonyl carbon through a carbon atom or through a nitrogen atom; $R^7$ is selected from the group consisting of hydrogen, $C_{1-6}$ alkyl, aryl, heteroaryl, cycloalkyl, and heterocyclo, any of which are optionally substituted; m is an integer between 1 and 9; and n and p are as each independently an integer between 1 and 20. In certain embodiments, $R^7$ is hydrogen, methyl, ethyl, or benzyl. In another embodiment, $R^7$ is methyl.

In another embodiment, Compounds of the Disclosure are compounds of any one of Formulae I to III, wherein $R^2$ is —C(═O)$R^5$ and $R^5$ is selected from the group consisting of unsubstituted $C_{1-6}$ alkyl, unsubstituted $C_{7-12}$ alkyl, unsubstituted $C_{2-6}$ alkenyl, unsubstituted $C_{2-6}$ alkynyl, —$CH_2$—O—$(CH_2CH_2O)_m$—$CH_3$, —O—$(CH_2CH_2O)_n$—$CH_3$, —NH—$(CH_2CH_2O)_p$—$CH_3$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; m is 1, 2, 3, 4, or 5; n and p are each independently selected from the group consisting of 1, 2, 3, 4, 5, 6, 7, 8, 9, and 10; and wherein the 6-membered heterocycle is attached to the carbonyl carbon through a carbon atom or through a nitrogen atom. In another embodiment, $R^5$ is selected from the group consisting of unsubstituted $C_{1-6}$ alkyl, unsubstituted $C_{7-12}$ alkyl, unsubstituted $C_{2-6}$ alkenyl, unsubstituted $C_{2-6}$ alkynyl, —$CH_2$—O—$(CH_2CH_2O)_m$—$CH_3$, —O—$(CH_2CH_2O)_n$—$CH_3$, —NH—$(CH_2CH_2O)_p$—$CH_3$, phenyl, benzyl, phenethyl, pyridyl, $C_{3-6}$ cycloalkyl, ($C_{3-6}$ cycloalkyl)($C_{1-4}$)alkyl, $C_{3-6}$ cycloalkenyl, ($C_{3-6}$ cycloalkenyl)($C_{1-4}$)alkyl, 6-membered heterocycle, and (5- or 6-membered heterocycle)($C_{1-4}$)alkyl, wherein the phenyl, pyridyl, $C_{3-6}$ cycloalkyl, $C_{3-6}$ cycloalkenyl, and heterocycle moiety is optionally substituted with 1, 2, or 3 substituents, each independently selected from the group consisting of $C_{1-4}$ alkyl, hydroxy, halo, halo($C_{1-4}$) alkyl, amino, ($C_{1-4}$)alkylamino, di($C_{1-4}$)alkylamino, carboxy, $C_{1-4}$ alkoxy, and $C_{1-4}$ alkoxycarbonyl, and preferably optionally substituted with 1 or 2 substituents, each independently selected from the group consisting of methyl, hydroxy, halo, trifluoromethyl, amino, methylamino, ethylamino, dimethylamino, diethylamino, carboxy, methoxy, ethoxy, methoxycarbonyl, and ethoxycarbonyl; m is 1, 2, or 3; n and p are each independently selected from the group consisting of 1, 2, 3, 5, 5, and 6; and wherein the 6-membered heterocycle is attached to the carbonyl carbon through a carbon atom or through a nitrogen atom.

In another embodiment, Compounds of the Disclosure are compounds of any one of Formulae I to III, wherein $R^2$ is $C(=O)R^5$ and $R^5$ is unsubstituted $C_{1-6}$ alkyl, unsubstituted $C_{2-6}$ alkenyl, or $C_{2-6}$ alkynyl. In another embodiment, $R^5$ is unsubstituted $C_{1-4}$ alkyl. In another embodiment, $R^5$ is methyl, ethyl, n-propyl, iso-propyl, n-butyl, tert-butyl, iso-butyl, or sec-butyl. In another embodiment, $R^5$ is unsubstituted $C_{1-4}$ alkyl. In another embodiment, $R^5$ is methyl. In another embodiment, $R^5$ is ethyl, propyl, or n-butyl.

In another embodiment, Compounds of the Disclosure are compounds of any one of Formulae I to III, wherein $R^2$ is $—C(=O)R^5$ and $R^5$ is unsubstituted $C_{7-12}$ alkyl. In another embodiment, $R^5$ is heptyl, octyl, nonyl, decyl, undecyl, or dodecyl. In another embodiment, $R^5$ is undecyl.

In another embodiment, Compounds of the Disclosure are compounds of any one of Formulae I to III, wherein $R^2$ is $—C(=O)R^5$ and $R^5$ is $—CH_2—O—CH_2CH_2O—CH_3$, $—CH_2—O—CH_2CH_2O—CH_2CH_2O—CH_3$, $—CH_2—O—(CH_2CH_2O)_3—CH_3$, $—O—CH_2CH_2O—CH_3$, $—O—CH_2CH_2O—CH_2CH_2O—CH_3$, or $—O—(CH_2CH_2O)_3—CH_3$. In another embodiment, $R^5$ is $—CH_2—O—CH_2CH_2O—CH_2CH_2O—CH_3$.

In another embodiment, Compounds of the Disclosure are compounds of Formula IV, wherein $R^5$ is selected from the group consisting of unsubstituted $C_{1-6}$ alkyl, unsubstituted $C_{7-12}$ alkyl, unsubstituted $C_{2-6}$ alkenyl, unsubstituted $C_{2-6}$ alkynyl, $—CH_2—O—(CH_2CH_2O)_m—R^7$, $—O—(CH_2CH_2O)_n—R^7$, $—NH—(CH_2CH_2O)_p—R^7$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; wherein the 6-membered heterocycle is attached to the carbonyl carbon through a carbon atom or through a nitrogen atom; $R^7$ is selected from the group consisting of hydrogen, $C_{1-6}$ alkyl, aryl, heteroaryl, cycloalkyl, and heterocyclo, any of which are optionally substituted; m is an integer between 1 and 9; and n and p are as each independently an integer between 1 and 20. In certain embodiments, $R^7$ is hydrogen, methyl, ethyl, or benzyl. In another embodiment, $R^7$ is methyl.

In another embodiment, Compounds of the Disclosure are compounds of Formula IV, wherein $R^5$ is selected from the group consisting of unsubstituted $C_{1-6}$ alkyl, unsubstituted $C_{7-12}$ alkyl, unsubstituted $C_{2-6}$ alkenyl, unsubstituted $C_{2-6}$ alkynyl, $—CH_2—O—(CH_2CH_2O)_m—CH_3$, $—O—(CH_2CH_2O)_n—CH_3$, $—NH—(CH_2CH_2O)_p—CH_3$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; m is 1, 2, 3, 4, or 5; n and p are each independently selected from the group consisting of 1, 2, 3, 4, 5, 6, 7, 8, 9, and 10; and wherein the 6-membered heterocycle is attached to the carbonyl carbon through a carbon atom or through a nitrogen atom. In another embodiment, $R^5$ is selected from the group consisting of unsubstituted $C_{1-6}$ alkyl, unsubstituted $C_{7-12}$ alkyl, unsubstituted $C_{2-6}$ alkenyl, unsubstituted $C_{2-6}$ alkynyl, $—CH_2—O—(CH_2CH_2O)_m—CH_3$, $—O—(CH_2CH_2O)_n—CH_3$, $—NH—(CH_2CH_2O)_p—CH_3$, phenyl, benzyl, phenethyl, pyridyl, $C_{3-6}$ cycloalkyl, ($C_{3-6}$ cycloalkyl)($C_{1-4}$)alkyl, $C_{3-6}$ cycloalkenyl, ($C_{3-6}$ cycloalkenyl)($C_{1-4}$alkyl, 6-membered heterocycle, and (5- or 6-membered heterocycle) ($C_{1-4}$)alkyl, wherein the phenyl, pyridyl, $C_{3-6}$ cycloalkyl, $C_{3-6}$ cycloalkenyl, and heterocycle moiety is optionally substituted with 1, 2, or 3 substituents, each independently selected from the group consisting of $C_{1-4}$ alkyl, hydroxy, halo, halo($C_{1-4}$)alkyl, amino, ($C_{1-4}$)alkylamino, di($C_{1-4}$)alkylamino, carboxy, $C_{1-4}$ alkoxy, and $C_{1-4}$ alkoxycarbonyl, and preferably optionally substituted with 1 or 2 substituents, each independently selected from the group consisting of methyl, hydroxy, halo, trifluoromethyl, amino, methylamino, ethylamino, dimethylamino, diethylamino, carboxy, methoxy, ethoxy, methoxycarbonyl, and ethoxycarbonyl; m is 1, 2, or 3; n and p are each independently selected from the group consisting of 1, 2, 3, 5, 5, and 6; and wherein the 6-membered heterocycle is attached to the carbonyl carbon through a carbon atom or through a nitrogen atom.

In another embodiment, Compounds of the Disclosure are compounds of Formula IV, wherein $R^5$ is unsubstituted $C_{1-6}$ alkyl, unsubstituted $C_{2-6}$ alkenyl, or $C_{2-6}$ alkynyl. In another embodiment, $R^5$ is unsubstituted $C_{1-4}$ alkyl. In another embodiment, $R^5$ is methyl, ethyl, n-propyl, iso-propyl, n-butyl, tert-butyl, iso-butyl, or sec-butyl. In another embodiment, $R^5$ is unsubstituted $C_{1-4}$ alkyl. In another embodiment, $R^5$ is methyl. In another embodiment, $R^5$ is ethyl, propyl, or n-butyl.

In another embodiment, Compounds of the Disclosure are compounds of Formula IV, wherein $R^5$ is unsubstituted $C_{7-12}$ alkyl. In another embodiment, $R^5$ is heptyl, octyl, nonyl, decyl, undecyl, or dodecyl. In another embodiment, $R^5$ is undecyl.

In another embodiment, Compounds of the Disclosure are compounds of Formula IV, wherein $R^5$ is $—CH_2—O—CH_2CH_2O—CH_3$, $—CH_2—O—CH_2CH_2O—CH_2CH_2O—CH_3$, $—CH_2—O—(CH_2CH_2O)_3—CH_3$, $—O—CH_2CH_2O—CH_3$, $—O—CH_2CH_2O—CH_2CH_2O—CH_3$, or $—O—(CH_2CH_2O)_3—CH_3$. In another embodiment, $R^5$ is $—CH_2—O—CH_2CH_2O—CH_2CH_2O—CH_3$.

In another embodiment, Compounds of the Disclosure are compounds of any one of Formulae I to III, wherein $R^2$ is $—C(=O)R^5$, $R^3$ is $—OC(=O)R^6$, and $R^5$ and $R^6$ are the same, i.e., compounds of Formula V, wherein $R^5$ is as defined above, provided that the compound is not

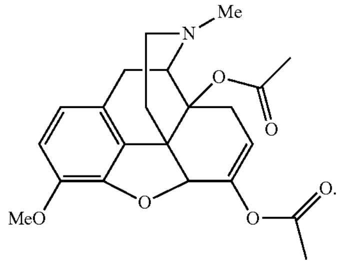 [SMILES: COc1ccc2c3c1OC1C(OC(C)=O)=CCC4(OC(C)=O)C(C2)N(C)CCC314]

In another embodiment, in compounds of Formula V, each $R^5$ is butyl or undecyl. In another embodiment, each $R^5$ is $—CH_2—O—CH_2CH_2O—CH_2CH_2O—CH_3$.

In another embodiment, Compounds of the Disclosure are compounds of any one of Formulae I to III, wherein $R^3$ is $—OC(═O)R^6$, and $R^5$ and $R^6$ are different.

In another embodiment, Compounds of the Disclosure are compounds of Formula II or Formula III, wherein $R^1$ is H or unsubstituted $C_{1-6}$ alkyl;

$R^2$ is $—C(O)(C_{1-6})$alkyl;

$R^3$ is H or OH; and $R^4$ is unsubstituted $C_{1-6}$ alkyl, provided that the compound is not

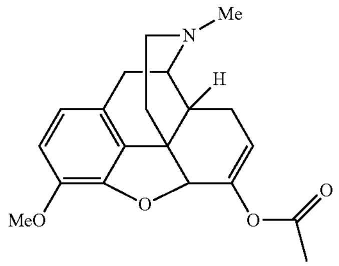

or

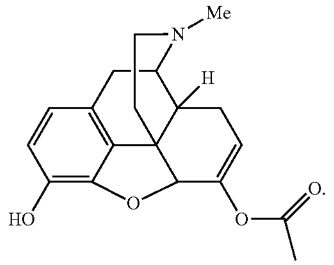

In another embodiment, Compounds of the Disclosure are compounds of Formula II or Formula III which are oxycodone enol esters and the pharmaceutically acceptable salts and solvates thereof, wherein $R_1$ is methyl, $R^3$ is OH, $R^4$ is methyl, and $R^2$ is $—C(═O)R^5$, wherein $R^5$ is as defined above for Formula II. In another embodiment, Compounds of the Disclosure are compounds of Formula II or Formula III having the structure

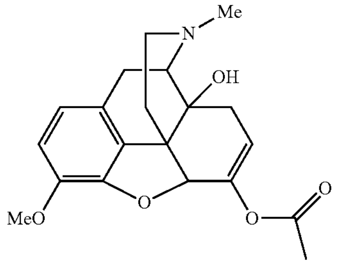

or

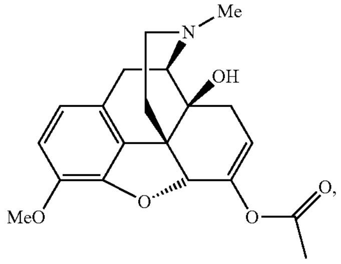

respectively, and the pharmaceutically acceptable salts and solvates thereof. Alternatively, these oxycodone enol esters and the pharmaceutically acceptable salts and solvates thereof are compounds of Formula IV, wherein $R_1$ is methyl, $R^{31}$ is OH, $R^4$ is methyl, and $R^2$ is $—C(═O)R^5$, wherein $R^5$ is as defined above for Formula II.

In another embodiment, Compounds of the Disclosure are compounds of Formula II or Formula III which are oxymorphone enol esters and the pharmaceutically acceptable salts and solvates thereof, wherein $R_1$ is hydrogen, $R^3$ is OH, $R^4$ is methyl, and $R^2$ is $—C(═O)R^5$, wherein $R^5$ is as defined above for Formula II. Alternatively, these oxymorphone enol esters and the pharmaceutically acceptable salts and solvates thereof are compounds of Formula IV, wherein $R_1$ is hydrogen, $R^{31}$ is OH, $R^4$ is methyl, and $R^5$ is as defined above for Formula II.

In another embodiment, Compounds of the Disclosure are compounds of any one of Formulae II to IV which are hydrocodone enol esters and the pharmaceutically acceptable salts and solvates thereof, wherein $R_1$ is methyl, $R^3/R^{31}$ is H, $R^4$ is methyl, $R^2$ is $—C(═O)R^5$, and $R^5$ is as defined above for Formula II, with the proviso that the compound is not

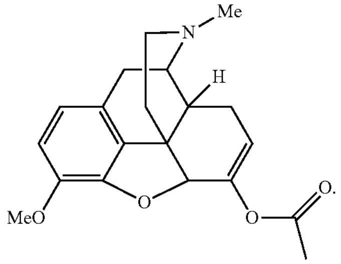 [SMILES: COc1ccc2c3c1OC1C(OC(C)=O)=CCC4C(C2)N(C)CCC314]

In another embodiment, Compounds of the Disclosure are compounds of any one of Formulae II to IV which are hydromorphone enol esters and the pharmaceutically acceptable salts and solvates thereof, wherein $R_1$ is hydrogen, $R^3/R^{31}$ is H, $R^4$ is methyl, and $R^2$ is $—C(═O)R^5$, and $R^5$ is as defined above for Formula II, with the proviso that the compound is not

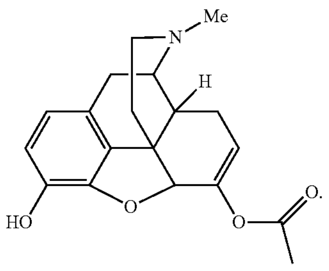 [SMILES: CC(=O)OC1=CCC2C3Cc4ccc(O)c5c4C2(CCN3C)C1O5]
In another embodiment, Compounds of the Disclosure include:
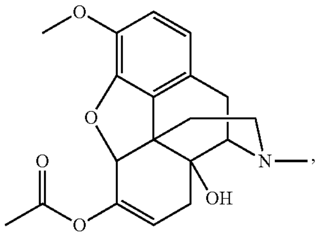
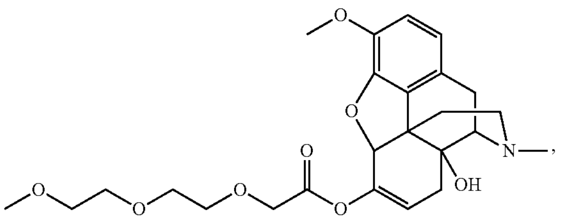
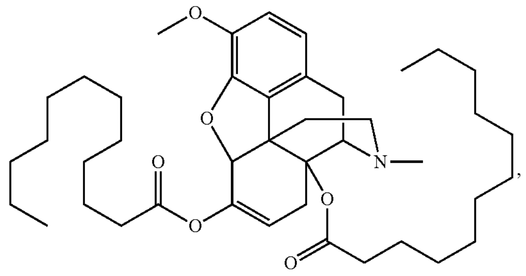
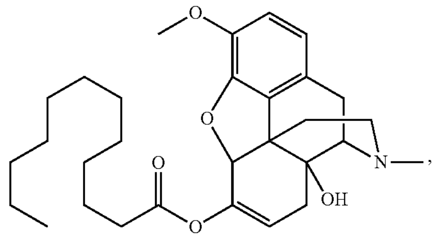
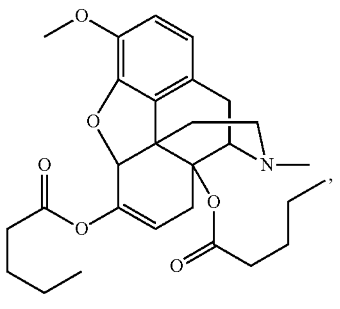
-continued
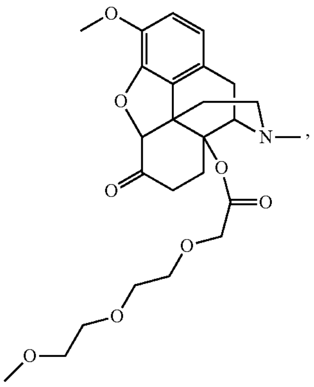
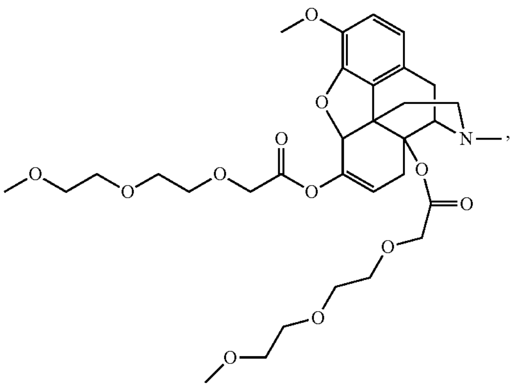
and
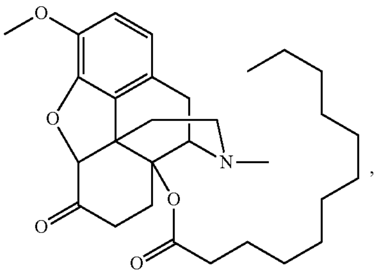
and pharmaceutically acceptable salts and solvates thereof.
In another embodiment, Compounds of the Disclosure include:
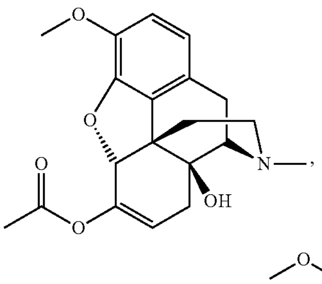
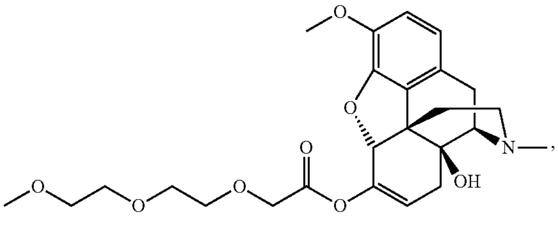

-continued

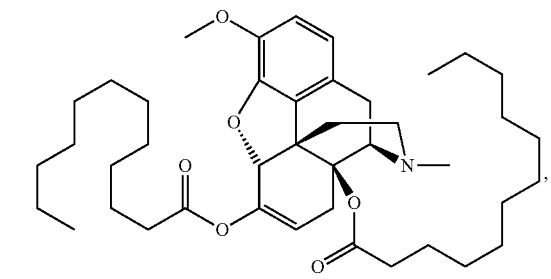

,

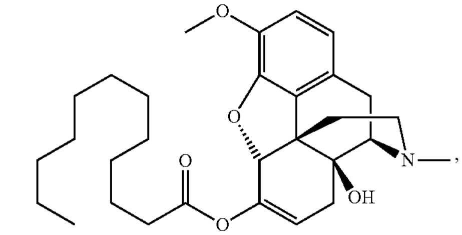

,

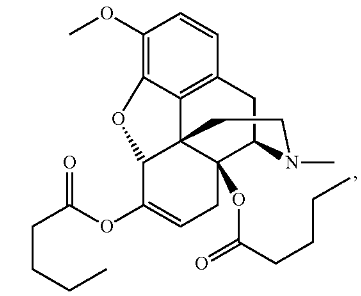

,

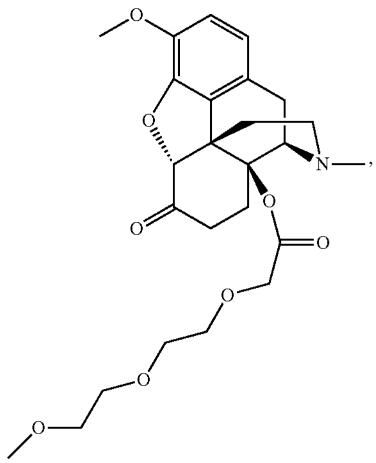

,

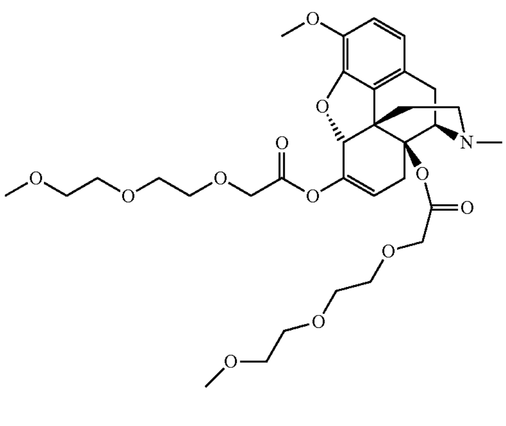

, and

-continued

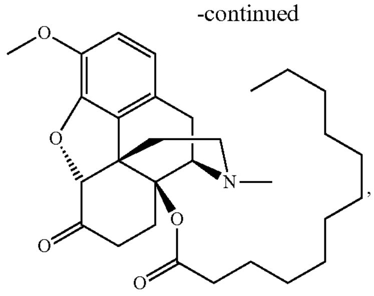

, and pharmaceutically acceptable salts and solvates thereof.

Optional substituents attached to aryl, phenyl and heteroaryl rings each take the place of a hydrogen atom that would otherwise be present in any position on the aryl, phenyl or heteroaryl rings.

Useful halo or halogen groups include fluorine, chlorine, bromine and iodine.

Useful alkyl groups are selected from straight-chain and branched-chain $C_{1-12}$ alkyl groups. Typical $C_{1-12}$ alkyl groups include methyl (Me), ethyl, n-propyl, n-butyl, n-pentyl, n-hexyl, n-heptyl, n-octyl, n-nonyl, n-decyl, n-undecyl, n-dodecyl, isopropyl, sec-butyl, tert-butyl, iso-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl, among others. In one embodiment, useful $C_{1-12}$ alkyl groups are straight chain $C_{1-12}$ alkyl groups. In another embodiment, useful alkyl groups are selected from straight-chain and branched-chain $C_{1-10}$ alkyl groups, i.e., straight chain $C_{1-10}$ alkyl groups and branched chain $C_{3-10}$ alkyl groups. In another embodiment, useful alkyl groups are selected from straight-chain and branched-chain $C_{1-6}$ alkyl groups, i.e., straight chain $C_{1-6}$ alkyl groups and branched chain $C_{3-6}$ alkyl groups. Typical $C_{1-6}$ alkyl groups include methyl, ethyl, propyl, isopropyl, butyl, sec-butyl, tert-butyl, iso-butyl, pentyl, 3-pentyl, hexyl, among others. In one embodiment, useful alkyl groups are selected from straight-chain and branched-chain $C_{1-4}$ alkyl groups, i.e., straight chain $C_{1-4}$ alkyl groups and branched chain $C_{3-4}$ alkyl groups. Typical $C_{1-4}$ alkyl groups include methyl, ethyl, propyl, isopropyl, butyl, sec-butyl, tert-butyl, and iso-butyl. Typical $C_{1-2}$ alkyl groups include methyl and ethyl. In this application, a $C_{1-6}$ alkyl group refers to straight-chain and branched-chain $C_{1-6}$ alkyl groups, and a $C_{1-4}$ alkyl group refers to straight-chain and branched-chain $C_{1-4}$ alkyl groups, as defined above in this paragraph. In another embodiment, useful alkyl groups are selected from straight-chain and branched-chain $C_{7-12}$ alkyl groups.

Useful alkenyl groups are selected from straight-chain and branched-chain $C_{2-12}$ alkenyl groups. As used herein, the term "$C_{2-12}$ alkenyl" as used by itself or as part of another group refers to straight chain and branched non-cyclic hydrocarbons having from 2 to 12 carbon atoms and including at least one carbon-carbon double bond. Representative Typical $C_{2-12}$ alkenyl groups include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2- butenyl, 1-hexenyl, 2-hexenyl, 3-hexenyl, and the like. In one embodiment, useful $C_{2-12}$ alkenyl groups are $C_{2-10}$ alkenyl groups. In another embodiment, useful $C_{2-12}$ alkenyl groups are $C_{2-6}$ alkenyl groups. Typical $C_{2-6}$ alkenyl groups include ethenyl (i.e., vinyl), allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, and 3-hexenyl. Typical $C_{2-4}$ alkenyl groups include ethenyl, propenyl, isopropenyl, butenyl, and sec-butenyl.

Useful alkynyl groups are selected from straight-chain and branched-chain $C_{2-12}$ alkynyl groups. As used herein, the term "$C_{2-12}$ alkynyl" as used by itself or as part of another groups refers to straight chain and branched non-cyclic hydrocarbons having from 2 to 12 carbon atoms and including at least one carbon-carbon triple bond. Representative straight chain and branched $C_{2-12}$ alkynyl groups include acetylenyl, propynyl, butyn-1-yl, butyn-2-yl, pentyn-1-yl, pentyn-2-yl, 3-methylbutyn-1-yl, pentyn-4-yl, hexyn-1-yl, hexyn-2-yl, hexyn-3-yl, and the like. In one embodiment, the $C_{2-12}$ alkynyl group is $C_{2-10}$ alkynyl group. In another embodiment, the $C_{2-12}$ alkynyl group is $C_{2-6}$ alkynyl group. Typical $C_{2-6}$ alkynyl groups include acetylenyl (i.e., ethynyl), propynyl, butyn-1-yl, butyn-2-yl, pentyn-1-yl, pentyn-2-yl, 3-methylbutyn-1-yl, pentyn-4-yl, and hexyn-1-yl groups. In another embodiment, the $C_{2-10}$ alkynyl group is a $C_{2-4}$ alkynyl group. Typical $C_{2-4}$ alkynyl groups include ethynyl, propynyl, butyn-1-yl, and butyn-2-yl groups.

Useful haloalkyl groups include any of the above-mentioned $C_{1-12}$ alkyl groups, preferably any of the above-mentioned $C_{1-6}$ alkyl groups, and preferably any of the above-mentioned $C_{1-4}$ alkyl groups, substituted by one or more fluorine, chlorine, bromine or iodine atoms (e.g., fluoromethyl, difluoromethyl, difluorochloromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups).

Useful cycloalkyl groups are selected from saturated cyclic hydrocarbon groups containing 1, 2, or 3 rings having 3, 4, 5, 6, 7, 8, 9, 10, 11, or 12 carbon atoms (i.e., $C_{3-12}$ cycloalkyl) or the number of carbons designated. In one embodiment, the cycloalkyl has one or two rings. Exemplary cycloalkyl groups include cyclopropyl, cyclobutyl, cyclopentyl, cyclohexyl, cycloheptyl, cyclooctyl, norbornyl, decalin, and adamantyl. In another embodiment, the cycloalkyl is a $C_{3-6}$ cycloalkyl. Typical $C_{3-6}$ cycloalkyl groups include cyclopropyl, cyclobutyl, cyclopentyl and cyclohexyl.

Useful cycloalkenyl groups are selected from partially unsaturated (i.e., containing one or two double bonds) cyclic hydrocarbon groups containing 1, 2, or 3 rings having 4, 5, 6, 7, 8, 9, 10, 11, or 12 carbon atoms (i.e., $C_4$-$C_{12}$ cycloalkenyl) or the number of carbons designated. In one embodiment, the cycloalkenyl has one or two rings. In another embodiment, the cycloalkenyl is a $C_{3-8}$ cycloalkenyl. In another embodiment, the cycloalkenyl is $C_{3-7}$ cycloalkenyl. In another embodiment, the cycloalkenyl is $C_{3-6}$ cycloalkenyl. In one embodiment, the cycloalkenyl group contains one double bond. Exemplary cycloalkenyl groups containing one double bond include cyclobutenyl, cyclopentenyl, cyclohexenyl, cycloheptenyl, cyclooctenyl, cyclononenyl, and cyclodecenyl. In another embodiment, the cycloalkenyl group contains two double bonds. Preferably, the cycloalkenyl groups containing two double bonds have 5, 6, 7, 8, 9, 10, 11, or 12 carbon atoms (i.e., $C_5$-$C_{12}$ cycloalkadienyl). Exemplary cycloalkenyl groups having two double bonds include cyclopentadienyl, cyclohexadienyl, cycloheptadienyl, cyclooctadienyl, cyclononadienyl, and cyclodecadienyl.

Useful alkoxy groups include oxygen substituted by one of the $C_{1-12}$ alkyl groups mentioned above (e.g., methoxy, ethoxy, propoxy, iso-propoxy, butoxy, tert-butoxy, iso-butoxy, sec-butoxy, pentyloxy, hexyloxy, heptyloxy, octyloxy, nonyloxy, decyloxy, undecyloxy, and dodecyloxy), preferably by one of the $C_{1-6}$ alkyl groups, and more preferably by one of the $C_{1-4}$ alkyl groups.

Useful halo($C_{1-6}$)alkoxy groups include oxygen substituted by one of the halo($C_{1-6}$)alkyl groups mentioned above (e.g., fluoromethoxy, difluoromethoxy, trifluoromethoxy, and 2,2,2-trifluoroethoxy).

Useful (cycloalkyl)alkyl groups include any of the above-mentioned $C_{1-12}$ alkyl groups, and preferably any of the above-mentioned $C_{1-6}$ alkyl groups, substituted with any of the above-mentioned cycloalkyl groups (e.g., (cyclopropyl)methyl, 2-(cyclopropyl)ethyl, (cyclopropyl)propyl, (cyclobutyl)methyl, (cyclopentyl)methyl, and (cyclohexyl)methyl).

Useful (cycloalkenyl)alkyl groups include any of the above-mentioned $C_{1-12}$ alkyl groups, and preferably any of the above-mentioned $C_{1-6}$ alkyl groups, substituted with any of the above-mentioned cycloalkenyl groups (e.g., (cyclobutenyl)methyl, 2-(cyclobutenyl)ethyl, (cyclobutenyl)propyl, (cyclopentenyl)methyl, (cyclohexenyl)methyl, and (cyclopentadienyl)methyl).

Useful aryl groups are $C_{6-14}$ aryl, especially $C_{6-10}$ aryl. Typical $C_{6-14}$ aryl groups include phenyl (Ph), naphthyl, phenanthryl, anthracyl, indenyl, azulenyl, biphenyl, biphenylenyl, and fluorenyl groups, more preferably phenyl, naphthyl, and biphenyl groups.

Useful arylalkyl groups include any of the above-mentioned $C_{1-12}$ alkyl groups, and preferably any of the above-mentioned $C_{1-6}$ alkyl groups, substituted by any of the above-mentioned aryl groups (e.g., benzyl and phenethyl).

Useful arylalkenyl groups include any of the above-mentioned $C_{2-6}$ alkenyl groups substituted by any of the above-mentioned aryl groups (e.g., phenylethenyl).

Useful arylalkynyl groups include any of the above-mentioned $C_{2-6}$ alkynyl groups substituted by any of the above-mentioned aryl groups (e.g., phenylethynyl).

Useful aryloxy groups include oxygen substituted by one of the aryl groups mentioned above (e.g., phenoxy).

Useful aralkyloxy or arylalkoxy groups include oxygen substituted by one of the above-mentioned arylalkyl groups (e.g., benzyloxy).

Useful (arylalkoxy)carbonyl groups include a carbonyl group substituted by any of the above-mentioned arylalkoxy groups (e.g., (benzyloxy)carbonyl).

The terms "heterocycle" and "heterocyclo" are used herein to mean saturated or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. In one embodiment, the 3- to 7-membered monocyclic heterocyclic ring is either a saturated, or unsaturated non-aromatic ring. A 3-membered heterocyclo contains 1 heteroatom, a 4-membered heterocyclo can contain up to 2 heteroatoms, a 5-membered heterocyclo can contain up to 4 heteroatoms, a 6-membered heterocyclo can contain up to 4 heteroatoms, and a 7-membered heterocyclo can contain up to 5 heteroatoms. Each heteroatom is independently selected from nitrogen, which can be quaternized; oxygen; and sulfur, including sulfoxide and sulfone. The 3- to 7-membered heterocyclo can be attached via a nitrogen or carbon atom. A 7- to 10-membered bicyclic heterocyclo contains from 1 to 4 heteroatoms independently selected from nitrogen, which can be quaternized; oxygen; and sulfur, including sulfoxide and sulfone. The 7- to 10-membered bicyclic heterocyclo can be attached via a nitrogen or carbon atom. Examples of the heterocyclic rings include, but are not limited to, pyrrolidinyl, piperidinyl, piperazinyl, morpholinyl, imidazolinyl, pyrazolidinyl, tetrahydrofuranyl, oxazolidinyl, 2-oxooxazolidinyl, tetrahydrothienyl, imidazolidinyl, hexahydropyrimidinyl, and benzodiazepines. In one embodiment, the heterocycle is a 5- or 6-membered heterocycle. Typical 5-membered heterocycle groups include pyrrolidinyl, imidazolinyl, tetrahydrofuranyl, oxazolidinyl, 2-oxaoxazolidinyl, tetrahydrothienyl, and imidazolidinyl. Typical 6-membered heterocycle groups include piperidinyl, piperazinyl, morpholinyl, pyrazolidinyl, and hexahydropyrimidinyl.

Useful (heterocyclo)alkyl or (heterocycle)alkyl groups include any of the above-mentioned $C_{1-10}$ alkyl groups, and preferably any of the above-mentioned $C_{1-6}$ alkyl groups, substituted by any of the above-mentioned heterocyclo or heterocycle groups (e.g., (pyrrolidin-2-yl)methyl, (pyrrolidin-1-yl)methyl, (piperidin-1-yl)methyl, (morpholin-4-yl) methyl, (2-oxooxazolidin-4-yl)methyl, 2-(2-oxooxazolidin-4-yl)ethyl, (2-oxo-imidazolidin-1-yl)methyl, (2-oxo-imidazolidin-1-yl)ethyl, and (2-oxo-imidazolidin-1-yl) propyl).

The term "heteroaryl" as used herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. In one embodiment, the heteroaryl group is a 5- to 10-membered heteroaryl group. In one embodiment, the heteroaryl group is a 5- or 6-membered heteroaryl having 1, 2, or 3 heteroatoms independently selected from O, N, and S. Examples of heteroaryl groups include thienyl, furyl, pyranyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, pyrimidinyl, thiazolyl, isothiazolyl, and isoxazolyl. A 5-membered heteroaryl can contain up to 4 heteroatoms. A 6-membered heteroaryl can contain up to 3 heteroatoms.

As used herein, the term "amino" or "amino group" refers to $—NH_2$.

Useful aminoalkyl groups include any of the above-mentioned $C_{1-112}$ alkyl groups, and preferably any of the above-mentioned $C_{1-6}$ alkyl groups, and more preferably any of the above-mentioned $C_{1-4}$ alkyl groups substituted with one or more amino group.

Useful alkylamino and dialkylamino groups are $—NHR^{13}$ and $—NR^{13}R^{14}$, respectively, wherein $R^{13}$ and $R^{14}$ are each independently selected from a $C_{1-10}$ alkyl group, preferably a $C_{1-6}$ alkyl group, and more preferably a $C_{1-4}$ alkyl group.

As used herein, the term "aminocarbonyl" refers to $C(=O)NH_2$.

Useful alkylcarbonyl groups include a carbonyl group, i.e., —C(=O)—, substituted by any of the above-mentioned $C_{1-10}$ alkyl groups.

Useful arylcarbonyl groups include a carbonyl group substituted by any of the above-mentioned aryl groups (e.g., benzoyl).

Useful alkylcarbonyloxy or acyloxy groups include oxygen substituted by one of the above-mentioned alkylcarbonyl groups.

Useful alkylcarbonylamino or acylamino groups include any of the above-mentioned alkylcarbonyl groups attached to an amino nitrogen, such as methylcarbonylamino.

As used herein, the term "carboxamido" refers to a radical of formula $—C(=O)NR^{15}R^{16}$, wherein $R^{15}$ and $R^{16}$ are each independently hydrogen, optionally substituted $C_{1-10}$ alkyl, or optionally substituted aryl. Exemplary carboxamido groups include $—CONH_2$, $—CON(H)CH_3$, $—CON(CH_3)_2$, and —CON(H)Ph.

As used herein, the term "sulfonamido" refers to a radical of formula $—SO_2NR^{17}R^{18}$, wherein $R^{17}$ and $R^{18}$ are each independently hydrogen, optionally substituted $C_{1-10}$ alkyl, or optionally substituted aryl. Exemplary sulfonamido groups include $—SO_2NH_2$, $—SO_2N(H)CH_3$, and $—SO_2N(H)Ph$.

As used herein, the term "thiol" refers to —SH.

Useful mercaptoalkyl groups include any of the above-mentioned $C_{1-12}$ alkyl groups, and preferably any of the above-mentioned $C_{1-6}$ alkyl groups, substituted by a —SH group.

As used herein, the term "carboxy" refers to —COOH.

Useful carboxyalkyl groups include any of the above-mentioned $C_{1-12}$ alkyl groups, and preferably any of the above-mentioned $C_{1-6}$ alkyl groups, substituted by —COOH.

As used herein, the terms "hydroxyl" or "hydroxy" refer to —OH.

Useful hydroxyalkyl groups include any of the above-mentioned $C_{1-12}$ alkyl groups, preferably any of the above-mentioned $C_{1-6}$ alkyl groups, and preferably any of the above-mentioned $C_{1-4}$ alkyl groups, substituted by one or more hydroxy groups. Representative hydroxy($C_{1-6}$)alkyl groups include hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methyl propyl, and 1,3-dihydroxyprop-2-yl.

As used herein, the term "cyano" refers to —CN.

As used herein, the term "nitro" refers to $—NO_2$.

As used herein, the term "ureido" refers to $—NH—C(=O)—NH_2$.

As used herein, the term "azido" refers to $—N_3$.

The term "ambient temperature" as used herein means the temperature of the surroundings. The ambient temperature indoors is the same as room temperature, which is from about 20° C. to about 25° C.

The term "about," as used herein in connection with a measured quantity, refers to the normal variations in that measured quantity, as expected by the skilled artisan making the measurement and exercising a level of care commensurate with the objective of measurement and the precision of the measuring equipment. Typically, the term "about" includes the recited number±10%. Thus, "about 10" means 9 to 11.As used herein, the term "optionally substituted" refers to a group that may be unsubstituted or substituted.

Optional substituents on optionally substituted groups, when not otherwise indicated, include one or more groups, typically 1, 2, or 3 groups, independently selected from the group consisting of halo, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$) alkyl, aryl($C_{2-6}$)alkenyl, aryl($C_{2-6}$)alkynyl, cycloalkyl($C_{1-6}$) alkyl, heterocyclo($C_{1-6}$)alkyl, hydroxy($C_{1-6}$)alkyl, amino ($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, aryloxy, ar($C_{1-6}$)alkyloxy, carboxamido, sulfonamido, azido, $C_{1-6}$ alkoxy, halo($C_{1-6}$)alkoxy, carboxy, aminocarbonyl, (=O), and mercapto($C_{1-6}$)alkyl groups mentioned above. Preferred optional substituents include halo, halo($C_{1-6}$)alkyl, hydroxy($C_{1-6}$)alkyl, amino($C_{1-6}$)alkyl, hydroxy, nitro, $C_{1-6}$ alkyl, $C_{1-6}$ alkoxy, halo($C_{1-6}$)alkoxy, and amino.

Compounds of the Disclosure encompass all the salts of the compounds of any of Formulae I-VI. The present invention preferably includes all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

Compounds of the Disclosure also encompass solvates of any of the compounds of Formulae I-VI. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure may be present as solvated forms with a pharmaceutically acceptable solvent, such as water, methanol, ethanol, and the like, and it is intended that the invention includes both solvated and unsolvated forms of compounds of any of Formulae I-VI. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1): Article 12 (2004), and A. L. Bingham et al., *Chem. Commun.:* 603-604 (2001). A typical, non-limiting, process of preparing a solvate would involve dissolving a compound of any of Formulae I-VI in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of the Disclosure can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, and preferably $^{3}H$, $^{11}C$, and $^{14}C$. Isotopically-labeled Compounds of the Invention can be prepared by methods known in the art in view of this disclosure. For example, tritiated Compounds of the Disclosure can be prepared by introducing tritium into the particular compound by catalytic dehalogenation with tritium. This method may include reacting a suitable halogen-substituted precursor of a Compound of the Disclosure with tritium gas in the presence of an appropriate catalyst such as Pd/C in the presence of a base. Other suitable methods for preparing tritiated compounds can be found in Filer, *Isotopes in the Physical and Biomedical Sciences, Vol.* 1, *Labeled Compounds* (*Part A*), Chapter 6 (1987). $^{14}C$-labeled compounds can be prepared by employing starting materials having a $^{14}C$ carbon.

Isotopically labeled Compounds of the Disclosure, as well as the pharmaceutically acceptable salts and solvates thereof, can be used as radioligands to test for the binding of compounds to an opioid receptor. For example, a radio-labeled Compound of the Disclosure can be used to characterize specific binding of a test or candidate compound to the receptor. Binding assays utilizing such radio-labeled compounds can provide an in vitro alternative to animal testing for the evaluation of chemical structure-activity relationships. For example, the receptor assay may be performed at a fixed concentration of a radiolabeled Compound of the Disclosure and at increasing concentrations of a test compound in a competition assay. In a non-limiting embodiment, the present invention provides a method for screening a candidate compound for the ability to bind to an opioid receptor, comprising a) introducing a fixed concentration of a radio-labeled Compound of the Disclosure to the receptor under conditions that permit binding of the radio-labeled compound to the receptor to form a complex; b) titrating the complex with a candidate compound; and c) determining the binding of the candidate compound to said receptor.

Some of the compounds disclosed herein may contain one or more asymmetric centers and may thus give rise to enantiomers, diastereomers, and other stereoisomeric forms, such as epimers. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centres present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

Open terms such as "include," "including," "contain," "containing" and the like mean "comprising."

The term "an effective amount" or "a therapeutically effective amount" of a Compound of the Disclosure refers to an amount of the Compound of the Disclosure that is capable of delivering a therapeutically effective dosage of the parent opioid when administered as directed.

Suitable hydroxyl protecting groups for PG are well known and include, for example, any suitable hydroxyl protecting group disclosed in Wuts, P. G. M. & Greene, T. W., *Greene's Protective Groups in Organic Synthesis,* 4rd Ed., pp. 16-430 (J. Wiley & Sons, 2007), herein incorporated by reference in its entirety. The term "hydroxyl protecting group" as used herein refers to a group that blocks (i.e., protects) the hydroxy functionality while reactions are carried out on other functional groups or parts of the molecule. Those skilled in the art will be familiar with the selection, attachment, and cleavage of protecting groups and will appreciate that many different protective groups are known in the art, the suitability of one protective group or another being dependent on the particular synthetic scheme planned. Suitable hydroxy protecting groups are generally able to be selectively introduced and removed using mild reaction conditions that do not interfere with other portions of the subject compounds. These protecting groups can be introduced or removed at a convenient stage using methods known in the art. The chemical properties of such groups, methods for their introduction and removal are known in the art and can be found, for example, in Greene, T. W. and Wuts, P. G. M., above. Additional hydroxyl protecting groups can be found, for example, in U.S. Pat. No. 5,952,495, U.S. Patent Appl. Pub. No. 2008/0312411, WO 2006/035195, and WO 98/02033, which are herein incorporated by reference in their entireties. Suitable hydroxyl protecting groups include the methoxymethyl, tetrahydropyranyl, tert-butyl, allyl, tert-butyldimethylsilyl, tert-butyldiphenylsilyl, acetyl, pivaloyl, benzoyl, benzyl (Bn), and p-methoxybenzyl group.

As used herein, the term "delaying the onset" or "delayed onset" refers to the increased time to onset of therapeutic action post-administration provided by certain Compounds of the Disclosure, when act as prodrugs, as compared to the corresponding amount of the parent compounds (e.g., the intended biologically active moieties) during the same length of time via the same route of administration.

As used herein, the terms "decrease the abuse potential," "decreased abuse potential," and the like refer to the reduced potential of certain Compounds of the Disclosure for improper non-medical and/or recreational administration as compared to the parent compounds, yet wherein the compounds are still capable of delivering desired therapeutic effects when administered as directed.

Use of phrases such as "decreased," "reduced," "diminished," or "lowered" in relation to abuse potential or overdose potential refer to at least about a 10% decrease in abuse potential or overdose potential as measured by one or more standard measures of such abuse potential or overdose as known in the art, with greater percentage changes being preferred for reduction in abuse potential and overdose potential. For instance, the decrease can be greater than 25%, 35%, 45%, 55%, 65%, 75%, 85%, 95%, 96%, 97%, 98%, or 99%.

As used herein, the term "opioid" refers to a compound that binds to an opioid receptors, in particular to the μ (mu), κ (kappa), δ (delta) and ORL1 receptor. Opioid compounds for use in the present application include both opioid agonists, opioid partial agonists, and opioid antagonists, such as oxycodone, hydromorphone, oxymorphone, buprenorphine, and hydrocodone. In one embodiment, the opioid compound (or the parent compound) for use in the present application is oxycodone or hydrocodone. In another embodiment, the opioid compound (or the parent compound) is oxycodone.

As used herein, compounds that bind to receptors and mimic the regulatory effects of endogenous ligands are defined as "agonists". Compounds that bind to receptors and are only partly effective as agonists are defined as "partial agonists". Compounds that bind to a receptor but produce no regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics,* $10^{th}$ Ed. (J. G. Hardman, L. E. Limbird and A. Goodman-Gilman eds., 2001)).

As used herein, the term "opioid therapy" refers to administration of an opioid to a subject for treatment or prophylaxis of a condition that an opioid compound has been proven to be effective in treating, ameliorating, or preventing.

In a certain embodiment, the opioid therapy is for pain management (e.g., treating, ameliorating, or preventing pain). In another embodiment, the opioid therapy is for treatment, prevention or attenuation of opioid-induced adverse pharmacodynamic responses, such as, euphoria, bowel dysfunction (e.g., constipation, decreased gastric emptying, abdominal cramping, spasm, bloating, delayed gastro-intestinal transit), nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance. In a separate embodiment, the opioid therapy can be used for the treatment of diarrhea, cough, anxiety (e.g., due to shortness of breath) and opioid dependence. In still another embodiment, the opioid therapy is useful for the treatment, prevention, or attenuation of opioid withdrawal.

As used herein, the term "Oxy" refers to oxycodone.

Synthesis of Compounds of the Disclosure

Compounds of the Disclosure can be prepared using methods known to those skilled in the art in view of this disclosure, or by illustrative methods shown in the schemes below. For example, Compounds of the Disclosure can be prepared as shown in Scheme A and Scheme B below. Additional methods of synthesis are described and illustrated in the working examples set forth below.

Scheme A

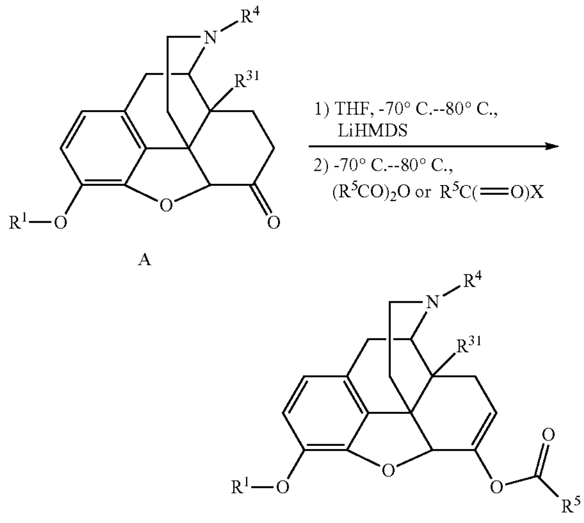

A

IV

Compounds of Formula IV, where $R^{31}$ is hydrogen or OH, and $R^1$, $R^4$ and $R^5$ are as defined above for Formula I, can be prepared by mixing compound A, wherein $R^{31}$ is hydrogen or OH, and $R^1$ and $R^4$ are as defined for Formula I, first with lithium bis(trimethylsilyl)amide at from about −70° C. to about −80° C., and preferably at about −78° C., in a suitable polar, aprotic solvent, such as tetrahydrofuran (THF). The reaction mixture is then allowed to warm to room temperature and stirring is continued at room temperature from about 30 minutes to about 1 hour. The reaction is mixture is then re-chilled to the temperature of from about −70° C. to about −80° C., and preferably to about −78° C., and a suitable acid anhydride of formula $(R^5CO)_2O$ or a reagent of formula $R^5C(=O)X$ is added to the mixture, wherein $R^5$ is as defined above for Formula I and X is a suitable leaving group, such as Cl.

In another embodiment, compounds of Formula IV where $R^{31}$ is hydrogen are prepared by the method of Scheme A. In another embodiment, compounds of Formula IV where $R^{31}$ is OH are prepared by the method of Scheme A.

In another embodiment, in the Scheme A, compound A is oxycodone. In another embodiment, the acid anhydride in step 2) is acetic anhydride to obtain 6-acetyl oxycodone.

Compounds of Formula I, where $R^2$ is —C(=O)$R^5$ and $R^3$ is —OC(=O)$R^6$, wherein $R^5$ and $R^6$ are the same and are as defined above for Formula I, can be prepared as shown in Scheme B below to obtain compounds of Formula V.

Scheme B

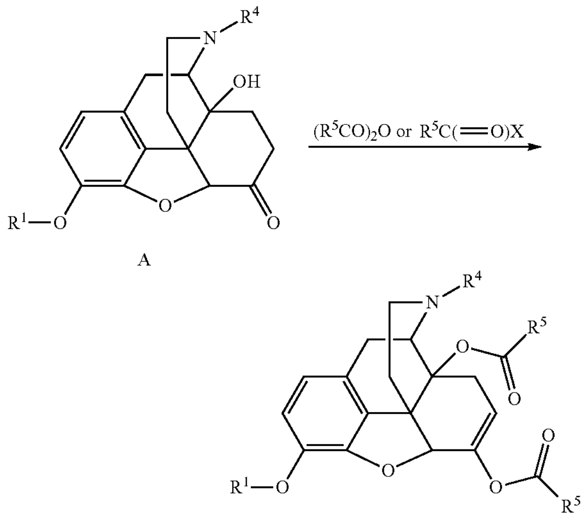

A

V

In the Scheme B, $R^1$, $R^4$, and $R^5$ are as defined above for Formula I. Accordingly, compounds of Formula V can be prepared by reacting compound B with a suitable acid anhydride of formula $(R^5CO)_2O$ or a reagent of formula $R^5C(=O)X$, where X is a suitable leaving group, such as Cl.

Compounds of any one of Formulae I-III including a substituent comprising PEG can be prepared, for example, as described in WO 2011/088140.

In some non-limiting embodiments, the compounds of Formulae I-VI are converted to their salts using techniques commonly known to a person of ordinary skill in the art. In other embodiments, the salt is a pharmaceutically acceptable salt.

Administration of Compounds of the Disclosure

Compounds of the Disclosure can act as prodrugs and thereby exhibit one or more advantages over the parent opioid drug. For example, Compounds of the Disclosure can be used to prevent accidental overdose by exhibiting a delayed onset of pharmacological activity when inadvertently orally administered at higher than the prescribed dose. In some embodiments, Compounds of the Disclosure can hinder abuse by substantially maintaining their chemical form as prodrugs when administered by non-oral routes (e.g., parenteral) likely to be employed by abusers. Thus, Compounds of the Disclosure can hinder abuse by reducing extractability and solubility in an aqueous or alcohol medium, and thereby reducing availability of the active opioid molecule when administered via parenteral routes, particularly the intravenous, intranasal, and/or inhalation routes that are often employed in illicit use.

In some embodiments, Compounds of the Disclosure have little affinity, or have different affinity, for the μ opioid receptor as compared to that of the parent opioid. Compounds of the Disclosure cannot be converted from the prodrug form to the parent opioid under the acid conditions of the stomach. Instead, Compounds of the Disclosure can be converted from the prodrug form to the parent opioid under the conditions in the intestines via enzyme-assisted hydrolysis. Gradual conversion of a Compound of the Disclosure to the parent opioid when administered orally to a mammal should result in gradual but delayed systemic exposure to the parent opioid, as compared to direct oral administration of the parent opioid.

An opioid prodrug that provides a gradual conversion to the parent opioid can be less attractive to substance abusers or non-medical recreational users of opioids who seek drugs to provide rapid euphoria. As conversion from a Compound of the Disclosure to the parent opioid will be slower, the onset of euphoria will likewise be slower, thereby resulting in compounds of the invention appearing less attractive to those who would attempt such non-medical usage of the drug.

In many cases, opioid abuse by the oral route involves immediate release drugs, or drugs in which controlled release materials used to delay the liberation and absorption of the opioid from the dosage form have been tampered with. Immediate release opioids generally provide pharmacologically relevant plasma concentrations, onset of therapeutic effects and, in the case of recreational drug users, onset of euphoria, within about 15 to 180 minutes, 15 to 120 minutes, or 15 to 90 minutes after oral administration.

The gradual conversion of compounds of the invention to the parent opioid in the GI tract may serve to delay, and therefore reduce, any euphoric effects otherwise produced by opioids by delaying the time to reach pharmacologically relevant plasma concentrations of oxycodone, e.g., by providing a lower $C_{max}$ and/or a later $T_{max}$ than oral, immediate release forms of opioids. Consequently, in some embodiments, dosage forms of the present invention will have a lower potential for abuse and misuse.

In certain embodiments, pharmaceutical compositions containing a Compound of the Disclosure can achieve an extended release profile of a pharmaceutically active ingredient (e.g., an opioid analgesic). For example, when administered orally, a compound of the invention may be slowly converted to the parent opioid compound in a patient's GI tract. In such circumstances, such pharmaceutical compositions are considered as extended release formulation.

An extended release formulation prevents rapid onset of pharmacological effects, and is formulated in such a manner as to make the pharmaceutically active ingredient available over an extended period of time. In some embodiments, a Compound of the Disclosure can achieve an extended release profile simply based on the fact that it requires conversion to the parent opioid. Thus, in one embodiment, Compounds of the Disclosure can be formulated without use of controlled release excipients, yet still result in an extended release of opioid upon oral administration.

Extended release formulations can further include formulation features, for example, by incorporating a sustained release matrix or a sustained release coating, or some variation thereof, to achieve an enhanced extended release profile of the parent opioid compound(s). Controlled release formulation technology is well-known in the art, and can be used in conjunction with the present invention to obtain particularly desirable release profiles. In some embodiments, both the parent opioid and the Compound(s) of the Disclosure can be combined into a single oral dosage form, where the opioid provides an immediate release profile and the compound(s) of the invention effectively provides an extended release profile of oxycodone. Such combination formulations may or may not further comprise a sustained release matrix or a sustained release coating, or some variation thereof.

The present disclosure further provides a method of treating pain in a mammal (e.g., a human patient) identified in need thereof, the method comprising administering to the mammal an effective amount of a Compound of the Disclosure. In certain embodiments, the Compound of the Disclosure is administered orally to the mammal.

In one embodiment, the present disclosure provides a method of decreasing the abuse potential of an opioid in a mammal in need of opioid therapy, the method comprising orally administering to the mammal an effective amount of a Compound of the Disclosure, which exhibits a decreased parenteral (i.e., non-oral) bioavailability compared to the parent opioid.

In another embodiment, the present disclosure provides a method of decreasing the abuse potential of oxycodone in a mammal in need of oxycodone therapy, the method comprising orally administering to the mammal an effective amount of a compound of any one of Formulae II to V, or a pharmaceutically acceptable salt or solvate thereof, wherein $R^1$ is $CH_3$, $R^3/R^{31}$ is OH, $R^4$ is $CH_3$, and $R^2$ is —C(=O)$R^5$, and $R^5$ is as defined above for Formula II. In another embodiment, the method comprises administering a compound selected from the group consisting of

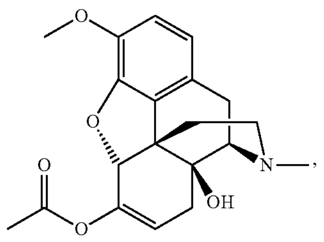

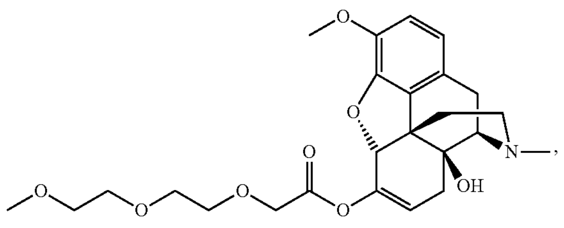

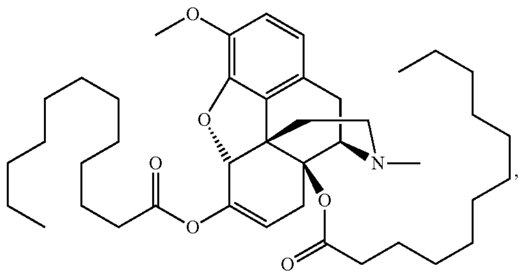

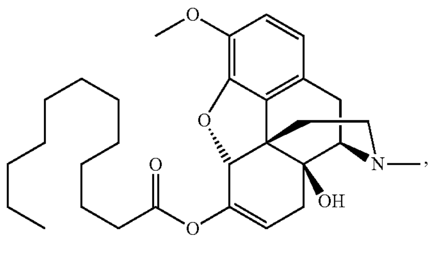

-continued

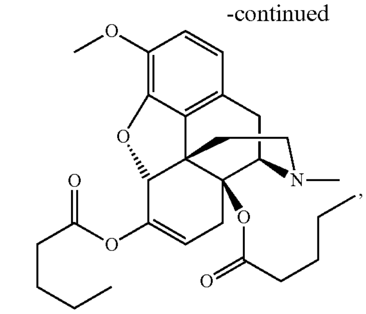

, and

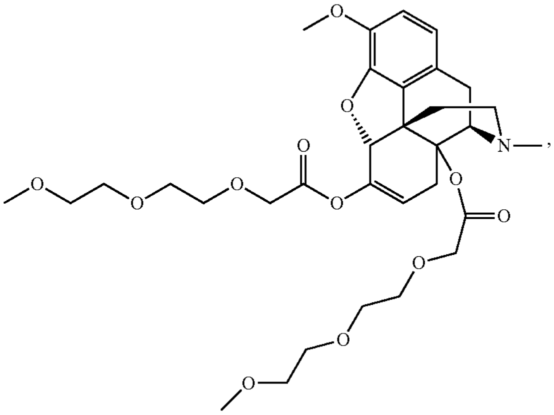

, or a pharmaceutically acceptable salt or solvate thereof. In another embodiment, 6-acetyl oxycodone, or a pharmaceutically acceptable salt or solvate thereof, is administered.

In another embodiment, the present disclosure provides a method of treating pain with reduced abuse potential of oxycodone in a mammal in need of oxycodone therapy, the method comprising orally administering to the mammal an effective amount of a compound of Formula VI, or a pharmaceutically acceptable salt or solvate thereof, wherein $R^1$ is $CH_3$, $R^4$ is $CH_3$, and $R^3$ is —OC(═O)$R^6$, and $R^6$ is as defined above for Formula I. In another embodiment, the method comprises administering a compound

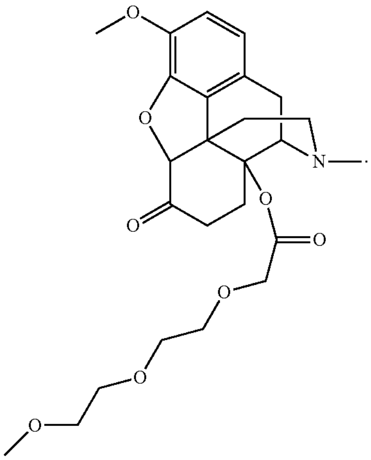

.

In another embodiment, the present disclosure provides a method of treating pain with reduced abuse potential of oxymorphone in a mammal in need of oxymorphone therapy, the method comprising orally administering to the mammal an effective amount of a compound of Formula II or Formula III, or a pharmaceutically acceptable salt or solvate thereof, wherein in the compound of Formula II or Formula III, $R^1$ is hydrogen, $R^3$ is OH, $R^4$ is $CH_3$, and $R^2$ is C(═O)$R^5$, and $R^5$ is as defined above for Formula II. Alternatively, an effective amount of a compound of Formula IV is administered, or a pharmaceutically acceptable salt or solvate thereof, wherein $R_1$ is hydrogen, $R^{31}$ is OH, $R^4$ is methyl, and $R^5$ is as defined above for Formula II.

In one embodiment, the present disclosure provides a method of treating pain with reduced abuse potential of hydrocodone in a mammal in need of hydrocodone therapy, the method comprising orally administering to the mammal an effective amount of a compound of any of Formulae II to IV, or a pharmaceutically acceptable salt or solvate thereof, wherein $R^1$ is $CH_3$, $R^3/R^{31}$ is H, $R^4$ is $CH_3$, and $R^2$ is —C(═O)$R^5$, and $R^5$ is a defined above for Formula II, provided that the compound is not

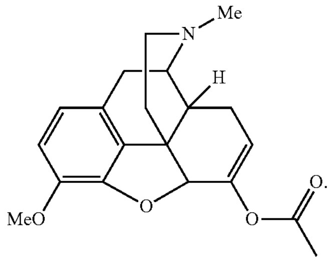

In one embodiment, the present disclosure provides a method of treating pain with decreased abuse potential of hydromorphone in a mammal in need of hydromorphone therapy, the method comprising orally administering to the mammal an effective amount of a compound of any one of Formulae II to IV, or a pharmaceutically acceptable salt or solvate thereof, wherein $R^1$ is H, $R^3$ or $R^{31}$ is H, $R^4$ is $CH_3$, and $R^2$ is —(═O)$R^5$, and $R^5$ is as defined above for Formula II, provided that the compound is not

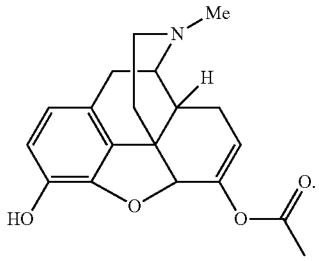

In one embodiment, the present disclosure provides a method of decreasing the abuse potential of a parent opioid compound, comprising orally administering to the mammal an effective amount of a compound of any one of Formulae I to VI, or a pharmaceutically acceptable salt or solvate thereof, with the proviso that 1) the compound is not

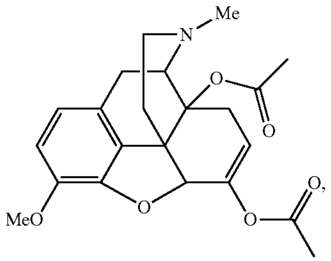

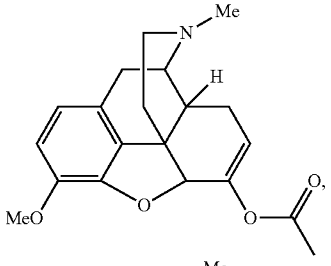

or

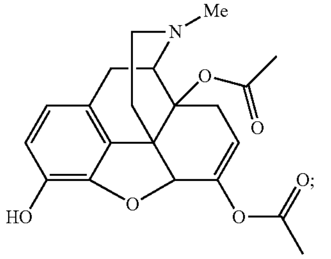

2) when $R^1$ is unsubstituted alkyl, $R^3$ is hydrogen, and $R^4$ is unsubstituted $C_{1-6}$ alkyl, then $R^5$ is other than optionally substituted phenyl or optionally substituted pyridyl; or 3) when $R^1$ is unsubstituted alkyl, $R^4$ is unsubstituted $C_{1-6}$ alkyl, and $R^3$ is —OC(=O)$R^6$, then both $R^5$ and $R^6$ are other than optionally substituted pyridyl. In one embodiment, the present disclosure provides a method of decreasing the abuse potential of a parent opioid compound, comprising orally administering to the mammal an effective amount of a compound of any one of Formulae I to VI, or a pharmaceutically acceptable salt or solvate thereof, with the proviso that the compound is not

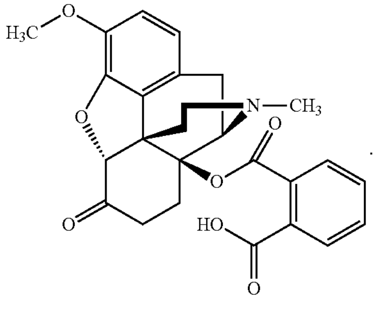

.

In one embodiment, the invention is a method of achieving an opioid therapy in a mammal in need of such therapy (e.g., for treating pain), comprising orally administering to the mammal a therapeutically effective amount of a compound of any one of Formulae I to VI, or a pharmaceutically acceptable salt or solvate thereof, wherein at least about 10%, at least about 20%, at least about 30%, at least about 40%, at least about 50%, at least about 60%, at least about 70%, at least about 80%, at least about 90%, or about 100% of the compound of any one of Formulae I to VI, or the pharmaceutically acceptable salt or solvate thereof, is hydrolyzed to the parent opioid within about 2 hours at 37° C. in intestinal fluid at pH 6.8 in the presence of pancreatin.

In one embodiment, the invention is a method of achieving oxycodone therapy in a mammal in need of said therapy, comprising orally administering to the mammal a therapeutically effective amount of a compound of any one of Formulae II to IV, or pharmaceutically acceptable salt or solvate thereof, wherein in the compound of Formulae II to IV, $R^1$ is $CH_3$, $R^3$/$R^{31}$ is OH, $R^4$ is $CH_3$, and $R^2$ is —C(=O)$R^5$, and $R^5$ is as defined above for Formula II, wherein at least about 10%, at least about 20%, at least about 30%, at least about 40%, or at least about 50% of the compound of any one of Formulae II to IV or salt or solvate thereof is hydrolyzed to oxycodone within about 2 hours at 37° C. in intestinal fluid at pH 6.8 in the presence of pancreatin.

In a particular embodiment, the method comprises orally administering to the mammal a therapeutically effective amount of a compound of any one of Formulae II to IV, or pharmaceutically acceptable salt or solvate thereof, wherein in the compound of Formulae II to IV, $R^1$ is $CH_3$, $R^3$/$R^{31}$ is OH, $R^4$ is $CH_3$, and $R^2$ is —C(=O)$R^5$, and $R^5$ is as defined above for Formula II, wherein at least about 10%, at least about 20%, at least about 30%, at least about 40%, at least about 50%, at least about 60%, at least about 70%, at least about 90%, or about 100% of the compound of any one of Formulae II to IV, or salt or solvate thereof is hydrolyzed to oxycodone within about 2 hours at 37° C. in intestinal fluid at pH 6.8 in the presence of pancreatin.

In one embodiment, the method comprises orally administering 6-acetyl oxycodone, or pharmaceutically acceptable salt thereof, wherein about 80%, about 90%, about 95%, or about 100% of 6-acetyl oxycodone or a salt thereof is hydrolyzed to oxycodone within about 2 hours at 37° C. in intestinal fluid at pH 6.8 in the presence of pancreatin.

In another embodiment, the present disclosure provides a method of decreasing the abuse potential of oxycodone in a mammal in need of oxycodone therapy, the method comprising orally administering to the mammal an effective amount of a compound of Formula VI, or a pharmaceutically acceptable salt or solvate thereof, wherein $R^1$ is $CH_3$, $R^4$ is $CH_3$, and $R^3$ is —OC(=O)$R^6$, and $R^6$ is as defined above for Formula I, wherein at least about 10%, at least about 20%, at least about 30%, at least about 40%, or at least about 50% of the compound of Formula VI or salt or solvate thereof is hydrolyzed to oxycodone within about 2 hours at 37° C. in intestinal fluid at pH 6.8 in the presence of pancreatin.

In some embodiments, the compound of any one of Formulae I to VI, or a pharmaceutically acceptable salt or solvate thereof, provides bioavailability of the parent opioid by any parenteral route (for example, intravenous, intranasal, or inhalation) of less than about 70%, less than about 50%, less than about 30%, less than about 20%, less than about 15%, less than about 10%, less than about 5%, less than about 4%, less than about 3%, less than about 2%, or less than about 1% of the bioavailability of the parent opioid administered by the same route.

In other embodiments, the present disclosure provides extended release formulations of oxycodone, comprising an effective amount of

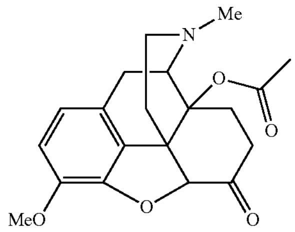
, or a pharmaceutically acceptable salt or solvate thereof, together with one or more pharmaceutically acceptable excipients or carriers thereof. The extended release formulations of oxycodone may further include oxycodone or a pharmaceutically acceptable salt or solvate thereof in either an immediate release form or an extended release form or both. The present disclosure further provides methods of use of such extended release formulations of oxycodone, such as, a method for treating pain or a method of reducing the abuse potential of an opioid in a mammal in need of opioid therapy.

Compounds of the Disclosure exhibit a relatively high degree of stability, that is, resistance to hydrolysis, when subject to "kitchen chemistry" which might be used by a potential abuser.

6-Substituted Enol Esters and Their Use a Prodrugs

The inventors have found that certain 6-substituted enol esters of Formula IV, as defined above, are μ-opioid receptor agonists and can also be used as prodrugs, i.e., they can be used for the same purpose as their parent opioid compounds. These compounds are thus analgesic compounds when made bioavailable from a dosage form, such as, for example, a transdermal, subcutaneous, intramuscular, intravenous, or parenteral dosage form. When these 6-substituted enol esters are orally administered to a patient, they convert to the parent opioid, such as oxycodone, in some parts of the gastrointestinal tract of the patient. Thus, within a certain time post oral administration, the formulation containing the certain 6-substituted enol esters may provide μ-opioid agonist functions from both the prodrug of Formula IV and the parent opioid.

In this aspect of the invention, the disclosure provides the following particular embodiments.

{Ia}. A compound of Formula IV:

IV

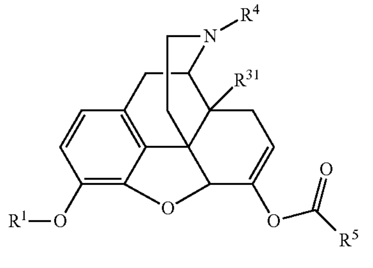

or a pharmaceutically acceptable salt or solvate thereof, wherein

R', $R^4$, and $R^5$ are as defined for Formula I or Formula II above, and $R^{31}$ is hydrogen or OH.

{IIa}. The compound of {Ia}, or a pharmaceutically acceptable salt or solvate thereof, wherein $R^1$ is H; $C_{1-6}$ alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl;

$R^5$ is selected from the group consisting of unsubstituted $C_{1-12}$ alkyl, unsubstituted $C_{2-12}$ alkenyl, unsubstituted $C_{2-12}$ alkynyl, $-CH_2-O-(CH_2CH_2O)_m-R^7$, $-O-(CH_2CH_2O)_n-R^7$, and $-NH-(CH_2CH_2O)_p-R^7$;

$R^7$ is selected from the group consisting of hydrogen and $C_{1-6}$ alkyl;

m is an integer between 1 and 9;

n and p are each independently an integer between 1 and 20; and

PEG is one ethylene oxide unit or an oligomer of 2 to about 10 ethylene oxide subunits, provided that the compound is not

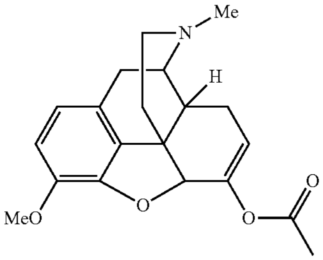 [SMILES: COc1ccc2c3c1OC1C(OC(C)=O)=CCC4C(C2)N(C)CCC314]
or

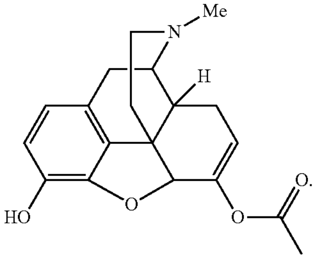 [SMILES: CC(=O)OC1=CCC2C3Cc4ccc(O)c5c4C2(CCN3C)C1O5]

{IIIa}. The compound of claim {IIa}, or a pharmaceutically acceptable salt or solvate thereof, wherein $R^1$ is H or unsubstituted $C_{1-6}$ alkyl and $R^4$ is unsubstituted $C_{1-6}$ alkyl.

{IVa}. The compound of claim {IIa} or {IIIa}, or a pharmaceutically acceptable salt thereof, wherein $R^3$ is OH.

{Va}. The compound of any one of {IIa}-{IVa}, or a pharmaceutically acceptable salt or solvate thereof, wherein $R^1$ and $R^4$ are methyl.

{VIa}. The compound of any one of {IIa}-{Va}, or a pharmaceutically acceptable salt thereof, wherein $R^5$ is unsubstituted $C_{1-6}$ alkyl.

{VIIa}. The compound of any one of {IIa}-{VIa}, or a pharmaceutically acceptable salt thereof, wherein $R^5$ is methyl.

{VIIIa}. The compound of any one of {IIa}-{Va}, or a pharmaceutically acceptable salt thereof, wherein $R^5$ is unsubstituted $C_{7-12}$ alkyl.

{IXa}. The compound of any one of {IIa}-{Va} and {VIIIa}, or a pharmaceutically acceptable salt thereof, wherein $R^5$ is unsubstituted heptyl, octyl, or nonyl.

{Xa}. The compound of any one of {IIa}-{Va} and {VIIIa}, or a pharmaceutically acceptable salt thereof, wherein $R^5$ is unsubstituted decyl, undecyl, or dodecyl.

{XIa}. The compound of {Xa}, or a pharmaceutically acceptable solvate thereof, wherein $R^5$ is undecyl.

{XIIa}. The compound of any one of {IIa}-{Va}, or a pharmaceutically acceptable salt thereof, wherein $R^5$ is selected from the group consisting of $-CH_2-O-(CH_2CH_2O)_m-R^7$, $-O-(CH_2CH_2O)-R^7$, and $-NH-(CH_2CH_2O)_p-R^7$;

$R^7$ is hydrogen or $C_{1-4}$ alkyl;

m is 1, 2, 3, 4, or 5;

n and p are each independently selected from the group consisting of 1, 2, 3, 4, 5, 6, 7, 8, 9, and 10.

{XIIIa}. The compound of any one of {IIa}-{Va} and {XIIa}, or a pharmaceutically acceptable salt thereof, wherein $R^7$ is hydrogen or methyl.

{XIVa}. The compound of any one of {IIa}-{Va} and {XIIa}, or a pharmaceutically acceptable salt thereof, wherein $R^5$ is $-CH_2-O-(CH_2CH_2O)_m-R^7$.

{XVa}. The compound of any one of {IIa}-{Va} and {XIIa}-{XIVa}, or a pharmaceutically acceptable salt thereof, wherein m is 1, 2, or 3.

{XVIa}. The compound of {XVa}, or a pharmaceutically acceptable salt thereof, wherein m is 2.

{XVIIa}. The compound of any one of {XIVa}-{XVIa}, or a pharmaceutically acceptable salt or solvate thereof, wherein $R^7$ is methyl.

{XVIIIa}. The compound of any one of {Ia} and {IIa}-{VIIa}, which is

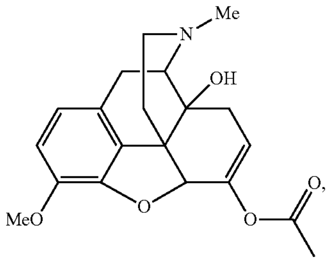 [SMILES: COc1ccc2c3c1OC1C(OC(C)=O)=CCC4(O)C(C2)N(C)CCC314]

or a pharmaceutically acceptable salt or solvate thereof.

{XIXa}. The compound of {XVIIIa}, which is

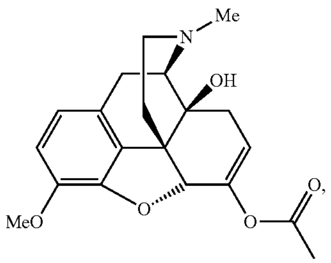

or a pharmaceutically acceptable salt or solvate thereof.

{XXa}. The compound of {IIa}, which is

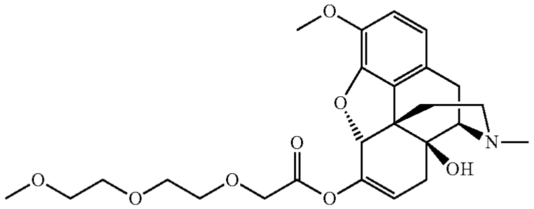

or

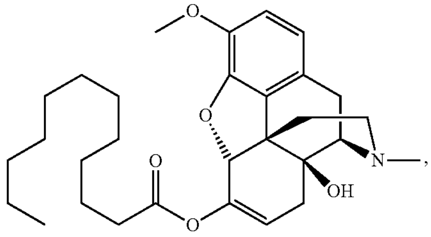

or a pharmaceutically acceptable salt or solvate thereof.

{XXIa}. A pharmaceutical composition, comprising a compound of any one of {Ia}-{XXa}, or a pharmaceutically acceptable salt thereof, and one or more pharmaceutically acceptable carriers.

{XXIIa}. A composition, comprising one or more compounds of {Ia}-{XXa}, or a pharmaceutically acceptable salt or solvate thereof, and at least one parent opioid.

{XXIIIa}. The composition of {XXIIa}, comprising from about 0.1 to about 30 wt % of the at least one parent opioid.

{XXIVa}. The composition of {XXIIa} or {XXIIIa}, comprising from about 1 to about 20 wt % of the at least one parent opioid.

{XXVa}. The composition of any one of {XXIIa}-{XXIVa}, wherein the at least one parent opioid is oxycodone.

{XXVIa}. An oral formulation, comprising a therapeutically effective amount of a composition of any one of {XXIIa}-{XXVa}.

{XXVIIa}. A method of treating or preventing a disorder responsive to the modulation of one or more opioid receptors in a patient, comprising administering to the patient in need of such treatment or prevention an effective amount of a compound of any one of {Ia}-{XXa}, or a pharmaceutically acceptable salt or solvate thereof.

{XXVIIIa}. The method of {XXVIIa}, wherein the disorder is pain.

{XXIXa}. A method of treating, ameliorating or preventing pain in a patient, comprising administering an effective amount of a compound of any one of {Ia}-{XXa}, or a pharmaceutically acceptable salt or solvate thereof, to the patient in need of such treatment, amelioration, or prevention.

{XXXa}. The method of {XXIXa}, wherein the method is for treating pain.

{XXXIa}. The method of {XXXa}, wherein said pain is acute pain, chronic pain, or surgical pain.

{XXXIIa}. The method of {XXXIa}, wherein said pain is chronic pain.

{XXXIIIa}. The method of {XXXIIa}, wherein said chronic pain is neuropathic pain, postoperative pain, or inflammatory pain.

{XXXIVa}. A method of slowing the onset of activity of an opioid in a mammal in need of opioid therapy, comprising orally administering to the mammal a therapeutically effective amount of the compound or a mixture of the compounds according to any one of {Ia}-{XXa}, or a pharmaceutically acceptable salt or solvate thereof.

{XXXVa}. A method of treating a disorder responsive to the modulation of one or more opioid receptors in a mammal in need of opioid therapy with delayed onset of opioid activities, comprising orally administering to the mammal a therapeutically effective amount of the compound or a mixture of the compounds according to any one of {Ia}-{XXa}, or a pharmaceutically acceptable salt or solvate thereof. In certain embodiments, the method further includes one or more parent opioid compounds, wherein the total amount of the Compounds of the Disclosure and the parent opioid compounds accounts for the therapeutically effective amount.

{XXXVIa}. The method of {XXXIVa} or {XXXVa}, further comprising co-administering one or more other therapeutic agents.

{XXXVIIa}. The method of {XXXVIa}, wherein said one or more other therapeutic agents are one or more non-steroidal anti-inflammatory agents.

{XXXVIIIa}. The method of {XXXVIa}, wherein said one or more other therapeutic agents are one or more opioid agonists.

{XXXIXa}. The method of {XXXVIa}, wherein said one or more other therapeutic agents are one or more opioid antagonists.

Short Chain 14-Substituted Enol Esters and Their Use as Prodrugs

The inventors have found that certain 14-substituted enol esters of Formula VI, having a short chain substituent at the 14-position, act as μ-opioid receptor agonists and can be used as prodrugs. These compounds are thus analgesic compounds when made bioavailable from a dosage form, such as, for example, a transdermal, subcutaneous, intramuscular, intravenous, or parenteral dosage form. When the prodrugs orally delivered to a patient and are made bioavailable only in the lower gastrointestinal tract of the patient, they convert to the parent opioid, such as oxycodone, within a certain time to provide μ-opioid agonist functions from both the prodrug of Formula VI and the parent opioid.

In this aspect of the invention, the disclosure provides the following particular embodiments.

{Ib}. A compound of Formula VI:

VI

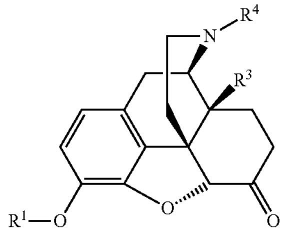

or a pharmaceutically acceptable salt or solvate thereof, wherein:

$R^1$ is H; $C_{1-6}$ alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl;

$R^3$ is —OC(═O)$R^6$, wherein $R^6$ is selected from the group consisting of unsubstituted $C_{1-4}$ alkyl, unsubstituted $C_{2-4}$ alkenyl, unsubstituted $C_{2-4}$ alkynyl, or —$CH_2$—O—$(CH_2CH_2O)_m$—$R^7$;

m is 1;

$R^7$ is selected form the group consisting of hydrogen and $C_{1-6}$ alkyl; and PEG is one ethylene oxide unit or an oligomer of 2 to about 10 ethylene oxide subunits, provided that the compound is not

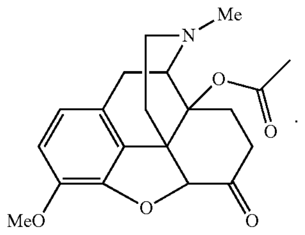 [SMILES: COc1ccc2c3c1OC1C(=O)CCC4(OC(C)=O)C(C2)N(C)CCC314]

{IIb}. The compound of {Ib}, or a pharmaceutically acceptable salt or solvate thereof, wherein $R^6$ is unsubstituted methyl, ethyl, propyl, or butyl.

{IIIb}. The compound of {Ib}, or a pharmaceutically acceptable salt thereof, wherein $R^6$ is unsubstituted $C_{2-4}$ alkenyl, unsubstituted $C_{2-4}$ alkynyl, or —$CH_2$—O—$CH_2CH_2O$—$R^7$; and $R^7$ is selected form the group consisting of hydrogen or methyl.

{IVb}. The compound of any one of {Ib}-{IIIb}, or a pharmaceutically acceptable salt or solvate thereof, wherein $R^1$ is H or unsubstituted $C_{1-6}$ alkyl and $R^4$ is unsubstituted $C_{1-6}$ alkyl.

{Vb}. The compound of any one of {Ib}-{IVb}, or a pharmaceutically acceptable salt or solvate thereof, wherein $R_1$ and $R^4$ are methyl.

{VIb}. The compound of {Vb}, wherein $R^6$ is unsubstituted ethyl, propyl, or butyl.

{VIIb}. A pharmaceutical composition, comprising a compound having the Formula VI:

VI

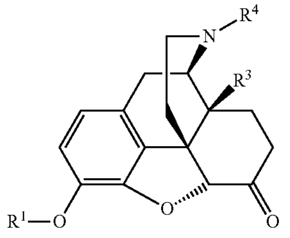

or a pharmaceutically acceptable salt or solvate thereof, wherein:

$R^1$ is H; $C_{1-6}$ alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$) alkylamino, carboxy, $C_{1-4}$ alkoxy, and $C_{1-4}$ alkoxycarbonyl;

$R^3$ is —OC(═O)$R^6$, wherein $R^6$ is selected from the group consisting of unsubstituted $C_{1-4}$ alkyl, unsubstituted $C_{2-4}$ alkenyl, unsubstituted $C_{2-4}$ alkynyl, or —$CH_2$—O—$(CH_2CH_2O)_m$—$R^7$;

m is 1;

$R^7$ is selected form the group consisting of hydrogen and $C_{1-6}$ alkyl; and PEG is one ethylene oxide unit or an oligomer of 2 to about 10 ethylene oxide subunits, and one or more pharmaceutically acceptable carriers.

{VIIIb}. The pharmaceutical composition of {VIIb}, comprising a compound of any one of {Ib}-{VIb}, or a pharmaceutically acceptable salt thereof.

{IXb}. The pharmaceutical composition of {VIIb}, comprising

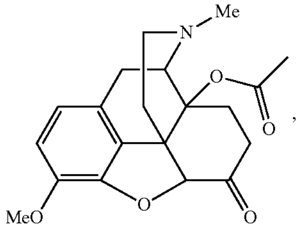 [SMILES: COc1ccc2c3c1OC1C(=O)CCC4(OC(C)=O)C(C2)N(C)CCC314]

, or a pharmaceutically acceptable salt of solvate thereof.

{Xb}. The pharmaceutical composition of any one of {VIIb}-{IXb}, further comprising at least one parent opioid.

{XIb}. The pharmaceutical composition of {Xb}, comprising from about 0.1 to about 30% of the at least one parent opioid.

{XIIb}. The pharmaceutical composition of {Xb} or {XIb}, comprising from about 1 to about 20 wt % of the at least one parent opioid.

{XIIIb}. The pharmaceutical composition of any one of {Xb}-{XIIb}, wherein the at least one parent opioid is oxycodone.

{XIVb}. The pharmaceutical composition of any one of {VIIb}-{XIIIb}, wherein said composition is formulated for an oral dosage form.

{XVb}. A composition, comprising one or more compounds of {Ib}-{VIb}, or a pharmaceutically acceptable salt or solvate thereof, and at least one parent opioid.

{XVIb}. The composition of {XVb}, comprising from about 0.1 to about 30 wt % of the at least one parent opioid.

{XVIIb}. The composition of {XVb} or {XVIb}, comprising from about 1 to about 20 wt % of the at least one parent opioid.

{XVIIIb}. The composition of any one of {XVb}-{XVIIb}, wherein the at least one parent opioid is oxycodone.

{XIXb}. An oral formulation, comprising a therapeutically effective amount of a composition of any one of {XVb}-{XVIIIb}.

{XXb}. A method of treating or preventing a disorder responsive to the modulation of one or more opioid receptors in a patient, comprising administering to the patient in need of such treatment or prevention an effective amount of a compound having the Formula VI:

VI

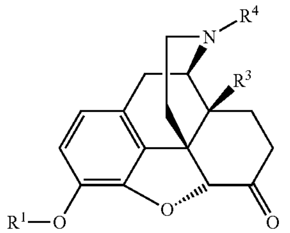

or a pharmaceutically acceptable salt or solvate thereof, wherein:

$R^1$ is H; $C_{1-6}$ alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$) alkylamino, carboxy, $C_{1-4}$ alkoxy, and $C_{1-4}$ alkoxycarbonyl;

$R^3$ is —OC(═O)$R^6$, wherein $R^6$ is selected from the group consisting of unsubstituted $C_{1-4}$ alkyl, unsubstituted $C_{2-4}$ alkenyl, unsubstituted $C_{2-4}$ alkynyl, or —$CH_2$—O—$(CH_2CH_2O)_m$—$R^7$;

m is 1;

$R^7$ is selected form the group consisting of hydrogen and $C_{1-6}$ alkyl; and PEG is one ethylene oxide unit or an oligomer of 2 to about 10 ethylene oxide subunits.

{XXIb}. The method of {XXb}, wherein a compound of any one of {Ib}-{VIb}, or a pharmaceutically acceptable salt or solvate thereof, is administered.

{XXIIb}. The method of {XXb}, wherein the compound is

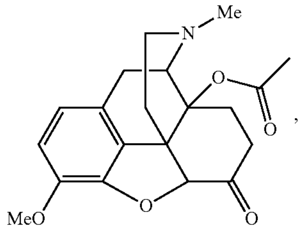 [SMILES: COc1ccc2c3c1OC1C(=O)CCC4(OC(C)=O)C(C2)N(C)CCC314]

, or a pharmaceutically acceptable salt of solvate thereof.

{XXIIIb}. The method of any one of {XXb}-{XXIIb}, wherein the disorder is pain.

{XXIVb}. A method of treating, ameliorating or preventing pain in a patient, comprising administering to the patient in need of such treatment, amelioration, or prevention an effective amount of a compound of a compound having the Formula VI:

VI

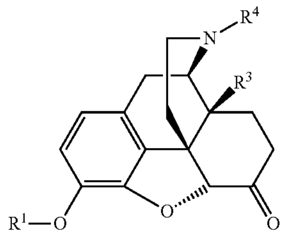

or a pharmaceutically acceptable salt or solvate thereof, wherein:

$R^1$ is H; $C_{1-6}$ alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$) alkylamino, carboxy, $C_{1-4}$ alkoxy, and $C_{1-4}$ alkoxycarbonyl;

$R^3$ is —OC(═O)$R^6$, wherein $R^6$ is selected from the group consisting of unsubstituted $C_{1-4}$ alkyl, unsubstituted $C_{2-4}$ alkenyl, unsubstituted $C_{2-4}$ alkynyl, or —$CH_2$—O—$(CH_2CH_2O)_m$—$R^7$;

m is 1;

$R^7$ is selected form the group consisting of hydrogen and $C_{1-6}$ alkyl; and PEG is one ethylene oxide unit or an oligomer of 2 to about 10 ethylene oxide subunits.

{XXVb}. The method of {XXIVb}, wherein a compound of any one of {Ib}-{VIb}, or a pharmaceutically acceptable salt or solvate thereof, is administered to the patient in need of such treatment, amelioration, or prevention.

{XXVIb}. The method of {XXIVb}, wherein the compound is

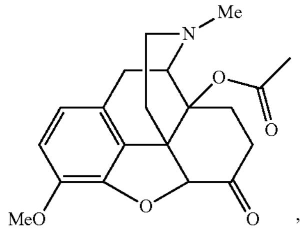

, or a pharmaceutically acceptable salt of solvate thereof.

{XXVIIb}. The method of any one of {XXIVb}-{XXVIb}, wherein the method is for treating pain.

{XXVIIIb}. The method of {XXVIIb}, wherein said pain is acute pain, chronic pain, or surgical pain.

{XXIXb}. The method of {XXVIIIb}, wherein said pain is chronic pain.

{XXXb}. The method of {XXIXb}, wherein said chronic pain is neuropathic pain, postoperative pain, or inflammatory pain.

{XXXIb}. A method of slowing the onset of activity of an opioid in a mammal in need of opioid therapy, comprising orally administering to the mammal a therapeutically effective amount of the compound or a mixture of the compounds according to any one of {Ib}-{VIIIc}, or a pharmaceutically acceptable salt or solvate thereof.

{XXXIIb}. A method of treating a disorder responsive to the modulation of one or more opioid receptors in a mammal in need of opioid therapy with delayed onset of opioid activities, comprising orally administering to the mammal a therapeutically effective amount of the compound or a mixture of the compounds according to any one of {Ib}-{VIIIb}, or a pharmaceutically acceptable salt or solvate thereof. In certain embodiments, the method further includes one or more parent opioid compounds, wherein the total amount of the Compounds of the Disclosure and the parent opioid compounds accounts for the therapeutically effective amount.

{XXXIIIb}. The method of {XXXIb} or {XXXIIb}, further comprising co-administering one or more other therapeutic agents.

{XXXIVb}. The method of {XXXIIIb}, wherein said one or more other therapeutic agents are one or more non-steroidal anti-inflammatory agents.

{XXXVb}. The method of {XXXIIIb}, wherein said one or more other therapeutic agents are one or more opioid agonists.

{XXXVIb}. The method of {XXXIIIb}, wherein said one or more other therapeutic agents are one or more opioid antagonists.

Medium Chain 6,14-bis-Substituted Enol Esters and Their Use as Prodrugs

The inventors have found that certain 6,14-bis-substituted enol esters of Formula II, having a medium length chain as a substituent at both the 6- and 14-positions, act as μ-opioid receptor agonists and can also be used as prodrugs. These compounds are thus analgesic compounds when made bioavailable from a dosage form, such as, for example, a transdermal, subcutaneous, intramuscular, intravenous, or parenteral dosage form. When the prodrugs are made bioavailable only in the lower gastrointestinal tract of a patient, they convert to the parent opioid, such as oxycodone, within a certain time to provide μ-opioid agonist functions from both the prodrug of Formula II and the parent opioid.

In this aspect of the invention, the disclosure provides the following particular embodiments.

{Ic}. A compound of Formula II:

II

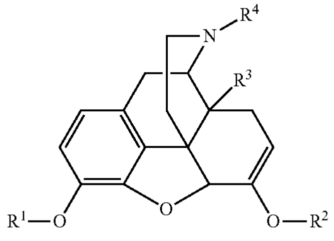

a pharmaceutically acceptable salt or solvate thereof, wherein:

$R^1$ is H; $C_{1-6}$ alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$) alkylamino, carboxy, $C_{1-4}$ alkoxy, and $C_{1-4}$ alkoxycarbonyl;

$R^2$ is —C(═O)$R^5$ and $R^3$ is —OC(═O)$R^6$, wherein $R^5$ and $R^6$ are the same or different and are selected from the group consisting of a straight-chain unsubstituted $C_{7-9}$ alkyl, a straight-chain unsubstituted $C_{7-9}$ alkenyl, a straight-chain unsubstituted $C_{7-9}$ alkynyl, —$CH_2$—O—$(CH_2CH_2O)_m$—$R^7$, —O—$(CH_2CH_2O)_n$—$R^7$, and —NH—$(CH_2CH_2O)_p$—$R^7$;

$R^7$ is selected form the group consisting of hydrogen and $C_{1-6}$ alkyl;

m is 2 or 3;

n and p are each independently 2, 3, or 4; and

PEG is one ethylene oxide unit or an oligomer of 2 to about 10 ethylene oxide subunits.

{IIc}. The compound of {Ic}, or a pharmaceutically acceptable salt or solvate thereof, wherein $R^5$ and $R^6$ are each independently selected from the group consisting of heptyl, octyl, nonyl, —$CH_2$—O—$(CH_2CH_2O)_m$—$R^7$, —O—$(CH_2CH_2O)_n$—$R^7$, and —NH—$(CH_2CH_2O)_p$—$R^7$; wherein $R^7$ is hydrogen or $C_{1-4}$ alkyl.

{IIIc}. The compound of {Ic} or {IIc}, wherein $R^5$ and $R^6$ are the same, having the Formula V:

V

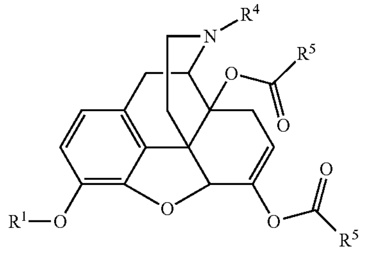

or a pharmaceutically acceptable salt or solvate thereof.

{IVc}. The compound of {IIIc}, or a pharmaceutically acceptable salt or solvate thereof, wherein $R^5$ is —$CH_2$—O—$(CH_2CH_2O)_m$—$R^7$, wherein $R^7$ is hydrogen or methyl.

{Vc}. The compound of {Ic} or {IIc}, or a pharmaceutically acceptable salt or solvate thereof, wherein $R^5$ and $R^6$ are different.

{VIc}. The compound of any one of {Ic}-{Vc}, or a pharmaceutically acceptable salt or solvate thereof, wherein $R^1$ is H or unsubstituted $C_{1-6}$ alkyl and $R^4$ is unsubstituted $C_{1-6}$ alkyl.

{VIIc}. The compound of any one of {Ic}-{VIc}, or a pharmaceutically acceptable salt or solvate thereof, wherein $R_1$ and $R^4$ are methyl.

{VIIIc}. The compound of {Ic} or {IIIc}, which is

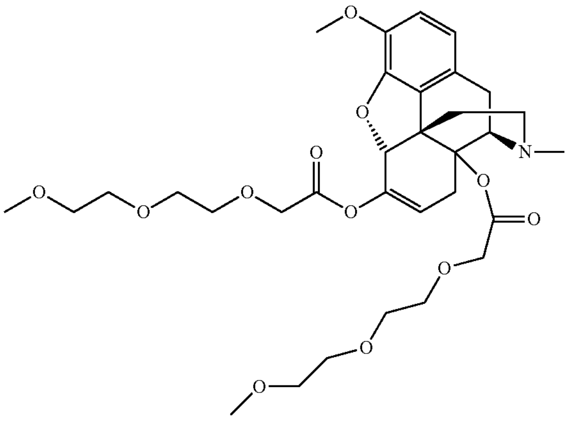

, or a pharmaceutically acceptable salt or solvate thereof.

{IXc}. A pharmaceutical composition, comprising a compound of any one of {Ic}-{VIIIc}, or a pharmaceutically acceptable salt thereof, and one or more pharmaceutically acceptable carriers.

{Xc}. A composition, comprising one or more compounds of {Ic}-{VIIIc}, or a pharmaceutically acceptable salt or solvate thereof, and at least one parent opioid.

{XIc}. The composition of {Xc}, comprising from about 0.1 to about 30 wt % of the at least one parent opioid.

{XIIc}. The composition of {Xc} or {XIc}, comprising from about 1 to about 20 wt % of the at least one parent opioid.

{XIIIc}. The composition of any one of {Xc}-{XIIc}, wherein the at least one parent opioid is oxycodone.

{XIVc}. An oral formulation, comprising a therapeutically effective amount of a composition of any one of {Xc}-{XIVc}.

{XVc}. A method of treating or preventing a disorder responsive to the modulation of one or more opioid receptors in a patient, comprising administering to the patient in need of such treatment or prevention an effective amount of a compound of any one of {Ic}-{VIIIc}, or a pharmaceutically acceptable salt or solvate thereof.

{XVIc}. The method of {XVc}, wherein the disorder is pain.

{XVIIc}. A method of treating, ameliorating or preventing pain in a patient, comprising administering an effective amount of a compound of any one of {Ic}-{VIIIc}, or a pharmaceutically acceptable salt or solvate thereof, to the patient in need of such treatment, amelioration, or prevention.

{XVIIIc}. The method of {XVIIc}, wherein the method is for treating pain.

{XIXc}. The method of {XVIIIc}, wherein said pain is acute pain, chronic pain, or surgical pain.

{XXc}. The method of {XIXc}, wherein said pain is chronic pain.

{XXIc}. The method of {XXc}, wherein said chronic pain is neuropathic pain, postoperative pain, or inflammatory pain.

{XXIIc}. A method of slowing the onset of activity of an opioid in a mammal in need of opioid therapy, comprising orally administering to the mammal a therapeutically effective amount of the compound or a mixture of the compounds according to any one of {Ic}-{VIIIc}, or a pharmaceutically acceptable salt or solvate thereof.

{XXIIIc}. A method of treating a disorder responsive to the modulation of one or more opioid receptors in a mammal in need of opioid therapy with delayed onset of opioid activities, comprising orally administering to the mammal a therapeutically effective amount of the compound or a mixture of the compounds according to any one of {Ic}-{VIIIc}, or a pharmaceutically acceptable salt or solvate thereof. In certain embodiments, the method further includes one or more parent opioid compounds, wherein the total amount of the Compounds of the Disclosure and the parent opioid compounds accounts for the therapeutically effective amount.

{XXIVc}. The method of {XXIIc} or {XXIIIc}, further comprising co-administering one or more other therapeutic agents.

{XXVc}. The method of {XXIVc}, wherein said one or more other therapeutic agents are one or more non-steroidal anti-inflammatory agents.

{XXVIc}. The method of {XXIVc}, wherein said one or more other therapeutic agents are one or more opioid agonists.

{XXVIIc}. The method of {XXIVc}, wherein said one or more other therapeutic agents are one or more opioid antagonists.

Long Chain 6,14-bis-Substituted Enol Esters and Their Use as Abuse Deterring Prodrugs The inventors have found that certain 6,14-bis-substituted enol esters of Formula II, having a long chain as a substituent at both the 6- and 14-positions, provide μ-opioid receptor agonist functions only when converted to the corresponding 6-substituted compound and the parent opioid in lower intestine. Specifically, the inventors found that 6,14-bis-lauroyl oxycodone provides μ-opioid agonist function when converted to 6-lauroyl oxycodone and oxycodone in the lower intestine of a patient. Thus, compounds of Formula II as defined above where both $R^5$ and $R^6$ are long can be used as abuse deterring opioid prodrugs. When these prodrugs are made bioavailable only in the lower gastrointestinal tract of a patient, the enol ester at the 14-position will hydrolyze to the 6-substituted enol ester compound and further to the parent opioid, such as oxycodone, within a certain time to provide μ-opioid agonist functions from both the 6-substituted enol ester prodrug of Formula IV discussed above and the parent opioid.

In this aspect of the invention, the disclosure provides the following particular embodiments.

{Id}. A compound of Formula II:

II

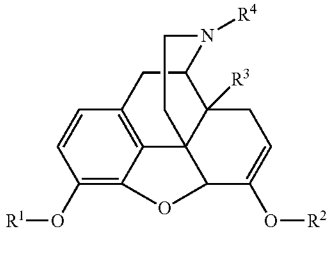

a pharmaceutically acceptable salt or solvate thereof, wherein:

$R^1$ is H; $C_{1-6}$ alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$) alkylamino, carboxy, $C_{1-4}$ alkoxy, and $C_{1-4}$ alkoxycarbonyl;

$R^2$ is —C(═O)$R^5$ and $R^3$ is —OC(═O)$R^6$, wherein $R^5$ and $R^6$ are the same or different and are selected from the group consisting of a straight-chain unsubstituted $C_{10-12}$ alkyl, a straight-chain unsubstituted $C_{10-12}$ alkenyl, a straight-chain unsubstituted $C_{10-12}$ alkynyl, —$CH_2$—O—$(CH_2CH_2O)_m$—$R^7$, —O—$(CH_2CH_2O)_n$—$R^7$, and —NH—$(CH_2CH_2O)_p$—$R^7$;

$R^7$ is selected form the group consisting of hydrogen and $C_{1-6}$ alkyl;

m is an integer between 4 and 9;

n and p are each independently an integer between 4 and 20; and

PEG is one ethylene oxide unit or an oligomer of 2 to about 10 ethylene oxide subunits.

{IId}. The compound of {Id}, or a pharmaceutically acceptable salt or solvate thereof, wherein $R^5$ and $R^6$ are each independently selected from the group consisting of decyl, undecyl, and dodecyl.

{IIId}. The compound of {Id} or {IId}, wherein $R^5$ and $R^6$ are the same, having the Formula V:

V

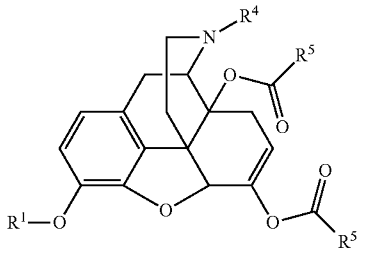

or a pharmaceutically acceptable salt or solvate thereof.

{IVd}. The compound of {IIId}, or a pharmaceutically acceptable salt or solvate thereof, wherein $R^5$ is undecyl.

{Vd}. The compound of {Id} or {IId}, or a pharmaceutically acceptable salt or solvate thereof, wherein $R^5$ and $R^6$ are different.

{VId}. The compound of any one of {Id}-{Vd}, or a pharmaceutically acceptable salt or solvate thereof, wherein $R^1$ is H or unsubstituted $C_{1-6}$ alkyl and $R^4$ is unsubstituted $C_{1-6}$ alkyl.

{VIId}. The compound of any one of {Id}-{VId}, or a pharmaceutically acceptable salt or solvate thereof, wherein $R_1$ and $R^4$ are methyl.

{VIIId}. The compound of {Id} or {IIId}, which is

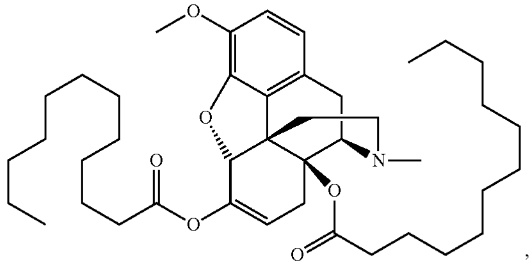

or a pharmaceutically acceptable salt or solvate thereof.

{IXd}. A pharmaceutical composition, comprising a compound of any one of {Id}-{VIIId}, or a pharmaceutically acceptable salt thereof, and one or more pharmaceutically acceptable carriers.

{Xd}. A composition, comprising one or more compounds of {Id}-{VIIId}, or a pharmaceutically acceptable salt or solvate thereof, and at least one parent opioid.

{XId}. The composition of {Xd}, comprising from about 0.1 to about 30 wt % of the at least one parent opioid.

{XIId}. The composition of {Xd} or {XId}, comprising from about 1 to about 20 wt % of the at least one parent opioid.

{XIIId}. The composition of any one of {Xd}-{XIId}, wherein the at least one parent opioid is oxycodone.

{XIVd}. An oral formulation, comprising a therapeutically effective amount of a composition of any one of {Xd}-{XIVd}.

{XVd}. A method of treating or preventing a disorder responsive to the modulation of one or more opioid receptors in a patient, comprising administering to the patient in need of such treatment or prevention an effective amount of a compound of any one of {Id}-{VIIId}, or a pharmaceutically acceptable salt or solvate thereof.

{XVId}. The method of {XVd}, wherein the disorder is pain.

{XVIId}. A method of treating, ameliorating or preventing pain in a patient, comprising administering an effective amount of a compound of any one of {Id}-{VIId}, or a pharmaceutically acceptable salt or solvate thereof, to the patient in need of such treatment, amelioration, or prevention.

{XVIIId}. The method of {XVIId}, wherein the method is for treating pain.

{XIXd}. The method of {XVIIId}, wherein said pain is acute pain, chronic pain, or surgical pain.

{XXd}. The method of {XIXd}, wherein said pain is chronic pain.

{XXId}. The method of {XXd}, wherein said chronic pain is neuropathic pain, postoperative pain, or inflammatory pain.

{XXIId}. A method of treating or preventing pain in a mammal identified as in need of opioid therapy with delayed onset of activities, comprising orally administering to the mammal a therapeutically effective amount of the compound or a mixture of the compounds according to any one of {Id}-{VIIId}, or a pharmaceutically acceptable salt or solvate thereof. In certain embodiments, the method further includes one or more parent opioid compounds, wherein the total amount of the Compounds of the Disclosure and the parent opioid compounds accounts for the therapeutically effective amount.

{XXIIId}. A method of treating a disorder responsive to the modulation of one or more opioid receptors in a mammal in need of opioid therapy with delayed onset of opioid activities, comprising orally administering to the mammal a therapeutically effective amount of the compound or a mixture of the compounds according to any one of {Id}-{VIIId}, or a pharmaceutically acceptable salt or solvate thereof.

{XXIVd}. The method of {XXIId} or {XXIIId}, comprising orally administering a compound or a mixture of compounds having the Formula V:

V

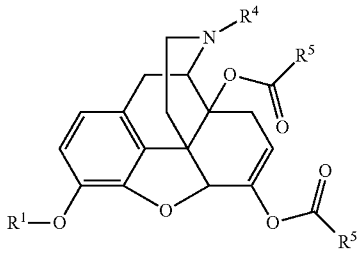

or a pharmaceutically acceptable salt or solvate thereof, wherein $R^1$ is H or unsubstituted $C_{1-6}$ alkyl;

$R^4$ is unsubstituted $C_{1-6}$ alkyl; and $R^5$ is decyl, undecyl, or dodecyl.

{XXVd}. The method of {XXIVd}, wherein $R^1$ is H or methyl, and $R^4$ is methyl.

{XXVId}. The method of {XXIVd} or {XXVd}, wherein $R^5$ is undecyl.

{XXVIId}. The method of any one of {XXIId}-{XXVId}, further comprising co-administering one or more other therapeutic agents.

{XXVIIId}. The method of {XXVIId}, wherein said one or more other therapeutic agents are one or more non-steroidal anti-inflammatory agents.

{XXIXd}. The method of {XXVIId}, wherein said one or more other therapeutic agents are one or more opioid agonists.

{XXXd}. The method of {XXVIId}, wherein said one or more other therapeutic agents are one or more opioid antagonists.

{XXXId}. The method of any one of {XXIVd}-{XXVId}, wherein said compound or mixture of compounds is administered in a single dosage form further comprising an effective amount of the parent opioid.

Long Chain 14-Substituted Enol Esters and Their Use as Partial Agonists and Partial Antagonists The inventors have found that certain 14-substituted enol esters of Formula VI, having a long chain substituent at the 14-position, act as partial μ-opioid receptor agonists and partial μ-opioid receptor antagonists, such as 16-lauroyl oxycodone. Accordingly, these long chain substituted enol esters may be useful in methods of treating or preventing opioid-induced adverse pharmacodynamic responses induced by the administration of another opioid. The opioid-induced adverse pharmacodynamic responses include, for example, bowel dysfunction, nausea, vomiting, somnolence, dizziness, respiratory depression, headache, dry mouth, sedation, swears, asthenia, hypotension, dysphoria, delirium, miosis, pruritis, urticarial, urinary retention, hyperalgesia, allodynia, physical dependence and tolerance. In one embodiment, opioid-induced adverse pharmacodymanic response is selected from the group consisting of constipation, diarrhea, withdrawal from alcohol addiction and withdrawal from drug addiction.

In this aspect of the invention, the disclosure provides the following particular embodiments.

{Ie}. A compound of Formula VI:

VI

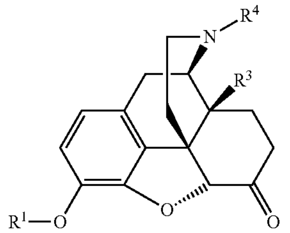

or a pharmaceutically acceptable salt or solvate thereof, wherein:

$R^1$ is H; $C_{1-6}$ alkyl optionally substituted with 1, 2, or 3 substituents, each independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di($C_{1-4}$) alkylamino, carboxy, $C_{1-4}$ alkoxy, and $C_{1-4}$ alkoxycarbonyl;

$R^3$ is —OC(=O)$R^6$, wherein $R^6$ is selected from the group consisting of a straight-chain unsubstituted $C_{10-12}$ alkyl, a straight-chain unsubstituted $C_{10-12}$ alkenyl, a straight-chain unsubstituted $C_{10-12}$ alkynyl, —$CH_2$—O—$(CH_2CH_2O)_m$—$R^7$, —O—$(CH_2CH_2O)_n$—$R^7$, and —NH—$(CH_2CH_2O)_p$—$R^7$;

$R^7$ is selected form the group consisting of hydrogen and $C_{1-6}$ alkyl;

m is an integer between 4 and 9;

n and p are each independently an integer between 4 and 20; and

PEG is one ethylene oxide unit or an oligomer of 2 to about 10 ethylene oxide subunits.

{IIe}. The compound of {Ie}, or a pharmaceutically acceptable salt or solvate thereof, wherein $R^6$ is decyl, undecyl, or dodecyl.

{IIIe}. The compound of {Ie} or {IIe}, or a pharmaceutically acceptable salt or solvate thereof, wherein $R^1$ is H or unsubstituted $C_{1-6}$ alkyl and $R^4$ is unsubstituted $C_{1-6}$ alkyl.

{IVe}. The compound of any one of {Ie}-{IIIe}, or a pharmaceutically acceptable salt or solvate thereof, wherein $R^6$ is undecyl.

{Ve}. The compound of any one of {Ie}-{IVe}, or a pharmaceutically acceptable salt or solvate thereof, wherein $R_1$ and $R^4$ are methyl.

{VIe}. The compound of {Ie}, which is

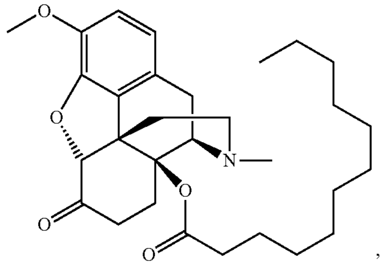

, or a pharmaceutically acceptable salt or solvate thereof.

{VIIe}. A pharmaceutical composition, comprising a compound of any one of {Ie}-{VIe}, or a pharmaceutically acceptable salt thereof, and one or more pharmaceutically acceptable carriers.

{VIIIe}. A composition, comprising one or more compounds of {Ie}-{VIe}, or a pharmaceutically acceptable salt or solvate thereof, and at least one parent opioid.

{IXe}. The composition of {VIIIe}, comprising from about 0.1 to about 30 wt % of the at least one parent opioid.

{Xe}. The composition of {VIIIe} or {IXe}, comprising from about 1 to about 20 wt % of the at least one parent opioid.

{XIe}. The composition of any one of {VIIIe}-{Xe}, wherein the at least one parent opioid is oxycodone.

{XIIe}. An oral formulation, comprising a therapeutically effective amount of a composition of any one of {VIIIe}-{XIe}.

{XIIIe}. A method of treating or preventing a disorder responsive to the modulation of one or more opioid receptors in a patient, comprising administering to the patient in need of such treatment or prevention an effective amount of a compound of any one of {Ie}-{VIe}, or a pharmaceutically acceptable salt or solvate thereof.

{XIVe}. The method of {XIIIe}, wherein the disorder is constipation, diarrhea, withdrawal from alcohol addiction, or withdrawal from drug addiction.

{XVe}. A method of treating or preventing an opioid-induced adverse pharmacodynamic response, comprising administering to a patient in need thereof an effective amount of a compound of any one of {Ie}-{VIe}, or a pharmaceutically acceptable salt or solvate thereof, to treat or prevent the adverse pharmacodynamic effect induced by the administration of another opioid.

{XVIe}. A method of treating, ameliorating or preventing constipation, diarrhea, withdrawal from alcohol addiction or withdrawal from drug addiction in a patient, comprising administering an effective amount of a compound of any one of {Ie}-{VIe}, or a pharmaceutically acceptable salt or solvate thereof, to the patient in need of such treatment or prevention.

Pharmaceutical Compositions

The present invention is further directed to pharmaceutical compositions comprising a therapeutically effective amount of at least one Compound of the Disclosure and a pharmaceutically acceptable carrier. Pharmaceutical compositions of the present invention can, if desired, also contain one or more other compatible pharmaceutically active agents.

Pharmaceutical compositions within the scope of this invention include all compositions wherein a Compound of the Disclosure is present in an amount that is effective (via conversion to the parent opioid) to achieve its intended purpose. While individual needs will vary, determination of optimal ranges of effective amounts of each component is within the skill in the art in view of the present disclosure. In some embodiments, a Compound of the Disclosure can be administered to a mammal. In some embodiments, the mammal is a human, and preferably a patient being treated for a condition that can be treated with an opioid, such as pain. As will be evident from this disclosure, Compounds of the Disclosure, and mixtures thereof, are preferably administered orally. In some embodiments, a Compound of the Disclosure is administered at a dose of from 0.1 to 5 mg/kg, or a molar equivalent amount of the pharmaceutically acceptable salt thereof, of the body weight of the mammal being treated.

In some embodiments, the unit oral dosage comprises between 5 mg and 640 mg, between 5 mg and 320 mg, between 5 mg and 200 mg, between 5 mg and 160 mg, between 5 mg and 100 mg, between 5 mg and 50 mg, between 5 mg and 25 mg, between 5 mg and 20 mg, and between 5 mg and 10 mg of a Compound of the Disclosure, or mixtures thereof. In some embodiments, the unit oral dose is 5 mg, 10 mg, 20 mg, 25 mg, 50 mg, 60 mg, 80 mg, 100 mg, 120 mg, 160 mg, 320 mg, or 640 mg of a free Compound of the Disclosure, or a molar equivalent of a pharmaceutically acceptable salt thereof.

In some embodiments, the oral dosage form is a unit oral dosage form that is administered every 4 hours, every 6 hours, every 8 hours, every 12 hours, or every 24 hours.

In some embodiments, a Compound of the Disclosure, or a mixture thereof, can be administered as part of a pharmaceutical composition. In some embodiments, the pharmaceutical compositions of the disclosure contain one or more suitable pharmaceutically acceptable carriers selected from known excipients and auxiliaries to facilitate processing of the compounds into pharmaceutical dosage forms and/or to facilitate or otherwise control dissolution of the dosage form. In a particular embodiment, pharmaceutical compositions of the disclosure are in dosage forms that can be administered orally. In some embodiments, the pharmaceutical compositions are in the form of solid oral dosage forms, such as powders, granules, tablets, pellets, multiparticulates, dragees, or capsules. In other embodiments, the pharmaceutical compositions are in the form of liquid oral dosage forms, such as oral solutions, oral suspensions, or oral emulsions.

In some embodiments, the oral dosage form contains from 0.01 to 99 weight percent, 0.01 to 90 weight percent, 0.01 to 85 weight percent, 0.01 to 80 weight percent, or 0.01 to 75 weight percent of a Compound of the Disclosure, or a mixture thereof, together with one or more excipients.

Orally administered pharmaceutical compositions of the disclosure can contain one or more excipients. Suitable excipients include fillers such as saccharides, for example lactose or sucrose, mannitol, sodium saccharin or sorbitol, magnesiun carbonate, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol; sweetening agents such as fructose, aspartame or saccharin; flavoring agents such as peppermint, oil of wintergreen, or cherry; coloring agents; and preserving agents, to provide a pharmaceutically palatable preparation. In addition, dye stuffs or pigments can be added to the tablets or dragee coatings, for example, for identification or in order to characterize combinations of active compound doses. Other examples of suitable pharmaceutical excipients are described in *Remington's Pharmaceutical Sciences* pp. 1447-1676 (Alfonso R. Gennaro ed., 19th ed. 1995), incorporated herein by reference. In one embodiment, the excipients are of pharmaceutical grade.

In some embodiments, pharmaceutical compositions of the present disclosure are manufactured in a manner which will be known in view of the present disclosure, such as, for example, by means of conventional mixing, granulating, dragee-making, dissolving, or lyophilizing processes.

Pharmaceutical compositions of the disclosure can be administered by any means to achieve their intended purpose. Preferably, administration is by the oral route. The dose administered and the frequency of dosing will be dependent upon the age, health, gender, medical condition and weight of the recipient, any concurrent treatment if any, frequency of treatment, and the nature of the effect desired, among other factors.

A Compound of the Disclosure, or a mixture thereof, can be delivered in an immediate release system, a controlled-release system or a sustained-release system. For a more detailed description of the controlled- or sustained-release systems, see e.g. U.S. Pat. Nos. 5,672,360, 5,968,551, 6,294,195, 7,270,831, and 7,514,100. The controlled- or sustained-release systems can also be prepared by methods known in the art (see, e.g., Goodson, in Medical Applications of Controlled Release, vol. 2, pp. 115-138 (1984)). Other controlled- or sustained-release systems discussed in the review by Langer, *Science* 249:1527-1533 (1990) can be used as well.

A Compound of the Disclosure, or a mixture thereof, can be prepared as a gastric-retentive drug delivery system, which is retained in the stomach or upper part of the gastrointestinal tract for controlled delivery. For a more detailed description of gastric-retentive drug delivery systems, see e.g. U.S. Pat. Nos. 5,232,704; 7,157,100; 7,838,028: and U.S. Patent Appl. Publication No. 2006/0013876. Gastric-retentive drug delivery systems can also be prepared by methods known in the art (see, e.g., Sharma, N., et al., *International Journal of Research in Pharmaceutical and Biomedical Sciences* 2:428-441 (2011)).

The production of tablets and granules as disclosed in U.S. Pat. Nos. 4,167,558 and 6,090,411 can also be used. The preparation of bilayered tablets as disclosed in U.S. Pat. No. 4,140,755 can also be used.

Powders comprising the active agent, a hydrocolloid, a pH dependent polymer, and a binder, with all of these being placed in a capsule, are disclosed in U.S. Pat. No. 5,169,638. The forms disclosed in said document are suitable for delivering compounds of the present invention.

U.S. Pat. No. 6,635,279 discloses a mixture of polyvinyl acetate and polyvinylpyrrolidone, as well as excipients. These forms can be prepared by simple processes and show exceptional mechanical strengths. The forms disclosed in said document are suitable for delivering a compound or compounds of the present disclosure.

In some embodiments, Compounds of the Disclosure are co-administered with one or more other therapeutic agents.

In some embodiments, a Compound of the Disclosure can be co-administered with one or more non-opioid analgesics. Suitable non-opioid analgesics include, but are not limited to a non-steroidal anti-inflammatory agent selected from aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflurisal, flufenisal, piroxicam, sudoxicam, isoxicam, pharmaceutically acceptable salts thereof, and mixtures thereof. Other suitable non-opioid analgesics include, but are not limited to, salicylic acid derivatives, including without limitation, sodium salicylate, choline magnesium trisalicylate, salsalate, diflunisal, salicyl salicylic acid, sulfasalazine, and olsalazin; para-aminophennol derivatives including without limitation, acetaminophen; indole and indene acetic acids, including without limitation, indomethacin, sulindac, and etodolac; heteroaryl acetic acids, including without limitation, tolmetin, diclofenac, and ketorolac; anthranilic acids (fenamates), including mefenamic acid and meclofenamic acid; enolic acids, including without limitation, oxicams (piroxicam and tenoxicam), and pyrazolidinediones (phenylbutazone and oxyphenthartazone); and alkanones, including without limitation, nabumetone. For a more detailed description of the non-opioid analgesics that can be co-administered with Compounds of the Disclosure, see Paul A. Insel, Analgesic-Antipyretic and Antiinflammatory Agents and Drugs Employed in The Treatment of Gout in Goodman & Gilman's The Pharmacological Basis of Therapeutics, 617-657 (Perry B. Molinhoff and Raymond W. Ruddon, eds., 9th ed. 1996), and Glen R. Hanson, Analgesic, Antipyretic and Anti-Inflammatory Drugs in Remington: The Science and Practice of Pharmacy, vol. II, 1196-1221 (A. R. Gelmaro, ed. 19th ed. 1995).

In some embodiments, a Compound of the Disclosure can be co-administered with one or more opioid agonists. Suitable opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In some embodiments, a Compound of the Disclosure can be co-administered with one or more antimigraine agents. Suitable antimigraine agents include, but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

In some embodiments, a Compound of the Disclosure can be co-administered with one or more antiemetic agents. Suitable antiemetic agents include, but are not limited to, metoclopromide, domperidone, prochlorperazine, promethazine, chlorpromazine, trimethobenzamide, ondansetron, granisetron, hydroxyzine acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

In some embodiments, a Compound of the Disclosure can be co-administered with one or more β-adrenergic blockers. Suitable β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol, and mixtures thereof.

In some embodiments, a Compound of the Disclosure can be co-administered with one or more anticonvulsants. Suitable anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, and mixtures thereof.

In some embodiments, a Compound of the Disclosure can be co-administered with one or more antidepressants. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, zimeldine, and mixtures thereof.

In some embodiments, a Compound of the Disclosure can be co-administered with one or more $Ca^{2+}$-channel blockers. Suitable $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lormerizine, bencyclane, etafenone, fantofarone, perhexiline, and mixtures thereof.

In some embodiments, a Compound of the Disclosure can be co-formulated or co-administered with an opioid antagonist, such as naltrexone, naloxone, nalmefene, nalorphine, nalbuphine, naloxoneazinen, methylnaltrexone, ketylcyclazocine, norbinaltorphimine, naltrindole, 6-β-naloxol, 6-β-naltrexol, alvimopan, cyprodime, diprenorphine, gemazocine, 5'-guanidinonaltrindoIe, JDTic ((3R)-7-Hydroxy-N-[(2S)-1-[(3R,4R)-4-(3-hydroxyphenyl)-3,4-dimethylpiperidin-1-yl]-3-methylbutan-2-yl]-1,2,3,4-tetrahydroisoquinoline-3-carboxamide), levallorphan, naldemedine, nalmexone, nalorphine dinicotinate, naloxazone, naloxegol, naloxol, naoloxonazine, naltiben, oxilorphan, quadazocine, samidorphan, and mixtures thereof according to International Patent Appl. Publication No. WO 03/084520.

Since certain Compounds of the Disclosure can act as prodrugs, they can be used for the same purpose as their parent compounds. In some embodiments, Compounds of the Disclosure are useful for treating, ameliorating or preventing pain including acute pain, chronic pain, neuropathic pain, inflammatory pain, and surgical pain. In another embodiment, Compounds of the Disclosure are useful for treating, ameliorating or preventing opioid-induced adverse pharmacodynamic responses.

Compounds of the Disclosure can be used to treat or prevent acute, chronic pain (which includes but is not limited to, neuropathic pain, postoperative pain, and inflammatory pain), or surgical pain. Examples of pain that can be treated or prevented using a Compound of the Invention include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

Acute pain includes, but is not limited to, perioperative pain, postoperative pain, post-traumatic pain, acute disease related pain, and pain related to diagnostic procedures, orthopedic manipulations, and myocardial infarction. Acute pain in the perioperative setting includes pain because of pre-existing disease, the surgical procedure, e.g., associated drains, chest or nasogastric tubes, or complications, or a combination of disease-related and procedure-related sources.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Compounds of the Disclosure can be used to treat or prevent pain associated with inflammation or with an inflammatory disease in a patient. Such pain can arise where there is an inflammation of the body tissue which can be a local inflammatory response or a systemic inflammation. For example, a Compound of the Disclosure can be used to treat or prevent pain associated with inflammatory diseases including, but not limited to, organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. Compounds of the Disclosure can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

Compounds of the Disclosure can be used to treat or prevent pain associated with nerve injury (i.e., neuropathic pain). Chronic neuropathic pain is a heterogenous disease state with an unclear etiology. In chronic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Chronic neuropathic pain can be caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

Compounds of the Disclosure can be used to treat or prevent pain associated with migraine including, but not limited to, migraine without aura ("common migraine"), migraine with aura ("classic migraine"), migraine without headache, basilar migraine, familial hemiplegic migraine, migrainous infarction, and migraine with prolonged aura.

In some embodiments, Compounds of the Disclosure are useful as cough suppressants, and in treating or ameliorating dyspnea, diarrhea, and dysentery.

In each of the aforementioned instances, the methods of the present invention require administering to a mammal in need of such treatment an effective amount of a compound of any one of Formulae I to VI, or a pharmaceutically acceptable salt or solvate thereof, or a mixture thereof.

In some embodiments, Compounds of the Disclosure are tested for their μ-, κ-, δ-, or ORL-1 opioid receptor binding activity and their functional profile at the μ-, κ-, δ-, or ORL-1 opioid receptor by the following in vitro binding assays.

In Vitro Assay Protocols

μ-Opioid Receptor Binding Assay Procedures: Radioligand dose-displacement binding assays for μ-opioid receptors can use 0.3 nM [$^3$H]-diprenorphine (Perkin Elmer, Shelton, CT), with 5 mg membrane protein/well in a final volume of 500 μl binding buffer (10 mM $MgCl_2$, 1 mM EDTA, 5% DMSO, 50 mM HEPES, pH 7.4). Reactions are carried out in the absence or presence of increasing concentrations of unlabeled naloxone. All reactions are conducted in 96-deep well polypropylene plates for 2 hours at room temperature. Binding reactions are terminated by rapid filtration onto 96-well Unifilter GF/C filter plates (Perkin Elmer, Shelton, CT), presoaked in 0.5% polyethylenimine using a 96-well tissue harvester (Perkin Elmer, Shelton, CT) followed by performing three filtration washes with 500 μl of ice-cold binding buffer. Filter plates are subsequently dried at 50° C. for 2-3 hours. BetaScint scintillation cocktail (Perkin Elmer, Shelton, CT) is added (50 μl/well), and plates are counted using a Packard Top-Count for 1 min/well. The data are analyzed using the one-site competition curve fitting functions in GraphPad PRISM™ v. 3.0 or higher (San Diego, Calif.), or an in-house function for one-site competition curve-fitting. Data are expressed as mean±S.E.M. The results are represented as inhibition constants, $K_i$ values (the concentration of a compound that produces half maximal inhibition).

μ-Opioid Receptor Functional Assay Procedures: [$^{35}$S]GTPγS functional assays are conducted using freshly thawed μ-receptor membranes prepared in-house from a cell line expressing recombinant μ opioid receptor in a HEK-293, CHO or U-2 OS cell background or purchased from a commercial source (Perkin Elmer, Shelton, CT; or DiscovRx, Fremont, CA). Assay reactions are prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, CT). The prepared membrane solution (190 μl/well) is transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates are incubated for 30 min at about 25° C. with shaking. Reactions are terminated by rapid filtration onto 96-well Unifilter GF/B filter plates (Perkin Elmer, Shelton, CT) using a 96-well tissue harvester (Perkin Elmer, Shelton, CT) followed by three filtration washes with 200 μl of ice-cold wash buffer (10 mM $NaH_2PO_4$, 10 mM $Na_2HPO_4$, pH 7.4). Filter plates are subsequently dried at 50° C. for 2-3 hours. BetaScint scintillation cocktail (Perkin Elmer, Shelton, CT) is added (50 μl/well) and plates are counted using a Packard Top-Count for 1 min/well. Data is analyzed using the sigmoidal dose-response curve fitting functions in GraphPad PRISM v. 3.0, or an in-house function for non-linear, sigmoidal dose-response curve-fitting. Data are expressed as mean±S.E.M. The results from the functional assays are represented as $EC_{50}$ values (the effective concentration of a compound that causes 50% of the maximum response).

[$^{35}$S]GTPγS functional assays can also be conducted using freshly thawed μ-receptor membranes prepared from a cell line expressing recombinant μ opioid receptor in a CHO-K1 cell background.

κ-Opioid Receptor Binding Assay Procedures: Membranes from HEK-293, CHO or U-2 OS cells expressing the recombinant human kappa opioid receptor (κ) are prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes from a cell line naturally expressing kappa opioid receptor can also be used. Membranes are collected by centrifugation at 30,000× g for 15 min at 4° C. and pellets are resuspended in hypotonic buffer to a final concentration of 1-3 mg/mL. Protein concentrations are determined using the BioRad protein assay reagent with bovine serum albumen as standard. Aliquots of κ receptor membranes are stored at −80° C.

Radioligand dose displacement assays can use 0.4 nM [$^3$H]-U69,593 (GE Healthcare, Piscataway, NJ; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding is determined in the presence of 10 μM unlabeled naloxone or U69,593. All reactions are performed in 96-well polypropylene plates for 1 hour at a temperature of about 25° C. Binding reactions are terminated by rapid filtration onto 96-well Unifilter GF/C filter plates (Perkin Elmer, Shelton, CT) presoaked in 0.5% polyethylenimine (Sigma). Harvesting is performed using a 96-well tissue harvester (Perkin Elmer, Shelton, CT) followed by five filtration washes with 200 μl ice-cold binding buffer. Filter plates are subsequently dried at 50° C. for 1-2 hours. Fifty μl/well scintillation cocktail (Perkin Elmer, Shelton, CT) is added and plates are counted in a Packard Top-Count for 1 min/well. The data are analyzed using the one-site competition curve fitting functions in GraphPad PRISM™ v. 3.0 or higher (San Diego, Calif.), or an in-house function for one-site competition curve-fitting. Data are expressed as mean±S.E.M. The results are represented as inhibition constants, $K_i$ values (the concentration of a compound that produces half maximal inhibition).

κ-Opioid Receptor Functional Assay Procedures: Functional [$^{35}$S]GTPγS binding assays can be conducted as follows. κ opioid receptor membrane solution is prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) is transferred to 96-shallow well polypropylene plates containing 10 μl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Perkin Elmer, Shelton, CT) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates are subsequently dried at 50° C. for 2-3 hours. Fifty μl/well scintillation cocktail (Perkin Elmer, Shelton, CT) is added and plates were counted in a Packard Top-Count for 1 min/well. The data are analyzed using the one-site competition curve fitting functions in GraphPad PRISM™ v. 3.0 or higher (San Diego, Calif.), or an in-house function for one-site competition curve-fitting. Data are expressed as mean±S.E.M. The results from the functional assays are represented as $EC_{50}$ values (the effective concentration of a compound that causes 50% of the maximum response).

δ-Opioid Receptor Binding Assay Procedures: δ-Opioid Receptor Binding Assay Procedures are conducted as follows. Radioligand dose-displacement assays can use 0.3 nM [$^3$H]-Naltrindole (Perkin Elmer, Shelton, CT; 33.0 Ci/mmole) with 5 μg membrane protein (Perkin Elmer, Shelton, CT) in a final volume of 500 μl binding buffer (5 mM $MgCl_2$, 5% DMSO, 50 mM Trizma base, pH 7.4). Non-specific binding is determined in the presence of 25 μM unlabeled naloxone. All reactions are performed in 96-deep well polypropylene plates for 1 hour at a temperature of about 25° C. Binding reactions are terminated by rapid filtration onto 96-well Unifilter GF/C filter plates (Perkin Elmer, Shelton, CT) presoaked in 0.5% polyethylenimine (Sigma). Harvesting is performed using a 96-well tissue harvester (Perkin Elmer, Shelton, CT) followed by five filtration washes with 500 μl ice-cold binding buffer. Filter plates are subsequently dried at 50° C. for 1-2 hours. Fifty μl/well scintillation cocktail (Perkin Elmer, Shelton, CT) is added and plates are counted in a Packard Top-Count for 1 min/well. The data were analyzed using the one-site competition curve fitting functions in GraphPad PRISM™ v. 3.0 or higher (San Diego, Calif), or an in-house function for one-site competition curve-fitting. Data are expressed as mean±S.E.M. The results are represented as inhibition constants, $K_i$ values (the concentration of a compound that produces half maximal inhibition).

δ-Opioid Receptor Functional Assay Procedures: Functional [$^{35}$S]GTPγS binding assays are conducted as follows. δ opioid receptor membrane solution is prepared by sequentially adding final concentrations of 0.026 μg/μl δ membrane protein (Perkin Elmer, Shelton, CT), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) is transferred to 96-shallow well polypropylene plates containing 10 μl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Perkin Elmer, Shelton, CT) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates are subsequently dried at 50° C. for 1-2 hours. Fifty μl/well scintillation cocktail (Perkin Elmer, Shelton, CT) is added and plates are counted in a Packard Top-count for 1 min/well. The data were analyzed using the one-site competition curve fitting functions in GraphPad PRISM™ v. 3.0 or higher (San Diego, Calif.), or an in-house function for one-site competition curve-fitting. Data are expressed as mean±S.E.M. The results from the functional assays are represented as $EC_{50}$ values (the effective concentration of a compound that causes 50% of the maximum response).

ORL-1 Receptor Binding Assay Procedure: Membranes from recombinant HEK-293 cells expressing the human opioid receptor-like receptor (ORL-1) (Perkin Elmer, Shelton, CT) can be prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000× g for 15 min at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) use 0.1 nM [$^3$H]-nociceptin (Perkin Elmer, Shelton, CT; 87.7 Ci/mmole) with 12 μg membrane protein in a final volume of 500 μl binding buffer (10 mM $MgCl_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, CT) presoaked in 0.5% polyethylenimine (Sigma). Harvesting is performed using a 96-well tissue harvester (Perkin Elmer, Shelton, CT) followed by three filtration washes with 500 μl ice-cold binding buffer. Filter plates are subsequently dried at 50° C. for 2-3 hours. Fifty μl/well scintillation cocktail (Perkin Elmer, Shelton, CT) is added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting. Data are expressed as mean±S.E.M. The results are represented as inhibition constants, $K_i$ values (the concentration of a compound that produces half maximal inhibition).

ORL-1 Receptor Functional Assay Procedure: Membranes from recombinant HEK-293 cells expressing the human opioid receptor-like (ORL-1) (Perkin Elmer, Shelton, CT) can be prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000× g for 15 min at 4° C., and pellets resuspended in hypotonic buffer to a final concentration of 1-3 mg/ml.

Protein concentrations are determined using the BioRad protein assay reagent with bovine serum albumen as standard. Aliquots of the ORL-1 receptor membranes are stored at −80° C.

Functional [$^{35}$S]GTPγS binding assays are conducted as follows. ORL-1 membrane solution is prepared by sequentially adding final concentrations of 0.026 μg/μl ORL-1 membrane protein, 10 μg/ml saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) is transferred to 96-shallow well polypropylene plates containing 10 μl of 20× concentrated stock solutions of agonist/nociceptin prepared in DMSO. Plates are incubated for 30 min at room temperature with shaking. Reactions are terminated by rapid filtration onto 96-well Unifilter GF/B filter plates (Perkin Elmer, Shelton, CT) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates are subsequently dried at 50° C. for 2-3 hours. Fifty μl/well scintillation cocktail (Perkin Elmer, Shelton, CT) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting. The results from the functional assays are represented as $EC_{50}$ values (the effective concentration of a compound that causes 50% of the maximum response).

In Vivo Pharmacology

Brain distribution: Compounds of the Disclosure can be tested for in vivo distribution to brains after oral administration using, for example, the following test. Sprague Dawley rats are dosed 10 mg/kg orally with the test compound. The dosing solution is in 25% 2-hydroxypropyl beta-cyclodextrin (HPBCD) and the dosing volume is 5 mL/kg. One hour after administration, the highest possible volume of blood is drawn through cardiac puncture. Plasma is separated from the whole blood by centrifugation and submitted for analysis. Following bleeding, the whole brains are harvested, briefly rinsed in cold normal saline, and then snap-frozen in liquid nitrogen. Both plasma and brain samples are stored at −70° C. prior to analysis.

For analyzing the plasma samples, calibration curves are prepared by spiking known amounts of analytes into commercially available control rat plasma. 200 μL aliquots of standards and study samples are added with 800 μL aqueous solution of internal standard (oxycodone) and extracted on the $C_{18}$ solid-phase cartridges (96-well format, 3M) according to the following procedure. The cartridges are activated by applying 500 μL methanol followed by 500 μL of water. Then the samples are applied and cartridges are washed with 500 μL of water and then eluted with 2×500 μL of 1% formic acid in methanol followed by 2×500 μL of 2% ammonia in methanol. Upon evaporation and reconstitution, the samples are analyzed by LC/MS/MS. For analyzing the brain samples, study samples and control brains are homogenized with water in a ratio of 1:10 weight per volume. Calibration curves are prepared by spiking known amounts of the analytes into control brain homogenates. 500 μL aliquots of standards and study samples are added with 500 μL aqueous solution of internal standard (oxycodone) and extracted on the $C_{18}$ solid-phase cartridges (96-well format, 3M) according to the procedure described earlier for plasma samples. Upon evaporation and reconstitution, the samples are analyzed by LC/MS/MS.

Analytes and internal standards are chromatographed on Zorbax Extended $C_{18}$ column (4.6×150 mm, 3.5 microns particle size) under water-acetonitrile gradient conditions (specific gradient for each analyte) using procedures known in the art. The effluents are analyzed by MS/MS. The analytes are registered as "daughter" ions of the analytes' molecular ions on the second quadropole of the instrument. The MS/MS conditions are optimized for each individual analyte to achieve maximum selectivity and sensitivity.

The concentrations of the unknown samples are calculated based on the parameters of the corresponding calibration curves. The brain concentrations expressed in "ng per g of tissue" are obtained by multiplying the corresponding homogenate concentrations by a factor of 10 (dilution factor during the homogenation step). The brain-to-blood ratio are calculated as the ratio of the corresponding brain (ng/g) and plasma (ng/mL) concentrations for each individual animal and the means and standard deviations are calculated for the groups of three.

Anti-Nociceptive Activity Study in Mice: Compounds of the Invention can be tested for their anti-nociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, CA) are used in all experiments. Food is withdrawn on the day of the experiment. Mice are placed in Plexiglass jars for at least 1 hour to accommodate to the environment. Following the accommodation period, mice are weighed and given either the compound of interest administered orally in a vehicle, or the appropriate volume of vehicle (10% Tween-80). Thirty minutes after the oral dosing, mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5 minute intervals for 1 hour after the formalin injection. All experiments are done in a blinded manner during the light cycle. The early phase of the formalin response is measured as licking/biting between 0 and 5 minutes, and the late phase is measured from 15 to 50 minutes. Differences between vehicle and drug treated groups are analyzed by one-way analysis of variance (ANOVA). A p value≤0.05 is considered significant. Compounds having activity in blocking the acute and second phase of formalin-induced paw-licking activity are considered to be efficacious for acute and chronic pain.

In Vivo Assays for Pain Using Rats as Test Animals

Test Animals: Each experiment uses rats weighing between 200-260 g at the start of the experiment. The rats are group-housed and have free access to food and water at all times, except prior to oral administration of a Compound of the Disclosure when food is removed for about 16 hours before dosing. A control group acts as a comparison to rats treated with a Compound of the Disclosure. The control group is administered the carrier for the Compound of the Disclosure. The volume of carrier administered to the control group is the same as the volume of carrier and Compound of the Disclosure administered to the test group.

Acute Pain: To assess the actions of a Compound of the Disclosure for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Disclosure. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20\text{ s} - \text{pre-administration latency})} \times 100$$

The rat tail flick test is described in F.E. D'Amour et al., "A Method for Determining Loss of Pain Sensation," *J. Pharmacol. Exp. Ther.* 72:74-79 (1941).

To assess the actions of a Compound of the Disclosure for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rat is placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) excape or attempted escape from the testing device; or 4) vocalization. Data are expressed as response latency(s) and the percentage of the maximal possible effect is calculated as described above for the tail flick test. The hot plate test is described in G. Woolfe and A. D. MacDonald, *J. Pharmacol. Exp. Ther.* 80:300-307 (1944).

Inflammatory Pain: To assess the actions of a Compound of the Disclosure for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

[(post administration PWT)−(pre-administration PWT)]

% Reversal=×100

[(baseline PWT)−(pre-administration PWT)]

Neuropathic Pain: To assess the actions of a Compound of the Disclosure for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a 3/8 curved, reversed-cutting mini-needle and tightly ligated so that the dorsal 1/3 to 1/2 of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below.

The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The rat is gently restrained, its hindpaw is placed on a small round platform, and punctate pressure is applied to the dorsal surface of the hindpaw in a graded manner. The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia: The plantar test can be used to assess thermal hyperalgesia. For this test, hind paw withdrawal latencies to a noxious thermal stimulus applied to the plantar surface of the hindpaw are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression: To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., *Intensive Care Med.* (26): 585-591 (2000).

Assessment of Gastric Motility: Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

A composition of the disclosure is prepared by a method comprising admixing a Compound of the Disclosure with a pharmaceutically acceptable carrier or excipient. Admixing can be accomplished using methods known for admixing a compound (or derivative) and a pharmaceutically acceptable carrier or excipient. In one embodiment, the Compound of the Disclosure is present in the composition in an effective amount.

The present disclosure also relates to a kit, comprising a sterile container containing an effective amount of a Compound of the Disclosure and instructions for therapeutic use.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

"HPLC" means high-performance liquid chromatography.

"$CDCl_3$" means deuterated chloroform.

"DCM" means dicholoromethane.

"THF" means tetrahydrofuran.

"RT" means room temperature.

$^1$H NMR spectra were recorded in $CDCl_3$ on a Varian Mercury Plus 400 MHz NMR instrument.

HPLC spectra were recorded in MeOH/$H_2O$ mixture on an Agilent 1100 Series LC/MS instrument.

"COSY NMR" means correlation spectroscopy NMR which is a type of two-dimensional nuclear magnetic resonance spectroscopy (2D NMR). COSY NMR spectrum was recorded in $CDCl_3$ on a Varian Mercury Plus 400 MHz NMR instrument.

"FTIR" means Fourier-transform infrared spectroscopy. FTIR was recorded as solid form on a Thermo Scientific Nicolet 6700 FTIR instrument.

"HATR" means Horizontal Attenuated Total Reflectance.

"HRMS" means high resolution mass spectrometry. HRMS was recorded in MeOH/$H_2O$ mixture on a Thermo Scientific Q exactive LC/MS instrument.

LCMS analysis of the compounds were conducted by the following methods

Column type: Phenomenex Luna C18 Column, 5 micrometer, 2×50 mm;

Instrument: Agilent 1100 Series LC/MS instrument;

Detector wave length: 250 nm; and

Mobile phase: 90% 2.8 nM ammonium formate in water, 10% MeOH, pH 10 with $NH_4OH$, and MeOH.

Example 1

Preparation of 6-acetyl Oxycodone

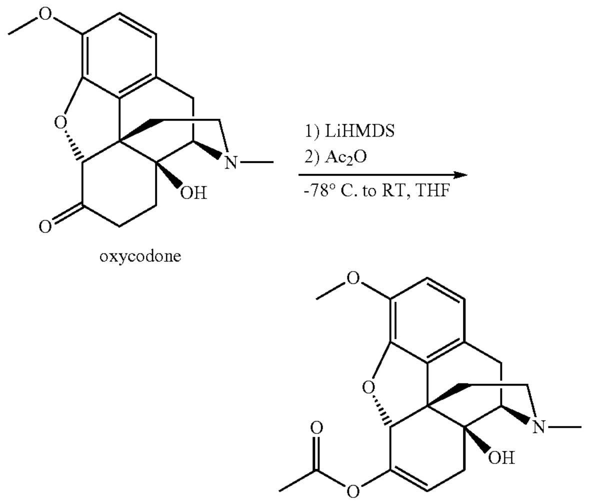

oxycodone 6-acetyl oxycodone

Oxycodone free base (0.316 g, 1 mmol) was mixed with $LiN(TMS)_2$ (3 mmol) in anhydrous THF (10 mL) at −78° C. for 30 minutes and stirring was continued at room temperature for 1 hour. The reaction mixture was again cooled to −78° C. and acetic anhydride (0.47 mL, 5 mmol) was added to this reaction mixture. The reaction was stirred overnight at room temperature and then concentrated under reduced pressure. The residue was neutralized with saturated $NaHCO_3$, and extracted with DCM (3×15 mL), followed by $MgSO_4$ drying, filtration and concentration to give an amber oil as a crude product.

A portion of the crude product was purified by preparatory HPLC under the following conditions and parameters:

Column type: Gemini 5 µm NX-C18 110 Å (Vendor: Phenomenex part #00F-4454-N0); size: 150×10 mm HPLC Method:

Instrument: Agilent 1100 Series LC/MS instrument

Column Temp: 25° C.

Detector Wave length: 250 nm

Concentration: 10 mg/mL in 1:1 $MeOH:H_2O$ solution

Flow rate: 2.5 mL/min

Mobile Phase:

Solvent B: 90% 2.8 mM Amomonium Formate in Water, 10% Methanol, pH 10 with $NH_4OH$ Solvent C: Methanol Gradient conditions:

| Time (min) | % Solvent B | % Solvent C |
|---|---|---|
| 0 | 60 | 40 |
| 20 | 60 | 40 |
| 50 | 15 | 85 |
| 55 | 5 | 95 |
| 65 | 5 | 95 |
| 67 | 60 | 40 |
| 70 | 60 | 40 |

The peak at 11.0 minutes was collected, identified by mass spectrometry and concentrated at reduced pressure. The HPLC chromatogram is provided in FIG. 1D. 40 mg of 90-95% pure title product was collected as a white powder.

Figure 1B:
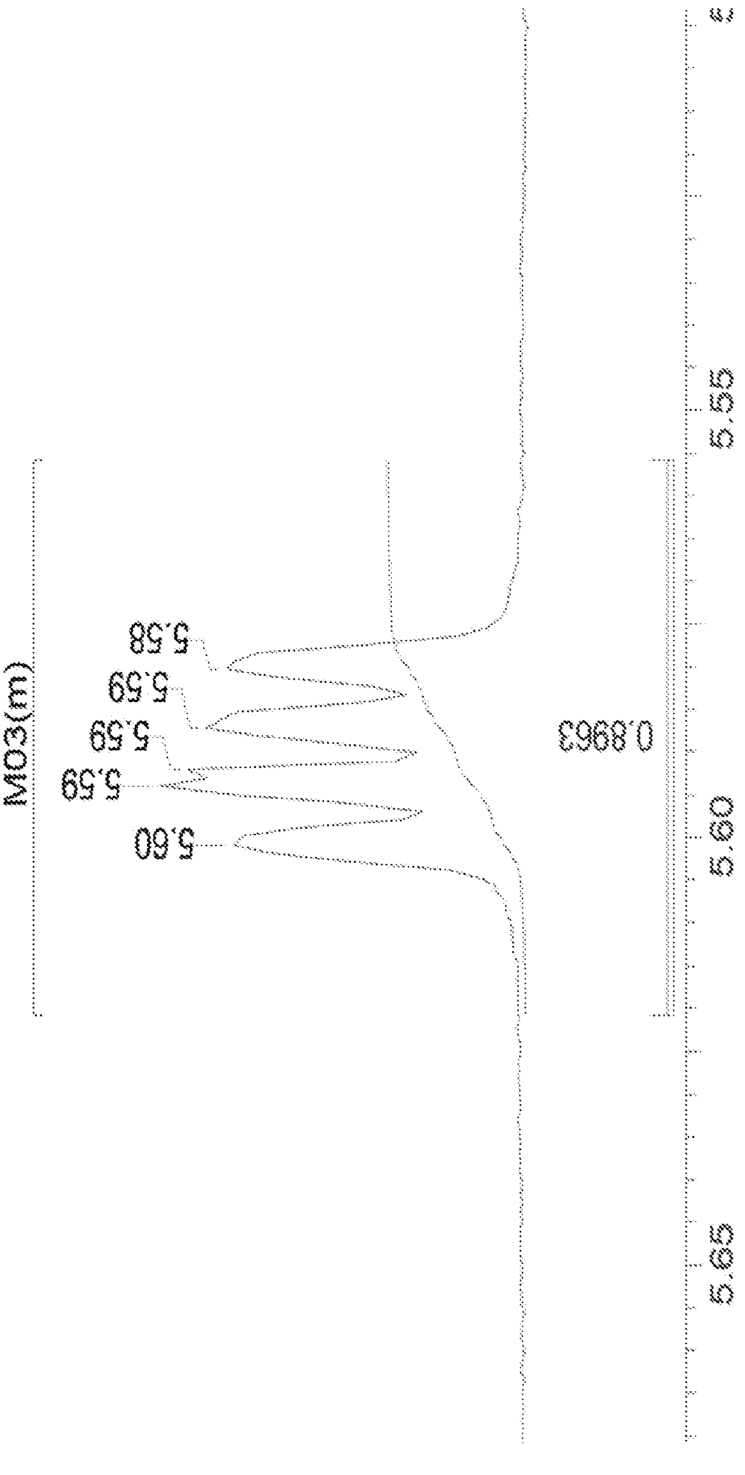
Figure 1C:
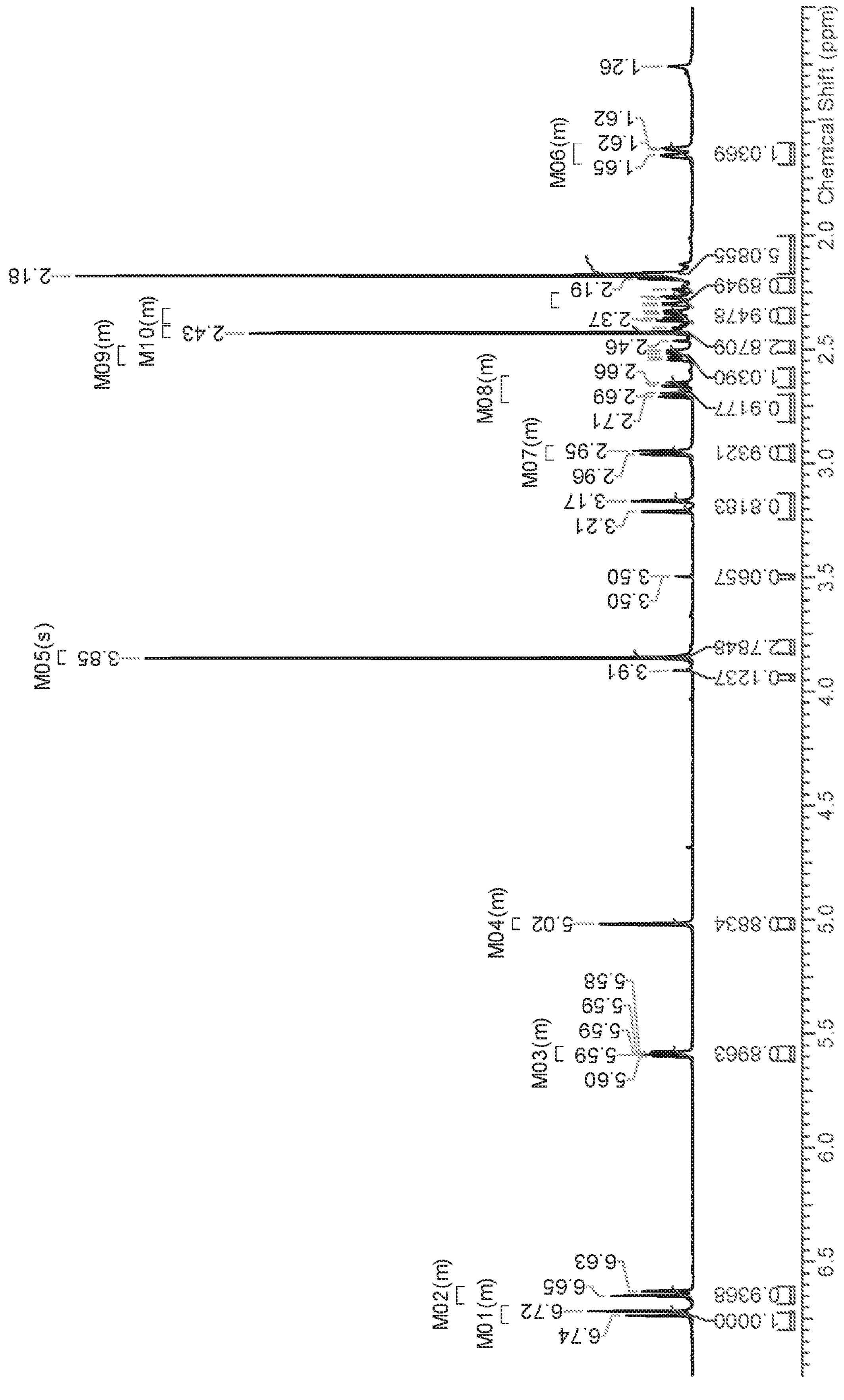
Figure 1D:
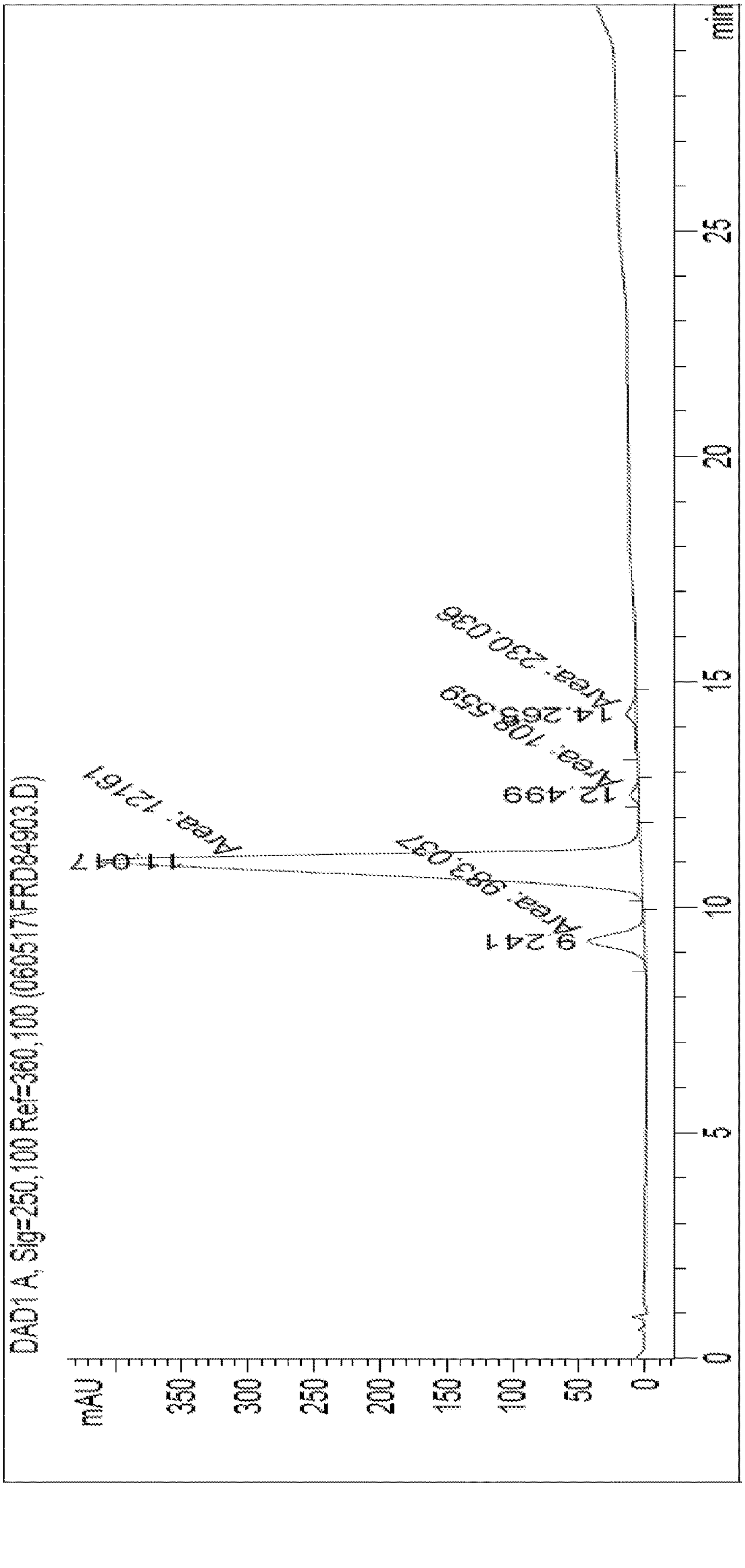

A sample of the title product was dissolved in $CDCl_3$, filtered and analyzed by $^1H$ NMR and COSY NMR. The $^1H$ NMR spectra is provided in FIG. 1C. The COSY NMR and a partial $^1H$ NMR spectra clearly showed the 7-proton at 5.59 ppm as a doublet of doublets (with broadening from weak coupling to proton-5) as shown in FIG. 1A and FIG. 1B, respectively.

FTIR (HATR, $cm^{-1}$): 2933, 2838, 1754, 1601, 1503, 1446, 1368, 1210, 1144, 1111, 1044, 910, and 796.

HRMS calculated for $C_{20}H_{24}NO_5^+$ $(M+H^+)$: 358.1654; Found: 358.1644.

Example 2

Preparation of 6-PEG Oxycodone

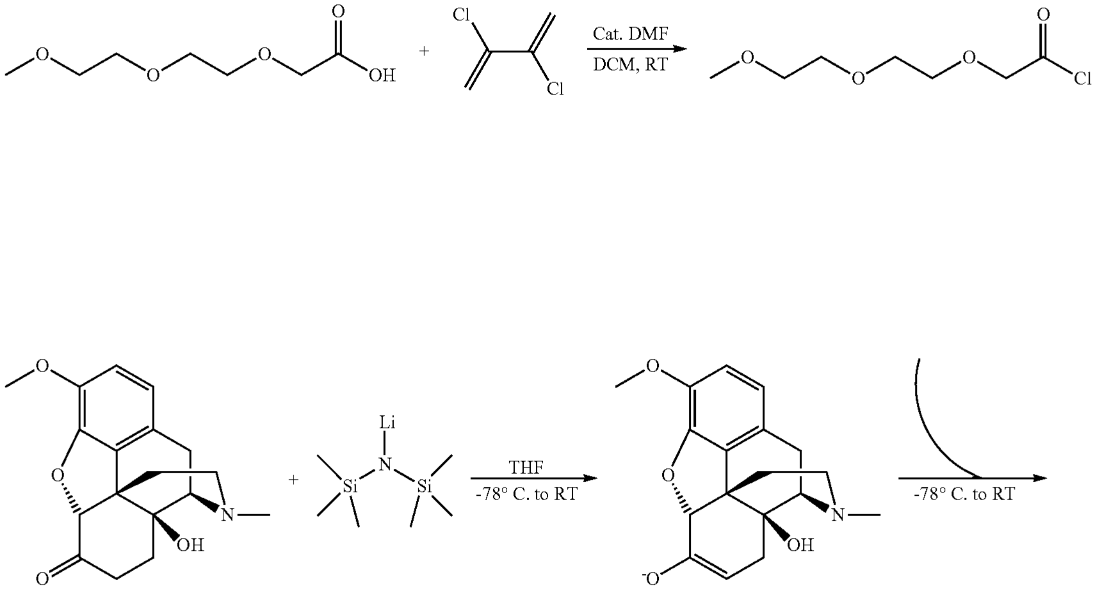

-continued

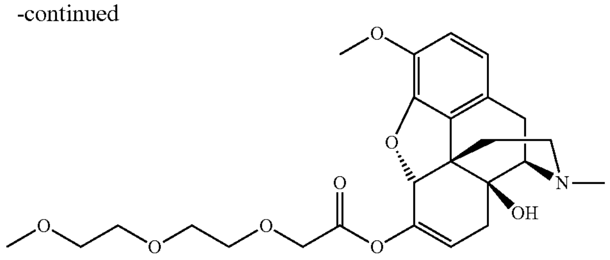

6-PEG oxycodone

Oxycodone free base (0.316 g, 1 mmol) was mixed with $LiN(TMS)_2$ (3 mmol) in anhydrous THF (20 ml) at −78° C. for 30 minutes followed by stirring at room temperature for 30 minutes. The solution was re-chilled to −78° C. and a solution of an acetyl chloride derivative, made by reacting 2-[2-(2-methoxyethoxy)ethoxy]acetic acid (30 mg, 3 mmol) with 3 eq. of oxalyl chloride, was added to this reaction mixture. The reaction was let stir overnight and warm up slowly to room temperature. Based on LCMS, the conversion for the title compound was about 44%. The reaction mixture was rotary evaporated and re-dissolved in 20 ml of DCM. Saturated sodium bicarbonate solution was added until the aqueous layer was neutralized. After extracting the mixture with DCM (20 mL×3 times), the combined organic layer was dried over $MgSO_4$ and concentrated under reduced pressure affording an amber oil 0.85 g. A portion of the residue was purified by preparatory HPLC to give 85% pure title product and 15% of oxycodone as impurity.

Figure 2A:
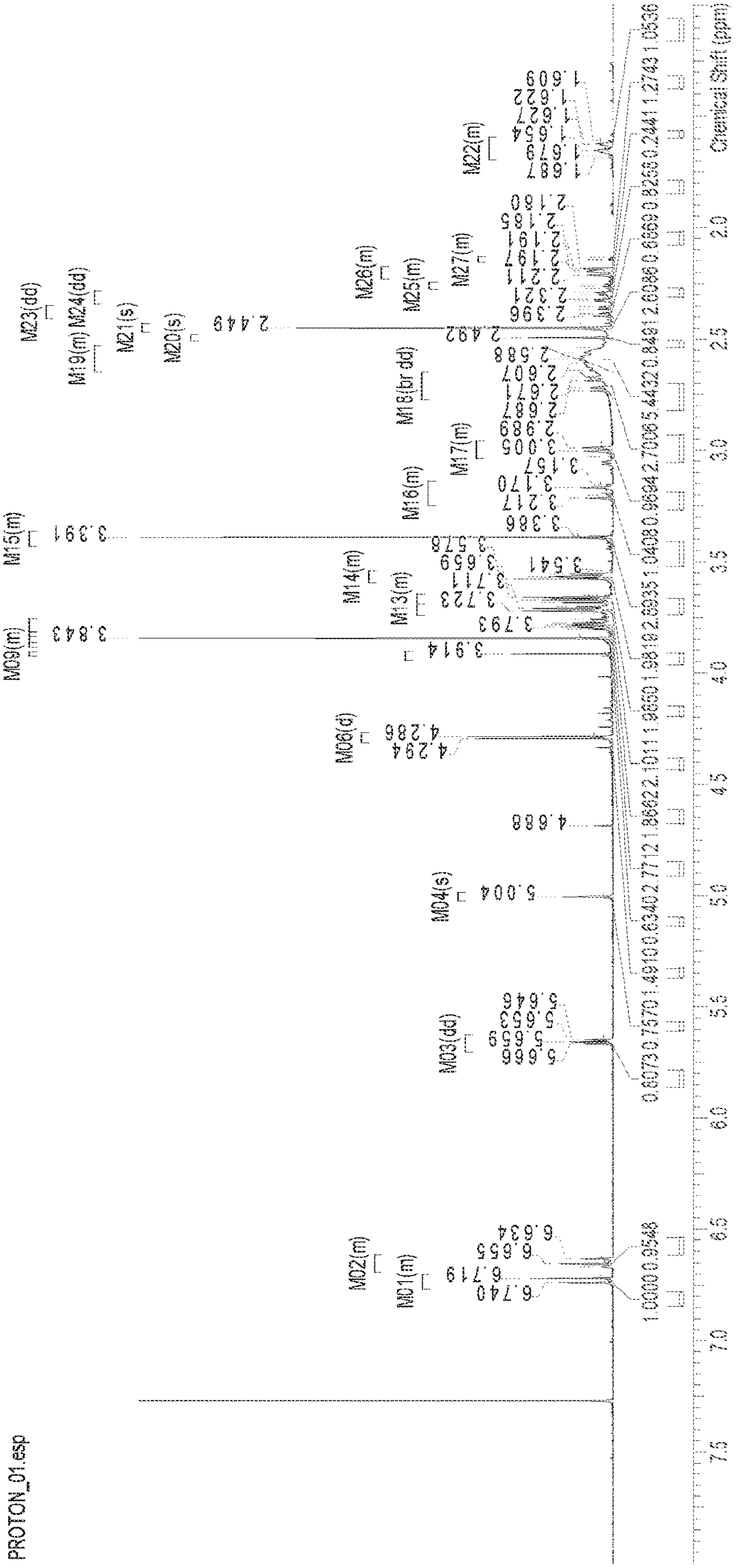
FIG. 2A and FIG. 2B depict the $^1$H NMR spectrum and the HPLC chromatogram, respectively, for 6-PEG oxycodone prepared in Example 2.
Figure 2B:
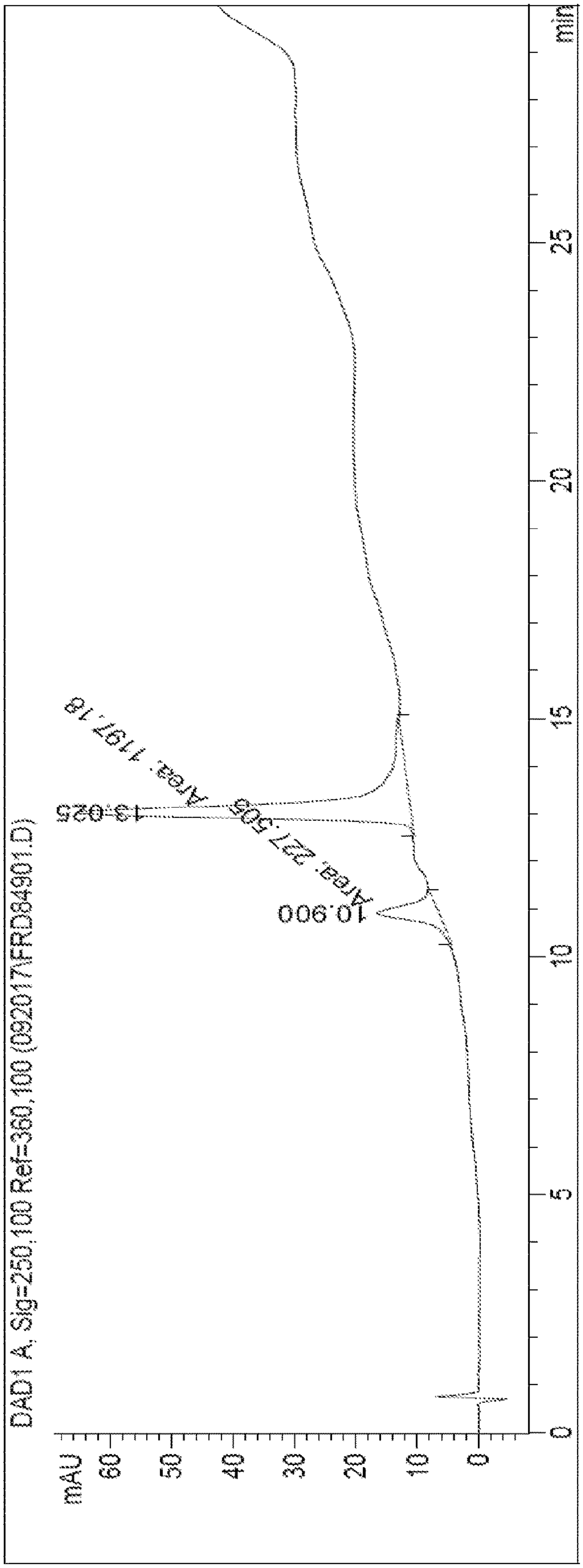

FIG. 2A and FIG. 2B depict the $^1H$ NMR spectrum and the HPLC chromatogram, respectively, for the title compound.

Example 3

Preparation of 6,14-bis-lauroyl Oxycodone

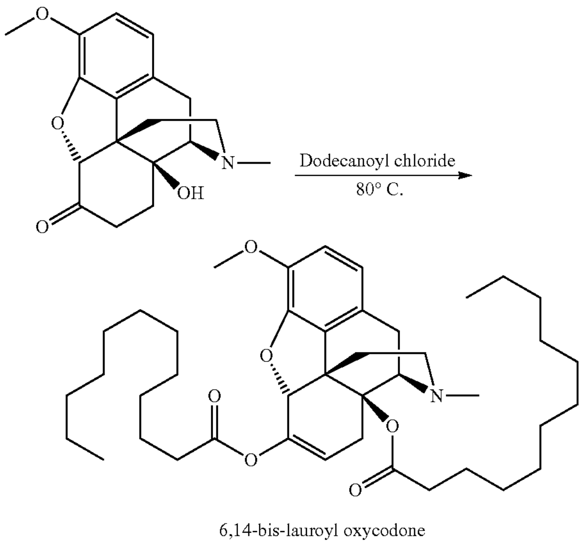

6,14-bis-lauroyl oxycodone

Oxycodone (0.3415 g), 4-(dimethylamino)pyridine (0.3475 g) and lauroyl chloride (7 mL) were stirred under nitrogen and heated to 80° C. for three days. The reaction mixture was then cooled and poured in to water (100 mL). After stirring for two hours, the mixture was neutralized with concentrated ammonium hydroxide (2 mL) and gently extracted with chloroform (50 mL, slight stirring). The aqueous layer was diluted with saturated $NaHCO_3$ solution (25 mL) and extracted with chloroform (25 mL, formed emulsion). After standing overnight to separate the organic layer followed by drying over $MgSO_4$, filtration and concentration under reduced pressure to give 0.39 g of amber oil as the title product. Yield: 53%.

Figure 3A:
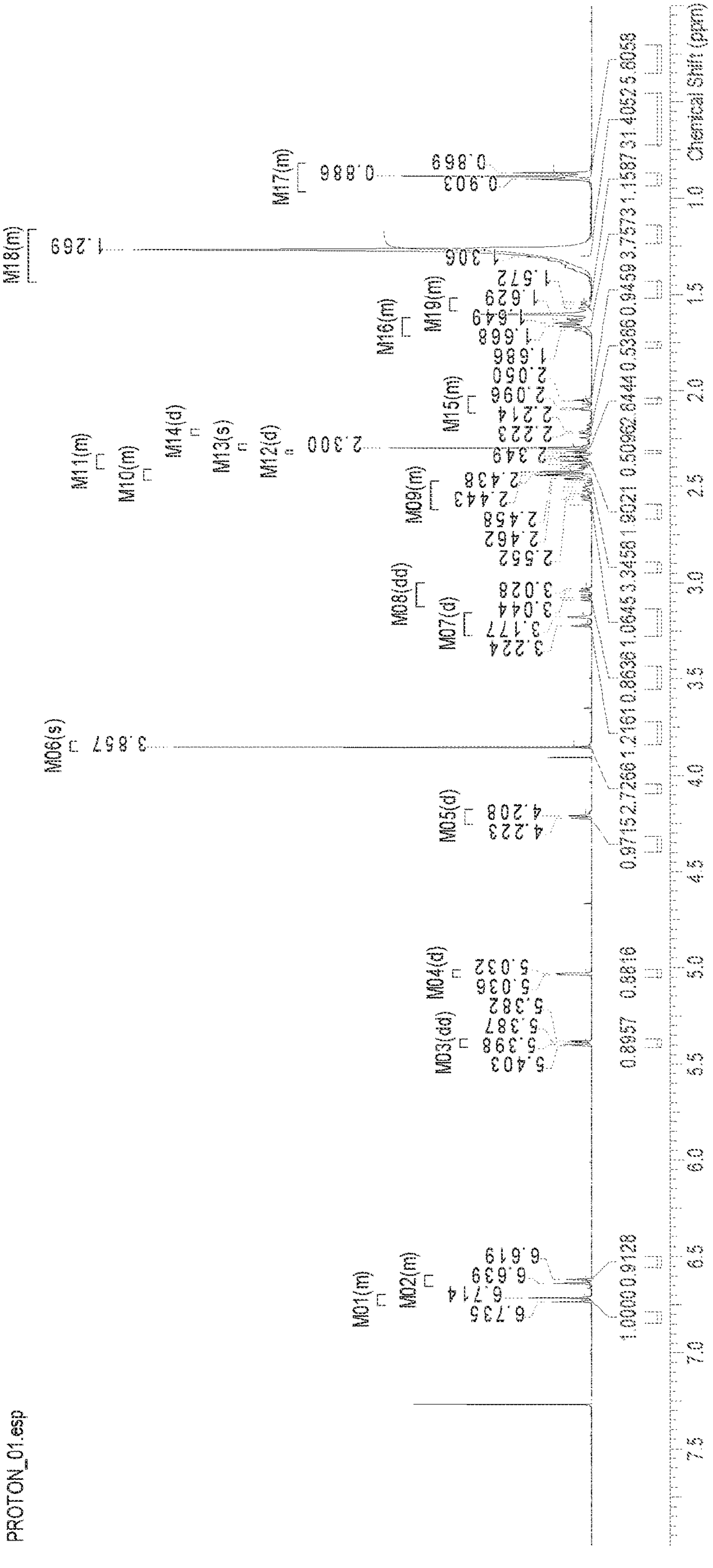
FIG. 3A and FIG. 3B depict the $^1$H NMR spectrum and the HPLC chromatogram, respectively, for 6,14-bis-lauroyl oxycodone prepared in Example 3.
Figure 3B:
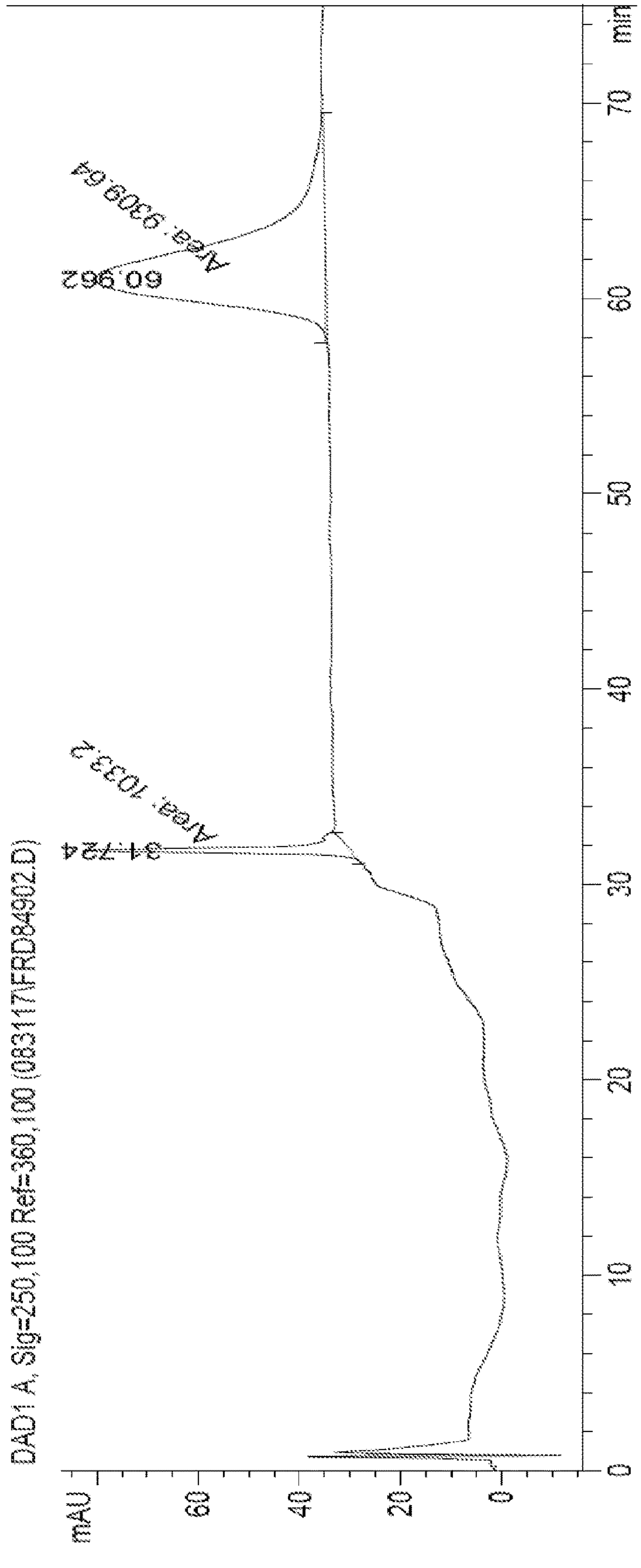

FIG. 3A and FIG. 3B depict the $^1H$ NMR spectrum and the HPLC chromatogram, respectively, for the title compound.

Example 4

Preparation of 6-lauroyl Oxycodone

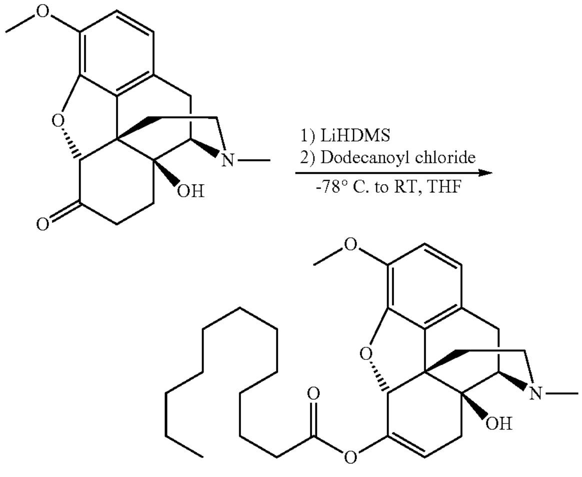

6-lauroyl oxycodone

Oxycodone (312 mg, 1 mmol) was mixed with $LiN(TMS)_2$ (i.e., LiHDMS) (3 mmol) in anhydrous THF (10 mL) at −78° C. for 30 minutes followed by room temperature for 30 minutes. The solution was rechilled to −78° C. and to this reaction mixture, dodecanoyl chloride (0.65 mL, 5 mmol) was added. The reaction was stirred for three days at room temperature. Aqueous work up with chloroform extraction followed by $MgSO_4$ drying, filtration and concentration gave an amber oil. Purification by silica gel chromatography afforded an amber solid 0.289 g as a product. Yield: 59%.

Figure 4A:
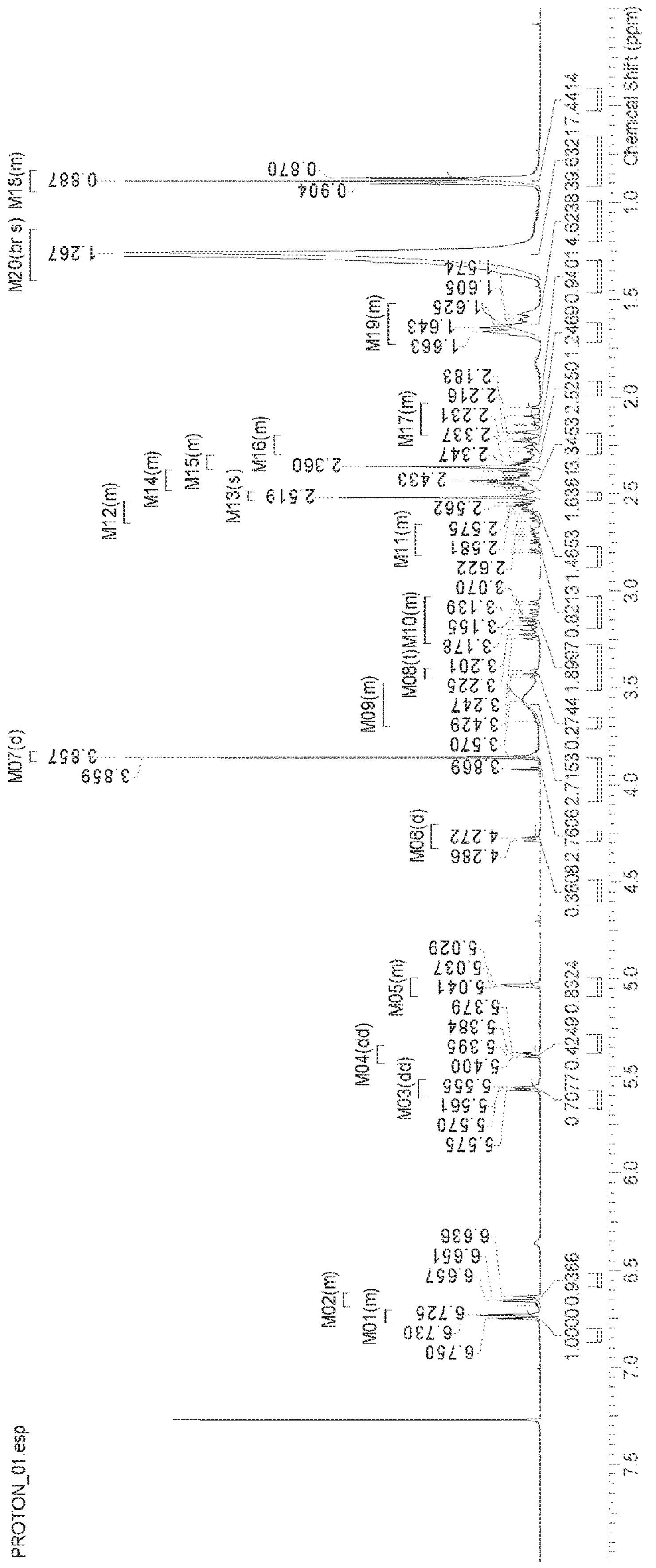
FIG. 4A and FIG. 4B depict the $^1$H NMR spectrum and the HPLC chromatogram, respectively, for 6-lauroyl oxycodone prepared in Example 4.
Figure 4B:
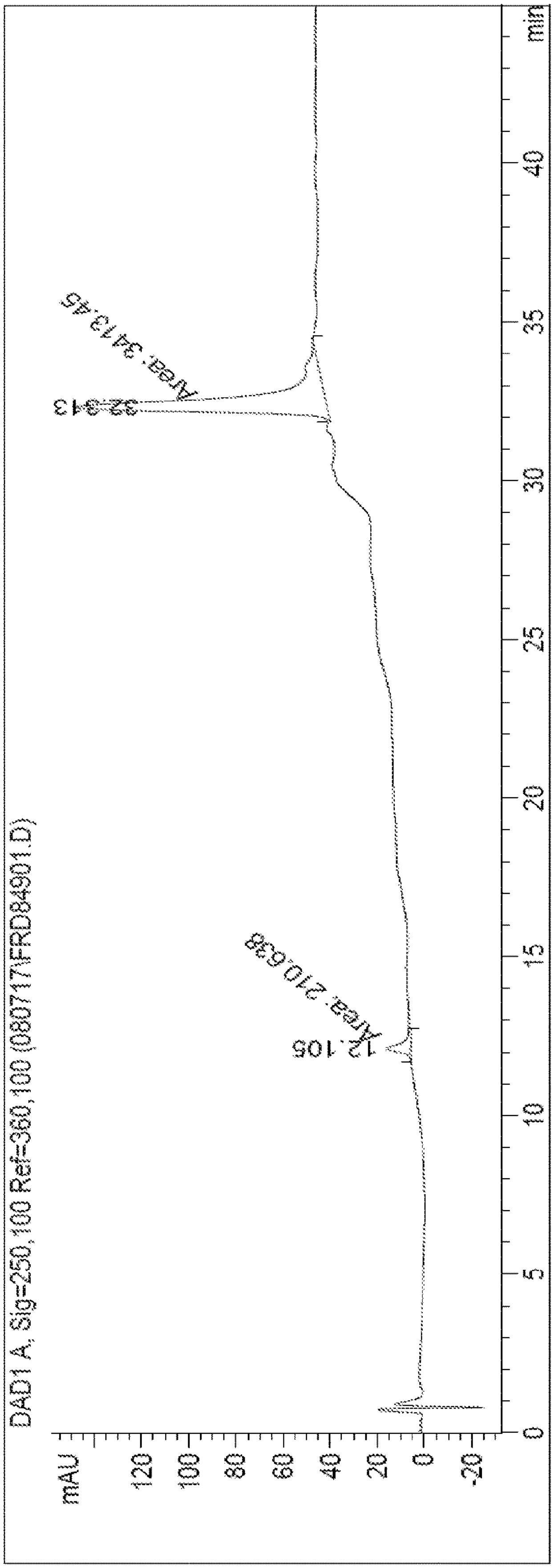

FIG. 4A and FIG. 4B depict the $^1$H NMR spectrum and the HPLC chromatogram, respectively, for the title compound.

Example 5

Preparation of 6,14-bis-valeroyl Oxycodone

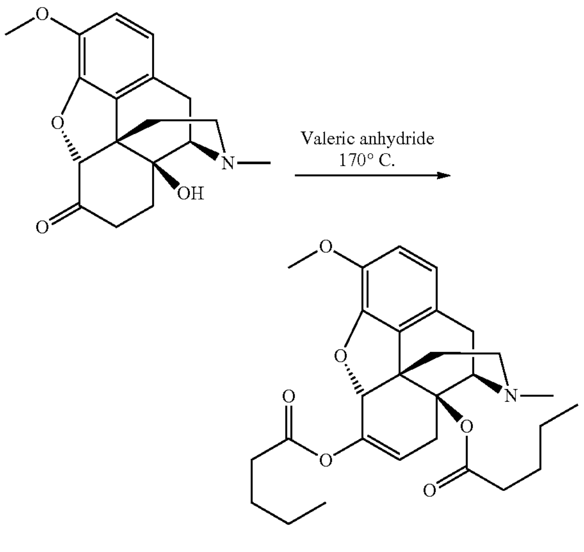

Oxycodone (0.3257 g) and valeric anhydride (4 mL) were stirred under nitrogen and heated at 170° C. for 21 hours. The mixture was then cooled and poured into water (100 mL). After stirring for two hours, the mixture was made basic with 30% ammonium hydroxide and was extracted with DCM (2×30 mL). The extract was washed with brine followed by dried over $MgSO_4$, filtration and concentration under reduced pressure.

The sample was dried on a kugelrohr still (50° C., 0.05 torr) to afford 0.56 g of a dark material. Purification by silica gel chromatography (10 g), 0.75% methanol, 0.075% conc. ammonium hydroxide in chloroform. Collected 4 mL (ten) then 8 mL fractions. Fractions 10 through 21 were analyzed by LCMS, combined and concentrated under reduced pressure affording a dark oil (0.3698 g). Yield 74%.

Figure 5A:
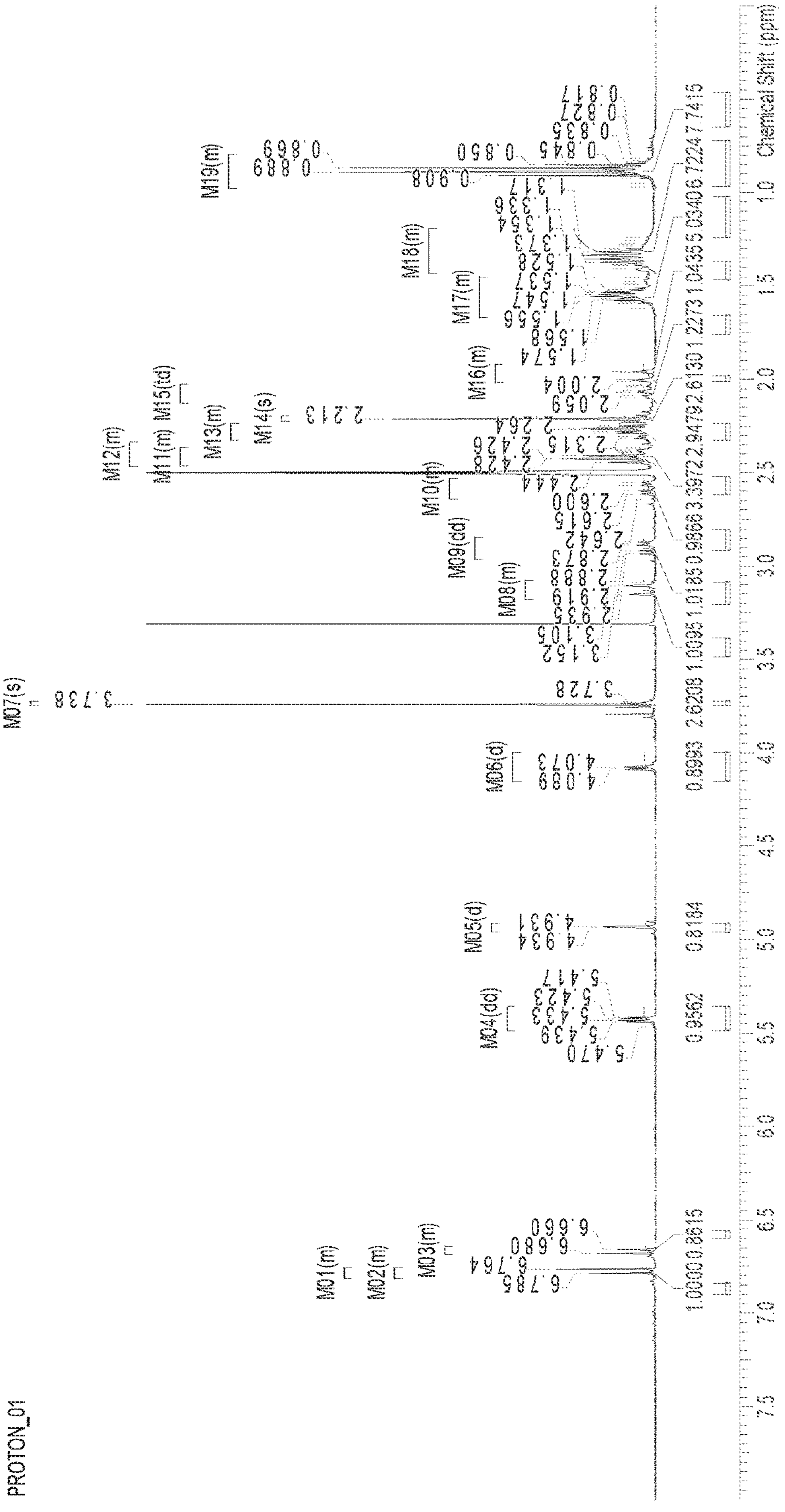
FIG. 5A and FIG. 5B depict the $^1$H NMR spectrum and the HPLC chromatogram, respectively, for 6,14-bis-valeroyl oxycodone prepared in Example 5.
Figure 5B:
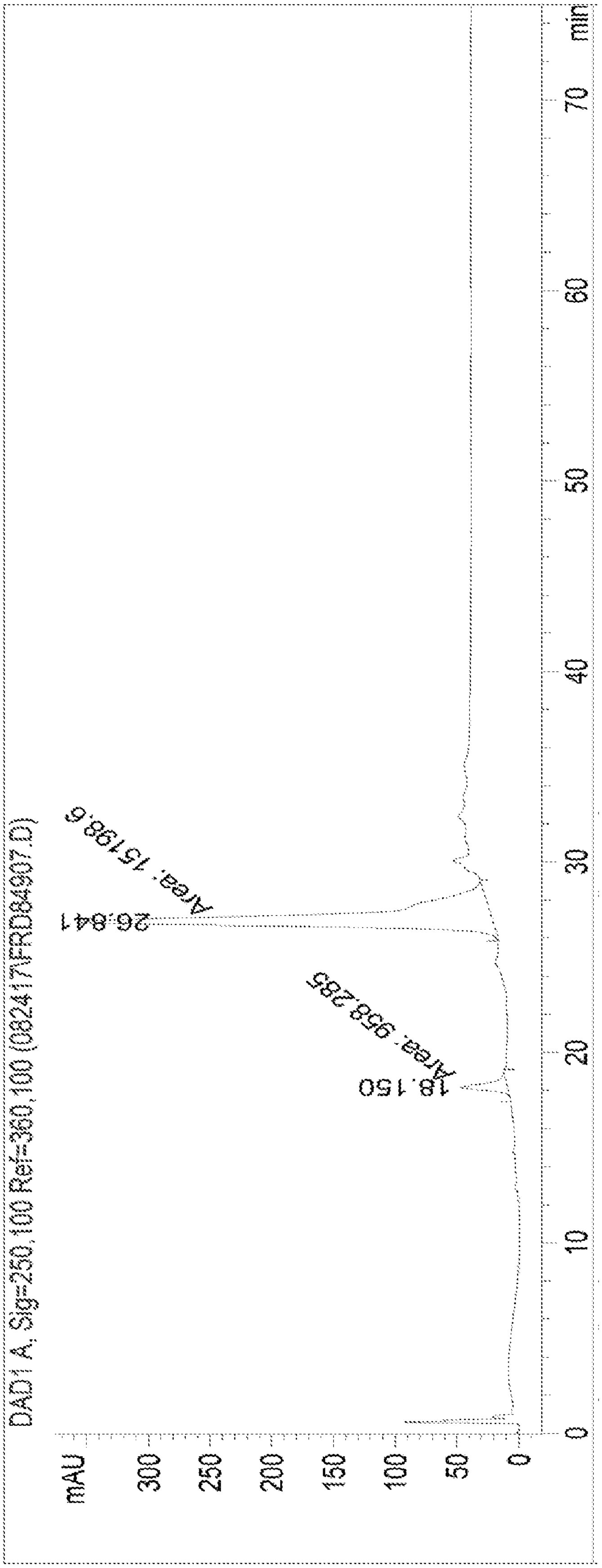

FIG. 5A and FIG. 5B depict the $^1$H NMR spectrum and the HPLC chromatogram, respectively, for the title compound.

Example 6

Hydrolysis Study of 6-acetyl Oxycodone

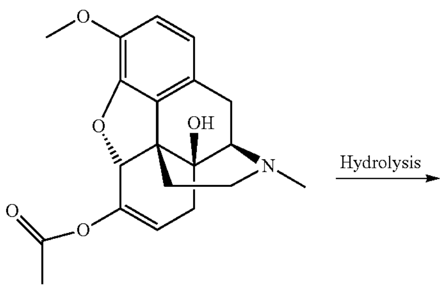

-continued

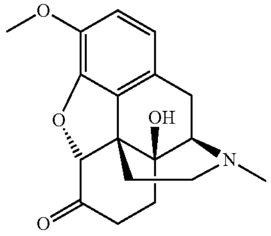

Serum, rather than plasma, was used for the test, due to reasons such as, plasma contains platelets and must be stabilized to prevent clotting; and the stabilizing chemicals can interfere with the enzymatic activity. Serum is prepared by letting fresh blood clot (about 30 minutes) then centrifuging, which removes the platelets so that chemical stabilization is not necessary. Human blood serum (pH 7.7) was used at the same day of delivery.

A simulated gastric fluid (pH≈1) and simulated intestinal fluid (pH≈6.8) were freshly prepared. Buffer solutions at various pH (4, 7, 9, 10, 11) were made according to literature. The buffer solutions were then mixed with EtOH to make a 1:1 solution (to improve solubility).

Figure 6:
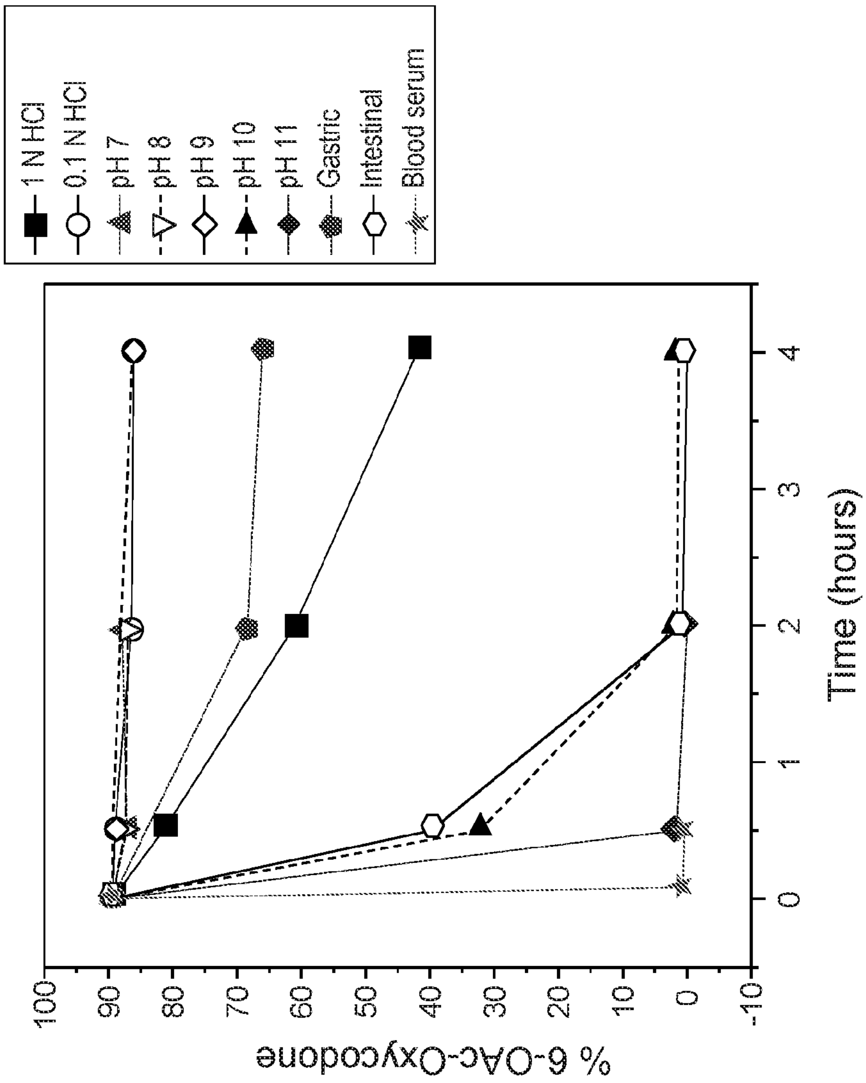
FIG. 6 depicts hydrolysis results of 6-acetyl oxycodone in different mediums set forth in Example 6.

Hydrolysis studies of 6-acetyl oxycodone ("6-OAc-Oxy") were carried out in the mediums above described. Results are presented in FIG. 6, and also summarized in the following tables (note: "Oxy" stands for oxycodone free base):

TABLE 1

Hydrolysis of 6-OAc-Oxy in human blood serum at 37° C.

| Time (hrs) | Oxy (%) | 6-OAc-Oxy (%) |
|---|---|---|
| 0 | 9.0 | 89.4 |
| 0.083 (5 min) | 97.1 | 0.65 |
| 0.5 | 98.9 | 0.39 |

TABLE 2

Hydrolysis of 6-OAc-Oxy in simulated intestinal fluid at 37° C.

| Time (hrs) | Oxy (%) | 6-OAc-Oxy (%) |
|---|---|---|
| 0 | 9.0 | 89.4 |
| 0.5 | 57.6 | 39.8 |
| 2 | 94.9 | 0.7 |
| 4 | 95.3 | 0.0 |

TABLE 3

Hydrolysis of 6-OAc-Oxy in simulated Gastric fluid at 37° C.

| Time (hrs) | Oxy (%) | 6-OAc-Oxy (%) |
|---|---|---|
| 0 | 9.0 | 89.4 |
| 2 | 17.1 | 68.4 |
| 4 | 18.4 | 66.1 |
| 8 | 22.4 | 58.1 |
| 24 | 36.3 | 46.2 |

TABLE 4

| Hydrolysis of 6-OAc-Oxy at pH = 11 buffer (1:1 EtOH:$H_2O$) | | |
|---|---|---|
| Time (hrs) | Oxy (%) | 6-OAc-Oxy (%) |
| 0 | 9.0 | 89.4 |
| 0.5 | 97.1 | 1.6 |

TABLE 5

| Hydrolysis of 6-OAc-Oxy at pH = 10 buffer (1:1 EtOH:$H_2O$) | | |
|---|---|---|
| Time (hrs) | Oxy (%) | 6-OAc-Oxy (%) |
| 0 | 9.0 | 89.4 |
| 0.5 | 65.2 | 32.3 |
| 2 | 96.8 | 1.6 |
| 4 | 98.3 | 1.2 |

TABLE 6

| Hydrolysis of 6-OAc-Oxy at pH = 9 buffer (1:1 EtOH:$H_2O$) | | |
|---|---|---|
| Time (hrs) | Oxy (%) | 6-OAc-Oxy (%) |
| 0 | 9.0 | 89.4 |
| 0.5 | 9.0 | 89.4 |
| 4 | 11.9 | 86.3 |
| 8 | 14.9 | 75.5 |
| 22 | 26.9 | 66.5 |

TABLE 7

| Hydrolysis of 6-OAc-Oxy at pH = 8 buffer (1:1 EtOH:$H_2O$) | | |
|---|---|---|
| Time (hrs) | Oxy (%) | 6-OAc-Oxy (%) |
| 0 | 9.4 | 89.4 |
| 0.5 | 10.4 | 87.4 |
| 2 | 8.8 | 87.0 |
| 26 | 20.9 | 75.3 |

TABLE 8

| Hydrolysis of 6-OAc-Oxy at pH = 7 buffer (1:1 EtOH:$H_2O$) | | |
|---|---|---|
| Time (hrs) | Oxy (%) | 6-OAc-Oxy (%) |
| 0 | 9.4 | 89.4 |
| 0.5 | 9.5 | 87.2 |
| 2 | 8.2 | 87.9 |
| 26 | 12.9 | 77.9 |

TABLE 9

| Hydrolysis of 6-OAc-Oxy at 0.1N HCl solution | | |
|---|---|---|
| Time (hrs) | Oxy (%) | 6-OAc-Oxy (%) |
| 0 | | 89.4 |
| 0.5 | 6.43 | 89.0 |
| 2 | 7.8 | 86.4 |
| 8 | 9.5 | 86.1 |
| 24 | 30.1 | 67.3 |

TABLE 10

| Hydrolysis of 6-OAc-Oxy at 1N HCl solution | | |
|---|---|---|
| Time (hrs) | Oxy (%) | 6-OAc-Oxy (%) |
| 0 | | 89.4 |
| 0.5 | 16.6 | 81.5 |
| 2 | 30.3 | 61.0 |
| 4 | 56.4 | 42.0 |
| 8 | 80.8 | 18.2 |
| 24 | 95.3 | 1.7 |

The above results show that 6-acetyl oxycodone hydrolyzed quickly in human blood serum (37° C.). 6-Acetyl oxycodone was mostly hydrolyzed to oxycodone in five minutes.

Example 7

Preparation of 6,14-bis-acetyl Oxycodone

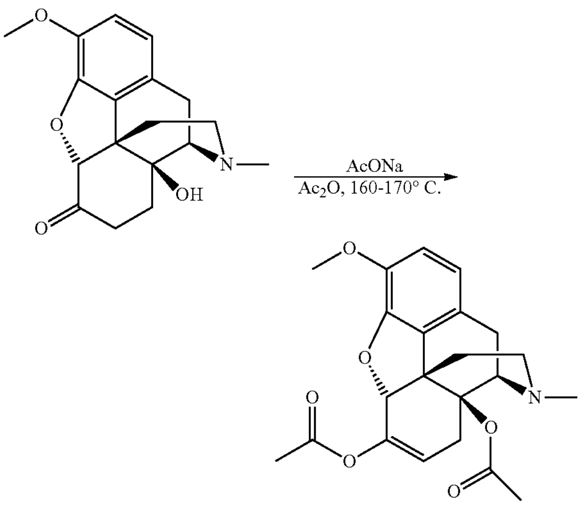

Oxycodone free base (0.4711 g, 1.49 mmol) with $Ac_2ONa$ (0.1 g, 1.22 mmol) in $Ac_2O$ (5 mL) was refluxed at 160-170° C. for 2.5 hrs. The excess $Ac_2O$ was removed under reduced pressure, and the product was precipitated with dilute ammonia solution. The filtered solid was recrystallized in EtOH to give 460 mg of the title product as a white solid. Yield: 78%.

Figure 7A:
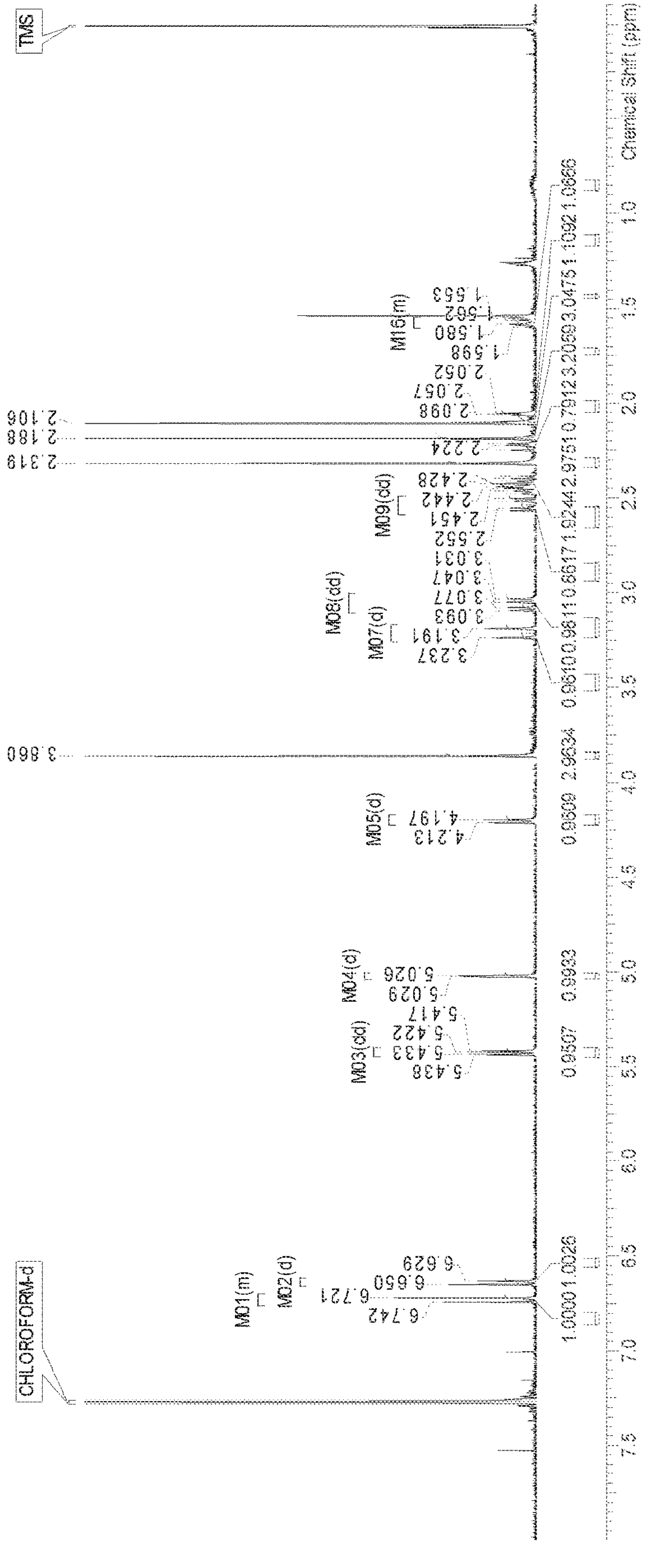
FIG. 7A and FIG. 7B depict the $^1$H NMR spectrum and the HPLC chromatogram, respectively, for 6,14-bis-acetyl oxycodone prepared in Example 7.
Figure 7B:
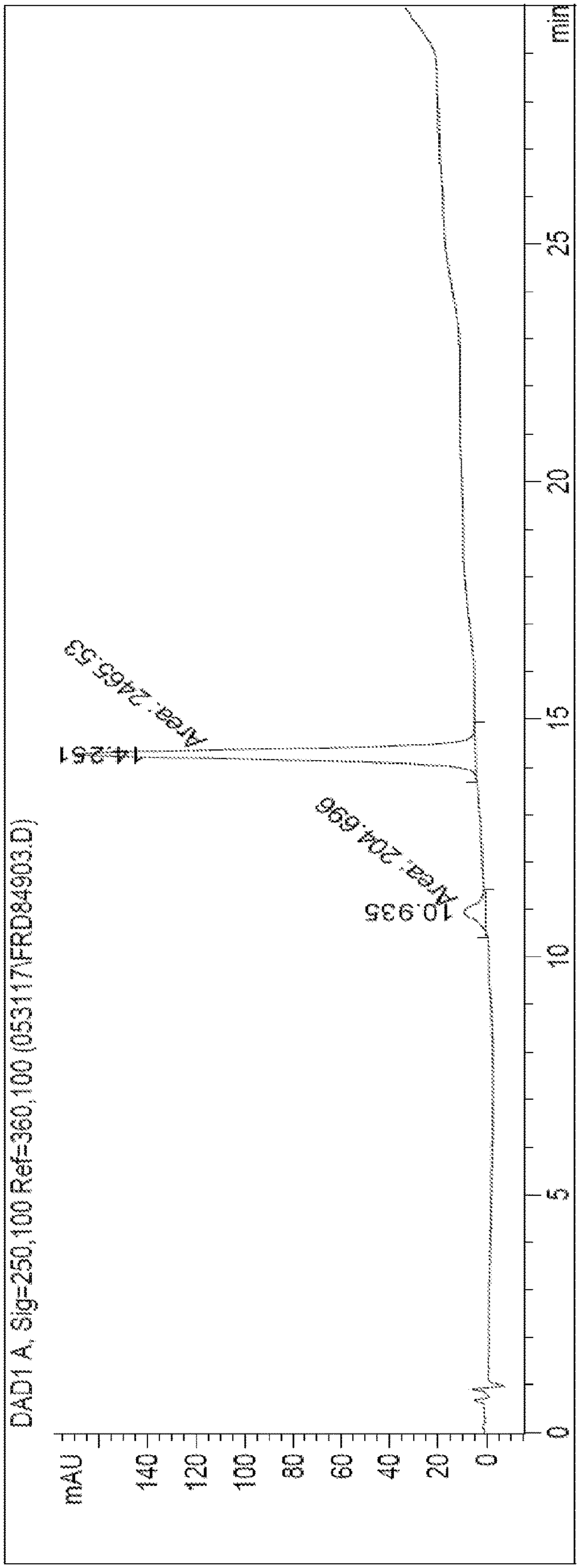

FIG. 7A and FIG. 7B depict the $^1H$ NMR spectrum and the HPLC chromatogram, respectively, for the title compound.

Example 8

A mixture of oxycodone, 6-acetyl oxycodone ("6-Acetyl"), 14-acetyl oxycodone ("14-Acetyl"), and 6,14-bis-acetyl oxycodone ("6,14-bis-Acetyl") was subjected to hydrolysis in simulated intestinal fluid (37° C., pH 6.8, pancreatine) with analysis of the hydrolyzed oxycodone and enol esters conducted by LCMS. Results from the hydrolysis are shown in Table 11.

TABLE 11

| Hydrolysis of a mixture of 6-Acetyl, 14-Acetyl, and 6,14-Diacetyl | | | | |
|---|---|---|---|---|
| | Simulated Intestinal Fluid | | | |
| | % Oxycodone | % 6-Acetyl | % 14-Acetyl | % 6,14-bis-Acetyl |
| Starting material | 11.3 | 31.7 | 2.7 | 54.0 |
| Time 0 | 22.9 | 35.7 | 8.0 | 33.4 |
| 1 hour | 78.6 | 7.2 | 14.2 | 0 |
| 2 hour | 95.1 | 0 | 4.9 | 0 |

The results show that 6-acetyl oxycodone readily hydrolyzes in the intestine releasing oxycodone in less than 2 hours. 6,14-Diacetyl oxycodone hydrolyzes to create additional 6-acetyl oxycodone and 14-acetyl oxycodone.

14-Acetyl oxycodone can be prepared, for example, by reacting oxycodone free base with acetic anhydride as described in U.S. Pat. No. 4,322,426.

Example 9

Hydrolysis Study of 6-OAc-Hydrocodone

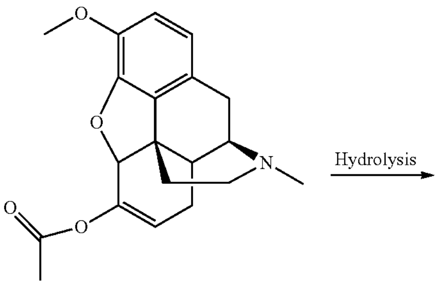

6-OAc hydrocodone

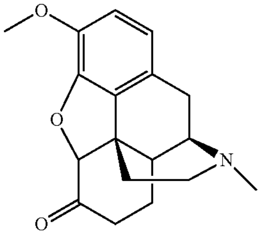

hydrocodone

Human blood serum (pH 7.7), a simulated gastric fluid (pH≈1), a simulated intestinal fluid (pH≈6.8), and buffer solutions at various pH (4, 7, 9, 10, 11) were made in the same manner as set forth in Example 6.

Figure 8:
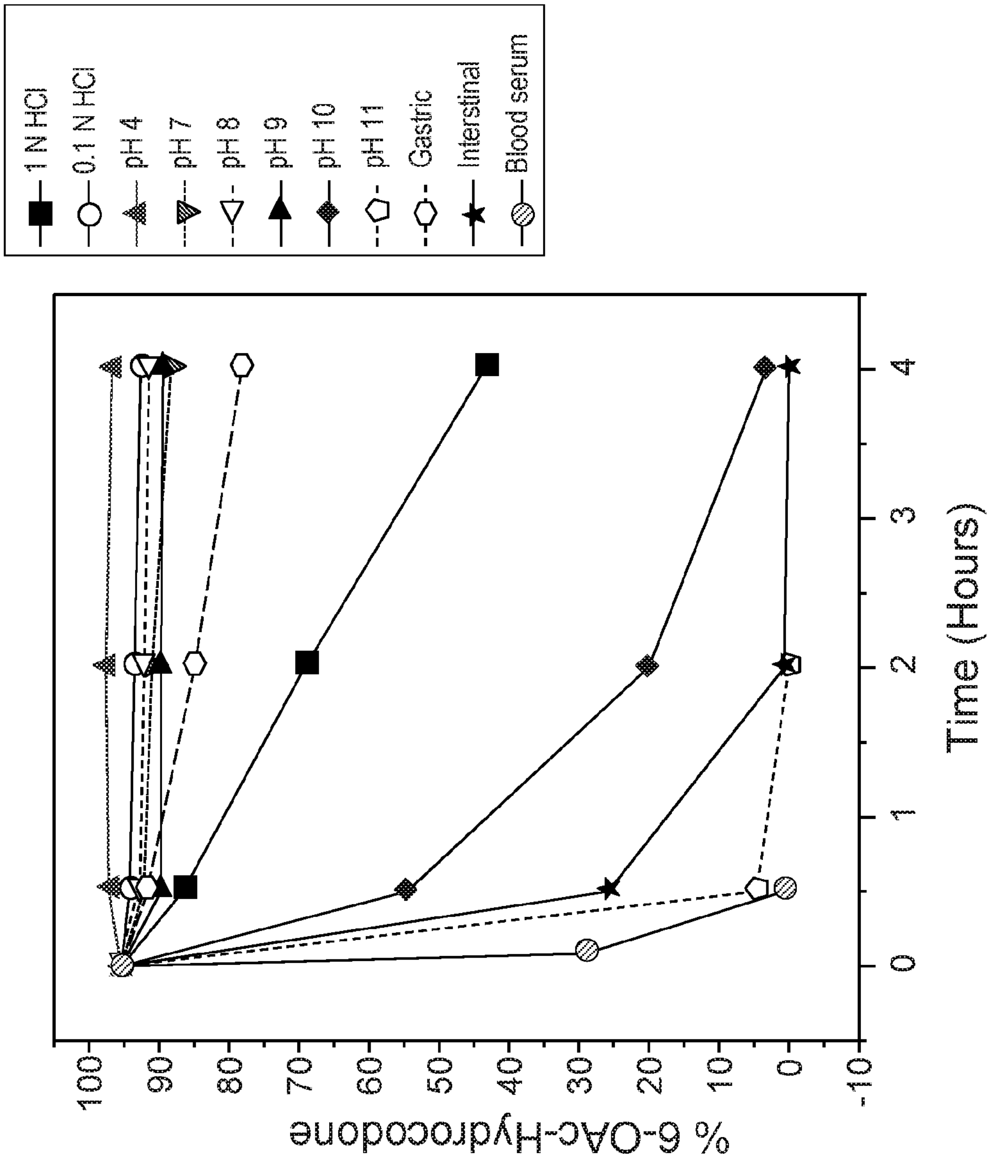
FIG. 8 depicts hydrolysis results of 6-acetyl hydrocodone in different mediums set forth in Example 9.

Hydrolysis studies of 6-acetyl hydrocodone ("6-OAc-hydrocodone") were carried out in the mediums above described. Results are presented in FIG. 8.

The results show that 6-acetyl hydrocodone hydrolyzed quickly in human blood serum (37° C.): 6-acetyl hydrocodone was 70% hydrolyzed to hydrocodone in five minutes, 99% hydrolyzed in 30 minutes.

Example 10

Preparation and Isolation of 6,14-bis-PEG-Oxycodone (as a PEG-Acid Salt)

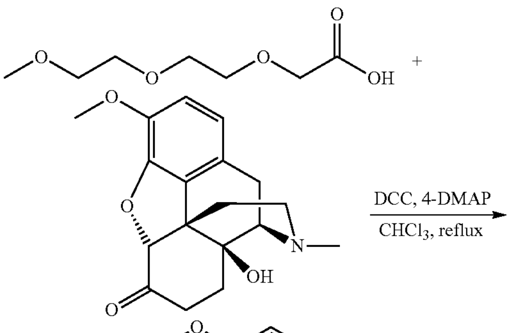

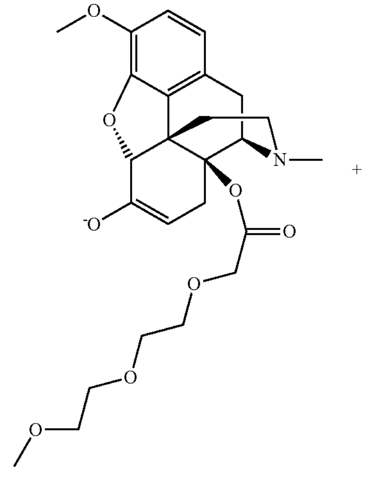

14-PEG-Oxycodone

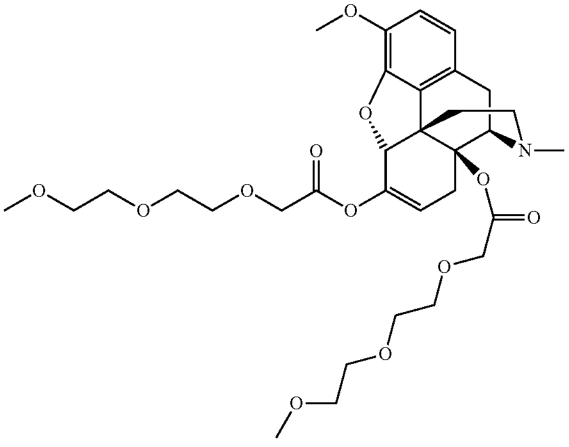

6,14-bis-PEG-Oxycodone

After the above reaction, the crude product was further purified by flash column using 80 g silica gel cartridge and 5% MeOH in EtOAc. Two batches of product were isolated.

A purer fraction contains 82 mg of 88% pure 6,14-bis-PEG-Oxycodone 2-[2-(2-methoxyethoxy)ethoxy]acetic acid salt and 12% of mono-PEG-Oxycodone with no Oxycodone. A less pure fraction contains about 251 mg of 81% pure 6,14-bis-PEG-Oxycodone 2-[2-(2-nethoxyethoxy)ethoxy] acetic acid salt, 18% of mono-PEG-Oxycodone, and 1% of Oxycodone as an impurity.

Example 11

Hydrolysis Study of 6,14-bis-PEG-Oxycodone

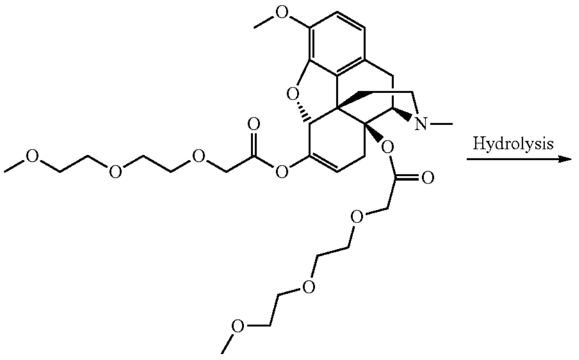

6,14-bis-PEG-Oxy

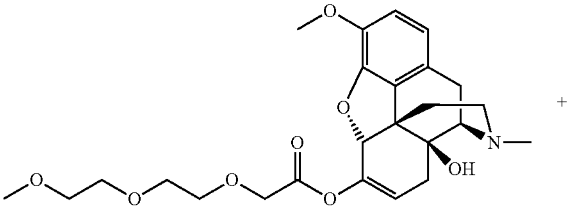

6-PEG-Oxy

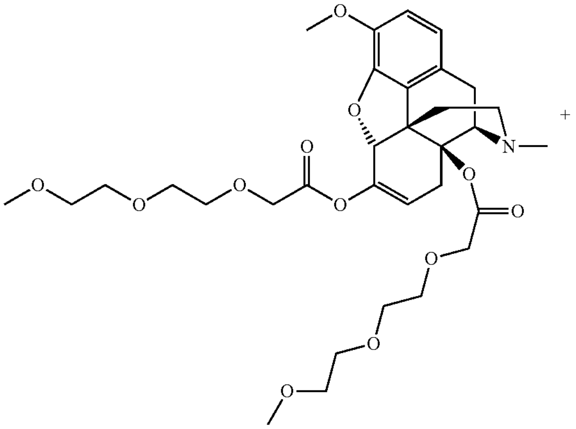

14-PEG-Oxy

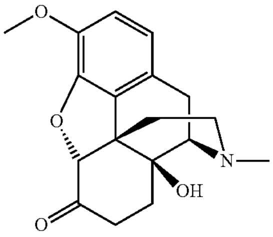

Oxycodone

Figure 9:
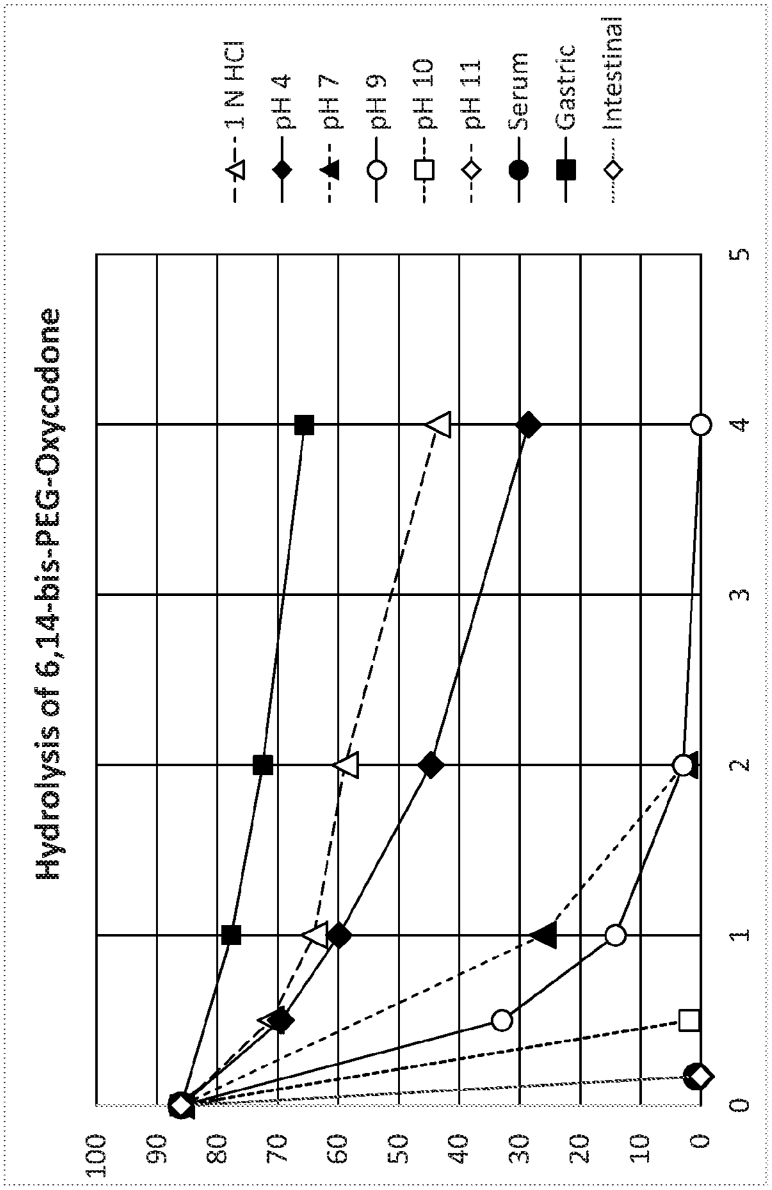
FIG. 9 depicts hydrolysis results of 6,14-bis-PEG-Oxycodone in different mediums set forth in Example 11.

The hydrolysis study of 6,14-bis-PEG-Oxycodone was started with 86% pure 6,14-bis-PEG-oxycodone and 14% pure mono-bis-PEG-oxycodone mixture. The simulated gastric fluid (pH=1.2) and simulated intestinal fluid (pH=6.8) was freshly prepared. Human blood serum (pH 7.7) was used at the same day of delivery. Buffer solutions at various pH (4, 7, 9, 10, 11) were made according to literature. The buffer solutions were then mixed with EtOH to make a 1:1 solution (to improve solubility). Results are presented in FIG. 9.

Additionally, the hydrolysis result of the starting mixture in human serum at 37° C. was summarized in Table 12, the hydrolysis result of the starting mixture in simulated gastric fluid at 37° C. was summarized in Table 13, and the hydrolysis result of the starting mixture in simulated Intestinal fluid at 37° C. was summarized in Table 14:

TABLE 12

| hydrolysis in human serum | | | | |
|---|---|---|---|---|
| Time (h) | 6,14-bis-PEG-Oxy (%) | 14-PEG-Oxy (%) | 6-PEG-Oxy (%) | Oxy (%) |
| 0 | 86 | 0 | 14 | 0 |
| 0.17 | 0.71 | 67.6 | 0 | 31.7 |
| 1 | 0 | 0 | 0 | 100 |

TABLE 13

| hydrolysis in simulated gastric fluid | | | | |
|---|---|---|---|---|
| Time (h) | 6,14-bis-PEG-Oxy (%) | 14-PEG-Oxy (%) | 6-PEG-Oxy (%) | Oxy (%) |
| 0 | 86 | 0 | 14 | 0 |
| 1 | 77.7 | 11.1 | 9.2 | 2.0 |
| 2 | 72.5 | 15.3 | 9.2 | 3.1 |
| 4 | 65.6 | 21.1 | 9.0 | 4.3 |
| 20 | 30.2 | 57.6 | 0 | 12.1 |

TABLE 14

| Hydrolysis in simulated Intestinal fluid | | | | |
|---|---|---|---|---|
| Time (h) | 6,14-bis-PEG-Oxy (%) | 14-PEG-Oxy (%) | 6-PEG-Oxy (%) | Oxy (%) |
| 0 | 86 | 0 | 14 | 0 |
| 0.17 | 0 | 0 | 2.4 | 97.6 |

Example 12

Hydrolysis Study of 6-lauroyl-Oxycodone

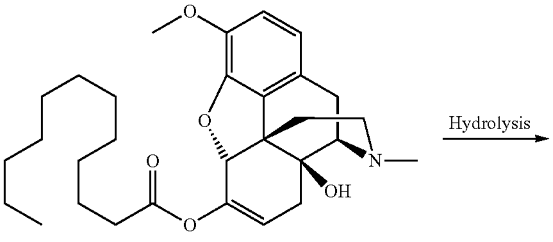

6-lauroyl oxycodone

-continued

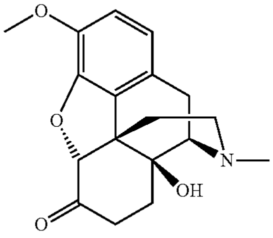

Oxycodone

The hydrolysis study of 6-lauroyl-Oxycodone was started with 99% pure 6-lauroyl-Oxycodone. The pH 11 and pH 9 buffer used for the hydrolysis study contains 75% EtOH to increase the solubility of 6-lauroyl-Oxycodone. The simulated intestinal fluid used for hydrolysis was freshly prepared. 0.5% Polysorbate 80 was added to the intestinal fluid as an emulsifier to help 6-lauroyl-Oxycodone evenly distributed.

The hydrolysis results of 6-lauroyl-Oxycodone in pH 11 and pH 9 buffers and in simulated intestinal fluid with 0.5% Polysorbate 80 at 37° C. are presented in Tables 15-17.

TABLE 15

| In pH 11 buffer | | |
|---|---|---|
| Time (h) | 6-lauroyl-Oxy (%) | Oxy (%) |
| 0 | 99 | 0 |
| 0.5 | 24.5 | 75.5 |
| 4 | 7.2 | 92.8 |
| 8 | 6.2 | 93.8 |

TABLE 16

| In pH 9 buffer | | |
|---|---|---|
| Time (h) | 6-lauroyl-Oxy (%) | Oxy (%) |
| 0 | 99 | 0 |
| 0.5 | 98 | 1 |
| 2 | 98 | 1 |
| 4 | 98 | 1 |
| 8 | 98 | 1 |

TABLE 17

| In simulated intestinal fluid | | |
|---|---|---|
| Time (h) | 6-lauroyl-Oxy (%) | Oxy (%) |
| 0 | 99 | 0 |
| 0.17 | 56.9 | 43.1 |
| 0.5 | 54.8 | 45.2 |
| 1 | 52.6 | 47.4 |
| 2 | 50.8 | 49.2 |
| with additional fresh intestinal fluid 30 min | 18.6 | 81.4 |

Example 13

Hydrolysis Study of 6,14-bis-lauroyl-Oxycodone

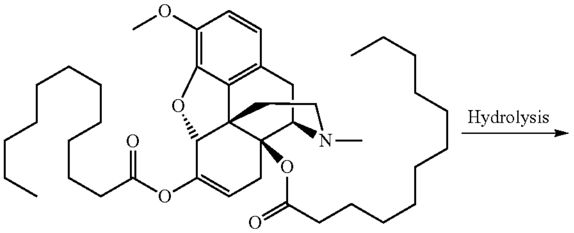

6,14-bis-lauroyl-Oxy

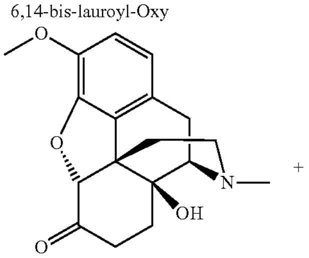

Oxy

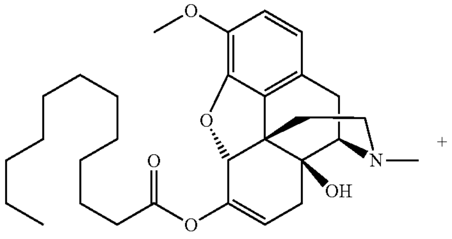

6-lauroyl-Oxy

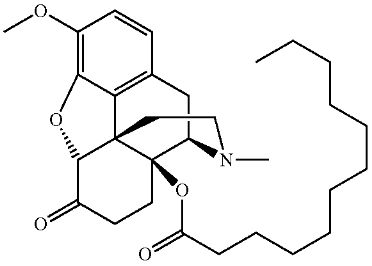

14-lauroyl-Oxy

The hydrolysis study of 6,14-bis-lauroyl-Oxycodone was started with 99% pure product. The pH 11, pH 9, pH 7 buffer solutions and 1.0 N HCl solution used for the hydrolysis study contains 75% EtOH to increase the solubility of 6,14-bis-lauroyl-Oxycodone.

The hydrolysis results in the buffer solutions and in the 1.0 N HCl solution are presented in Tables 18-21.

TABLE 18

| In pH 11 buffer | | | |
|---|---|---|---|
| Time (h) | 6,14-bis-lauroyl-Oxy (%) | mono-lauroyl-Oxy (%) | Oxy (%) |
| 0 | 99 | 0 | 0 |
| 0.17 | 83.7 | 16.3 | 0.5 |
| 0.5 | 63.9 | 33.1 | 1 |

TABLE 18-continued

| In pH 11 buffer | | | |
|---|---|---|---|
| Time (h) | 6,14-bis-lauroyl-Oxy (%) | mono-lauroyl-Oxy (%) | Oxy (%) |
| 2 | 14.7 | 60.5 | 2.8 |
| 8.5 | 0 | 94.6 | 5.4 |
| 22.5 | 0 | 89.8 | 10.2 |

TABLE 19

| In pH 9 buffer | | | |
|---|---|---|---|
| Time (h) | 6,14-bis-lauroyl-Oxy (%) | mono-lauroyl-Oxy (%) | Oxy (%) |
| 0 | 99 | 0 | 0 |
| 0.5 | 98.7 | 1.3 | 0 |
| 2 | 98.4 | 1.6 | 0 |
| 8.5 | 96.2 | 3.8 | 0 |
| 22.5 | 93.4 | 6.6 | 0 |

TABLE 20

| In pH 7 buffer | | | |
|---|---|---|---|
| Time (h) | 6,14-bis-lauroyl-Oxy (%) | mono-lauroyl-Oxy (%) | Oxy (%) |
| 0 | 99 | 0 | 0 |
| 0.5 | 98 | 1 | 0 |
| 2 | 98 | 2 | 0 |
| 4 | 98 | 2 | 0 |
| 8 | 98 | 2 | 0 |
| 24 | 94.3 | 5.7 | 0 |

TABLE 21

| In 1.0N HCl | | | |
|---|---|---|---|
| Time (h) | 6,14-bis-lauroyl-Oxy (%) | mono-lauroyl-Oxy (%) | Oxy (%) |
| 0 | 99 | 0 | 0 |
| 0.5 | 97 | 2.9 | 0 |
| 2 | 95.1 | 4.7 | 0 |
| 4 | 94 | 6 | 0 |
| 8 | 91.4 | 8.6 | 0 |
| 24 | 77.1 | 22.9 | 0 |

Mono-lauroyl-oxycodone (e.g., 6-lauroyl-Oxycodone) can further be purified by the following HPLC method:

Column: Biotage C18HS 12M 0667-1 (10 gram)

Aqueous buffer: 0.14 g ammonium formate and two drops conc. ammonium hydroxide in water (1 L)

Conditions: 1:1 buffer/methanol, four 12-mL fractions

1:3 buffer methanol, eight 12-mL fractions

Methanol, remaining fractions

Fractions were analyzed by LCMS (isocratic methanol, 3 min. run).

Example 14

Isolation and Purification of 14-lauroyl Oxycodone

Isolation of 14-lauroyl oxycodone: A 200-mg sample of 6,14-bis-lauroyl oxycodone with about 10% 14-lauroyl oxycodone was used to isolate a sample of 14-lauroyl oxycodone by reverse phase flash chromatography:

Column: Biotage C18HS 12M 0667-1 (10 gram);

Aqueous buffer: 0.14 g ammonium formate and two drops conc. ammonium hydroxide in water (1 L);

Conditions:

1:1 buffer/methanol, eight 12-mL fractions,

1:3 buffer methanol, eight 12-mL fractions, and

Methanol, remaining fractions.

Figure 10:
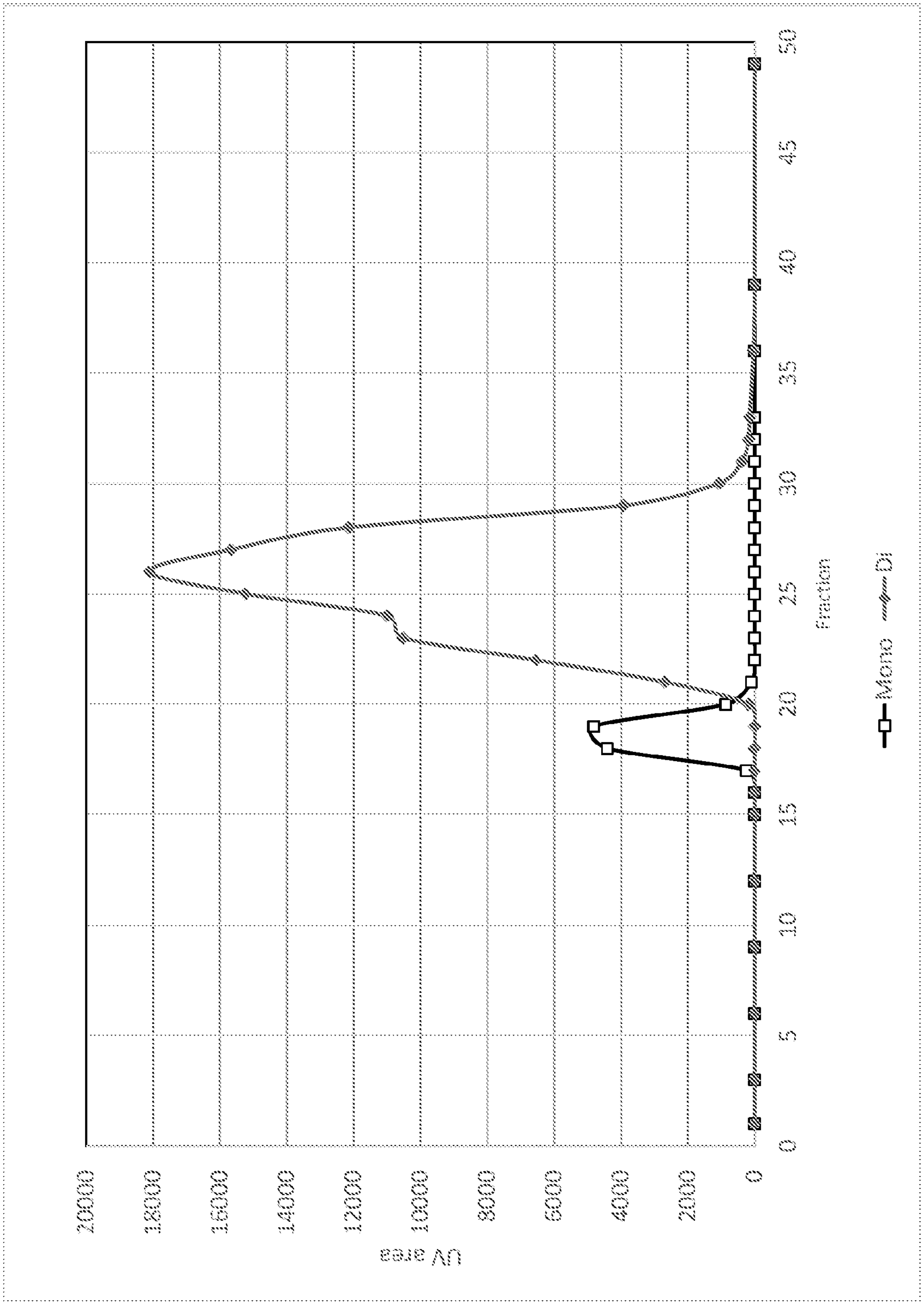
FIG. 10 depicts the RP Flash Chromatogram obtained in isolating 14-lauroyl oxycone from a mixture of 6,14-bis-lauroyl oxycodone and 14-lauroyl oxycodone described in Example 14.

The fractions were analyzed by LCMS (isocratic methanol). Fractions 18 and 19 were combined and concentrated under reduced pressure (0.4 tor) affording the pure 14-lauroyl oxycodone (9.1 mg). LCMS analysis showed no impurities, $[M+H]^+=498$. FIG. 10 depicts the RP Flash Chromatogram for this method, where "Mono" refers to 14-lauroyl oxycodone and "Di" refers to 6,14-bis-lauroyl oxycodone.

Figure 11:
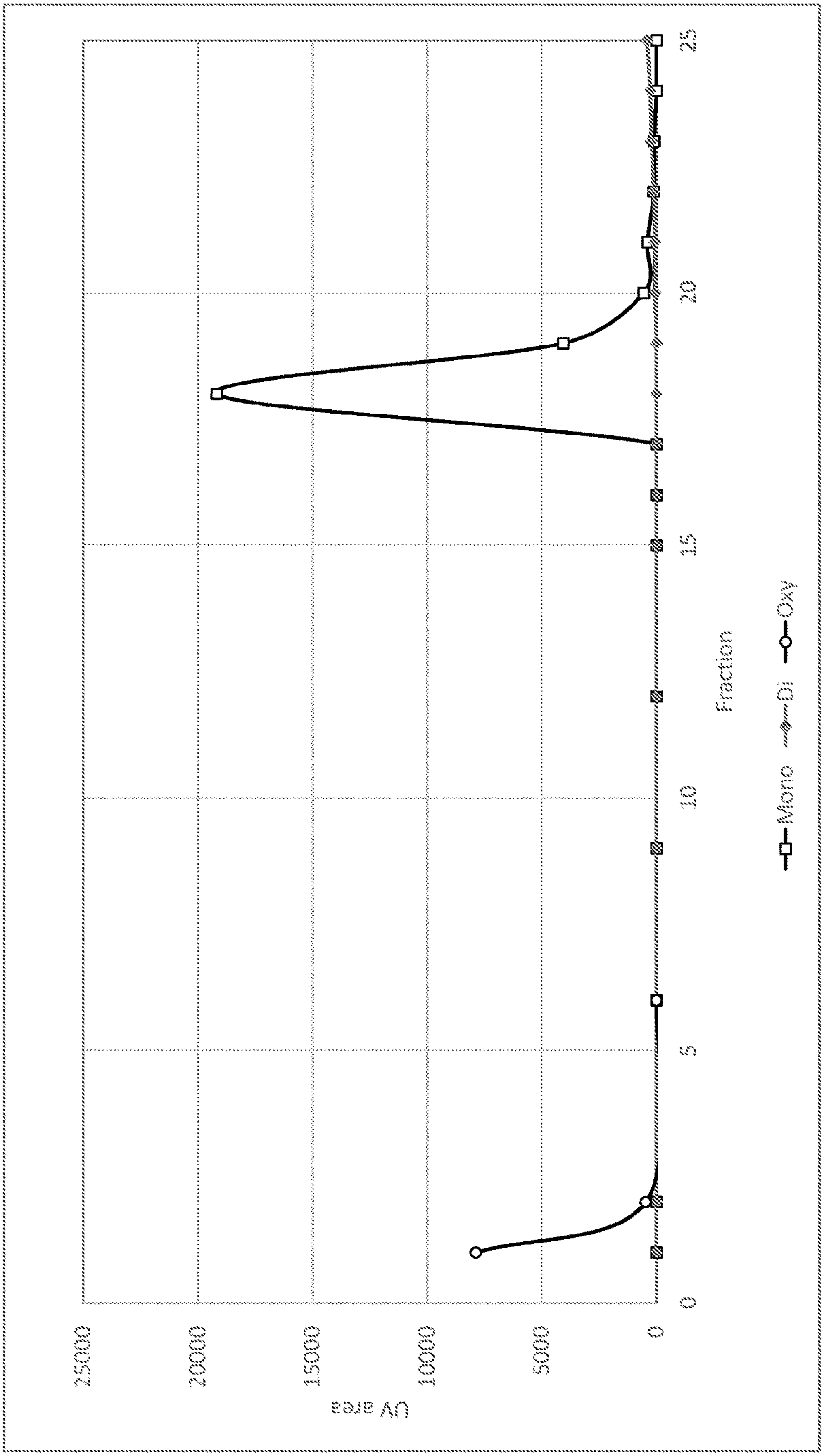
FIG. 11 depicts the RP Flash Chromatogram obtained in purifying 14-lauroyl oxycodone from a mixture of 14-lauroyl oxycodone and oxycodone described in Example 14.

Purification of 14-lauroyl oxycodone:

The above method was used to separate a 200-mg mixture of 14-lauroyl oxycodone and oxycodone. Fractions 18 and 19 were combined and concentrated under reduced pressure (0.4 tor) affording the 14-lauroyl oxycodone (47.3 mg). FIG. 11 depicts the RP Flash Chromatogram for this method, where "Mono" refers to 14-lauroyl oxycodone, "Di" refers to 6,14-bis-lauroyl oxycodone, and "Oxy" refers to oxycodone.

Example 15

μ-Opioid Receptor Binding Assay

The μ-opioid receptor binding activity of the compounds listed in Table 22 was tested according to the radioligand binding assay procedure described above in the section titled "μ-Opioid Receptor Binding Assay Procedures."

TABLE 22

| Compound Name | Compound Structure | $K_i$ (μM) |
|---|---|---|
| 6-acetyl oxycodone | 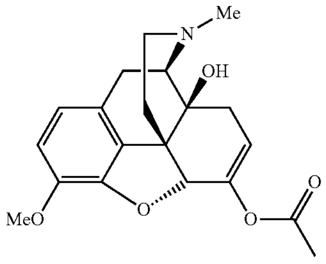 | 0.041 |

TABLE 22-continued
| Compound Name | Compound Structure | $K_i$ (μM) |
|---|---|---|
| 14-acetyl oxycodone | 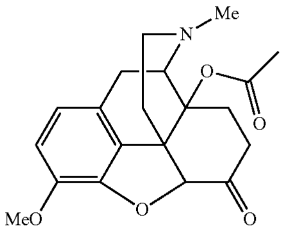 [SMILES: COc1ccc2c3c1OC1C(=O)CCC4(OC(C)=O)C(C2)N(C)CCC314] | 0.018 |
| 6-PEG oxycodone | 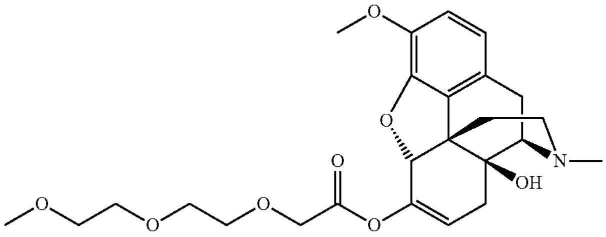 | 0.022 |
| 6,14-bis-PEG oxycodone | 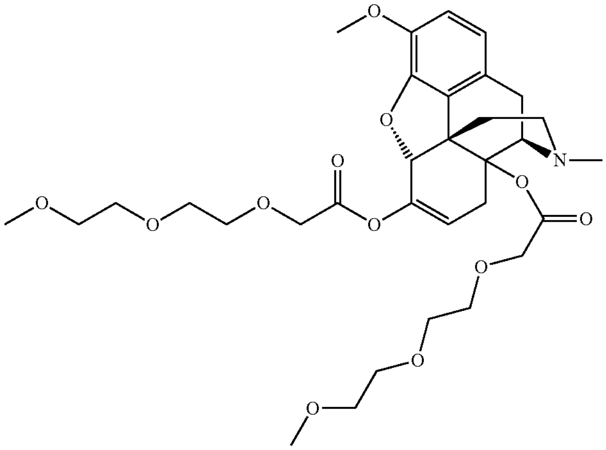 | 0.052 |
| 6-lauroyl oxycodone | 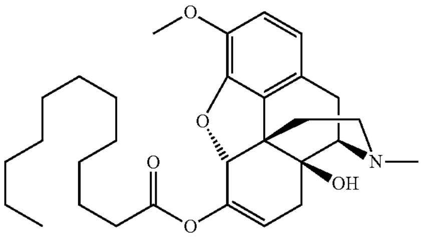 | 0.096 |
| 14-lauroyl oxycodone | 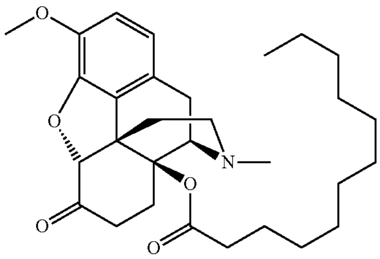 | 0.16 |

TABLE 22-continued

| Compound Name | Compound Structure | $K_i$ (μM) |
|---|---|---|
| 6,14-bis-lauroyl oxycodone | 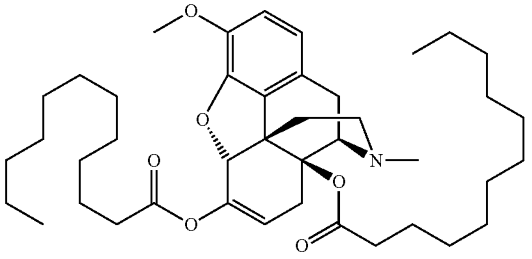 | 22.2 |
| oxycodone | | 0.030 |

The results of the binding assay show that the binding constants ($K_i$) of 6-substituted enol esters, such as 6-acetyl oxycodone, 6-PEG oxycodone, and 6-lauroyl oxycodone, are comparable to the $K_i$ of 0.030 obtained for the parent opioid, oxycodone. Also the $K_i$ of the medium chain 6,14-bis-substituted enol ester, 6,14-bis-PEG oxycodone, is comparable to that of oxycodone. The $K_i$ of a short chain 14-substituted enol ester of a compound of Formula VI, such as the exemplary 14-acetyl oxycodone, is lower than that for oxycodone. When compounds having substitution patterns similar to the compounds mentioned above are made bioavailable only in the lower gastrointestinal tract, they convert to oxycodone within a certain extent of time to provide μ-opioid agonist functions from both the enol ester prodrugs and the parent oxycodone.

The $K_i$ of 14-lauroyl oxycodone, i.e., an exemplary compound of a long chain mono 14-substituted enol ester of compounds of Formula VI, is higher than that for oxycodone.

The $K_i$ of 6,14-bis-lauroyl oxycodone, i.e., an exemplary compound of a long chain 6,14-bis-substituted enol ester of compounds of Formula V, is significantly higher than that for oxycodone. Accordingly, these type of compounds do not bind well to μ-opioid receptor prior to the hydrolysis in the intestine to its parent opioid compound.

Example 16

μ-Opioid Receptor Functional Assay

The compounds listed in Table 22 in Example 15, except for 6,14-bis-lauroyl oxycodone, were tested in a [$^{35}$S]GTPγS functional assay to evaluate whether the compounds tested agonize or antagonize the μ-receptor. The functional test was run using freshly thawed μ-receptor membranes prepared from a cell line expressing recombinant μ-opioid receptor in a CHO-K 1 cell background as described above in the second paragraph of the section titled "μ-Opioid Receptor Functional Assay Procedures." The results of the functional assay are provided in Table 23.

TABLE 23

| Compound Name | Conc. Criteria | % Response Agonist | % Response Antagonist | $IC_{50}/EC_{50}$ |
|---|---|---|---|---|
| 14-lauroyl oxycodone | 100 μM ≥± 50% | 56% | NA | 1.15 μM |
| 14-lauroyl oxycodone | 100 μM ≥± 50% | NA | 56% | 18.8 μM |

TABLE 23-continued

| Compound Name | Conc. Criteria | % Response Agonist | % Response Antagonist | $IC_{50}/EC_{50}$ |
|---|---|---|---|---|
| 14-acetyl oxycodone | 3 μM ≥± 50% | 79% | ND | 0.66 μM |
| 6,14-bis-PEG oxycodone | 3 μM ≥± 50% | 85% | ND | 0.52 μM |
| 6-lauroyl oxycodone | 3 μM ≥± 50% | 52% | ND | 0.99 μM |
| 6-acetyl oxycodone | 3 μM ≥± 50% | 62% | ND | 1.69 μM |
| 6-PEG oxycodone | 3 μM ≥± 50% | 90% | ND | 0.39 μM |
| Oxycodone hydrochloride | 3 μM ≥± 50% | 82% | ND | 0.65 μM |

NA = not applicable; ND = not determined

As described in Example 15, 6,14-bis-lauroyl oxycodone does not bind to μ-opioid receptor well. Therefore, the $EC_{50}$ value could not be determined for this compound in the functional assay in the studied concentration range.

It can be concluded from the results of Table 23 that the 6-substituted enol esters are agonists of μ-opioid receptor. 14-Acetyl oxycodone and 6,14-bis-PEG oxycodone are also μ-receptor agonist as effective as oxycodone. 14-Lauroyl oxycodone is a partial agonist and a partial antagonist of μ-opioid receptor though somewhat weaker agonist than oxycodone and much weaker antagonist than naltrexone ($IC_{50}$=15.2 nM). Naltrexone was used as a positive control in the assessment of the antagonist activity of 14-lauroyl oxycodone.

The disclosure also relates to the following particular embodiments:

Embodiment 1. A compound of Formula I:

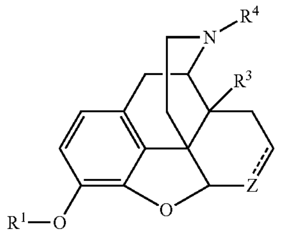

I and a pharmaceutically acceptable salt or solvate thereof, wherein:

$R^1$ is H; alkyl optionally substituted with 1, 2, or 3 substituents, each independently selected from the group consisting of hydroxy, halo, haloalkyl, amino, alkylamino, dialkylamino, carboxy, alkoxy, and alkoxycarbonyl; -PEG-$R^7$; or a hydroxyl protecting group PG selected from the group consisting of alkyl, arylalkyl, heterocyclo, (heterocyclo)alkyl, acyl, silyl, and carbonate, any of which is optionally substituted;

Z is C—$OR^2$ or C(═O);

⫽ is single bond or a double bond, provided that ⫽ is a single bond when Z is C(═O) and ⫽ is a double bond when Z is C—$OR^2$;

$R^2$ is C(═O)$R^5$ or -PEG-$R^7$, wherein $R^5$ is selected from the group consisting of unsubstituted $C_{1-12}$ alkyl, unsubstituted $C_{2-12}$ alkenyl, unsubstituted $C_{2-12}$ alkynyl, —$CH_2$—O—$(CH_2CH_2O)_m$—$R^7$, —O—$(CH_2CH_2O)_n$—$R^7$, —NH—$(CH_2CH_2O)_p$—$R^7$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; and wherein the 6-membered heterocycle group is attached to the carbonyl carbon of $R^2$ through a carbon atom or through a nitrogen atom;

$R^3$ is hydrogen, OH, —Y-PEG-$R^7$, or —OC(═O)$R^6$, wherein

Y is a covalent bond or a linker;

$R^6$ is selected from the group consisting of unsubstituted $C_{1-12}$ alkyl, unsubstituted $C_{2-12}$ alkenyl, unsubstituted $C_{2-12}$ alkynyl, —$CH_2$—O—$(CH_2CH_2O)_m$—$R^7$, —O—$(CH_2CH_2O)_n$—$R^7$, —NH$(CH_2CH_2O)_p$—$R^7$, phenyl, benzyl, phenethyl, pyridyl, cycloalkyl, (cycloalkyl)alkyl, cycloalkenyl, (cycloalkenyl)alkyl, 6-membered heterocycle, and (5- or 6-membered heterocycle)alkyl, wherein the phenyl, pyridyl, cycloalkyl, cycloalkenyl, and heterocycle moiety is optionally substituted with 1, 2, or 3 substituents, each independently selected from the group consisting of alkyl, hydroxy, halo, haloalkyl, amino, alkylamino, dialkylamino, carboxy, alkoxy, and alkoxycarbonyl; and wherein the 6-membered heterocycle group is attached to the carbonyl carbon through a carbon atom or through a nitrogen atom;

provided that $R^3$ is —OC(═O)$R^6$ when Z is C(═O);

PEG is one ethylene oxide unit or an oligomer of 2 or more ethylene oxide subunits;

$R^7$ is selected form the group consisting of hydrogen, $C_{1-6}$ alkyl, aryl, heteroaryl, cycloalkyl, and heterocyclo, any of which is optionally substituted;

$R^4$ is selected from the group consisting of hydrogen, alkyl, alkenyl, alkynyl, cycloalkyl, and (cycloalkyl) alkyl, any of which is optionally substituted with 1, 2, or 3 substituents, each independently selected from the group consisting of hydroxy, halo, haloalkyl, amino, alkylamino, dialkylamino, carboxy, alkoxy, and alkoxycarbonyl;

m is an integer between 1 and 9;

n and p are each independently an integer between 1 and 20; and provided that at least one of $R^2$ and $R^3$ is —C(═O)$R^5$ and —OC(═O)$R^6$, respectively; with the following provisos:

1) the compound is not

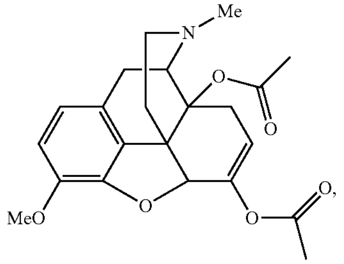

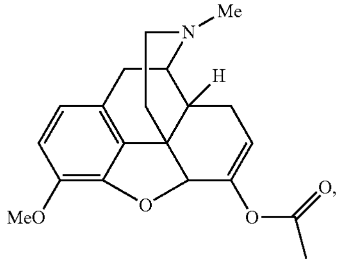

or

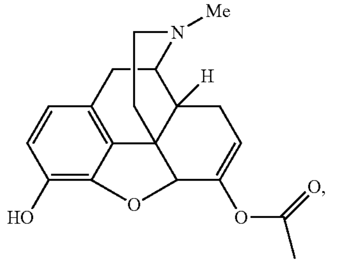

2) when $R^1$ is unsubstituted alkyl, $R^3$ is hydrogen, and $R^4$ is unsubstituted alkyl, then $R^5$ is other than optionally substituted phenyl or optionally substituted pyridyl, or 3) when $R^1$ is unsubstituted alkyl, $R^4$ is unsubstituted alkyl, and $R^3$ is —OC(═O)$R^6$, then both $R^5$ and $R^6$ are other than optionally substituted pyridyl.

Embodiment 2. The compound of Embodiment 1, having the Formula II:

II

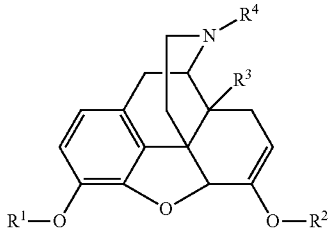

or a pharmaceutically acceptable salt or solvate thereof.

Embodiment 3. The compound of Embodiment 1 or 2, having the Formula III:

III

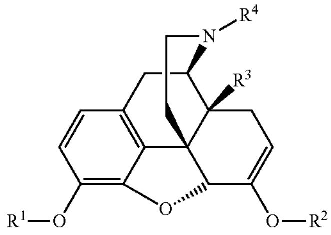

or a pharmaceutically acceptable salt or solvate thereof, wherein $R^1$, $R^2$, $R^3$, and $R^4$ are as defined in Embodiment 1.

Embodiment 4. The compound of Embodiment 1 or 2, having the Formula IV:

IV

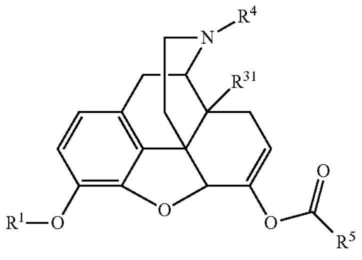

or a pharmaceutically acceptable salt or solvate thereof, wherein $R^1$, $R^4$, and $R^5$ are as defined in Embodiment 1, and $R^{31}$ is hydrogen or OH.

Embodiment 5. The compound of Embodiment 1 or 2, having the Formula V:

V

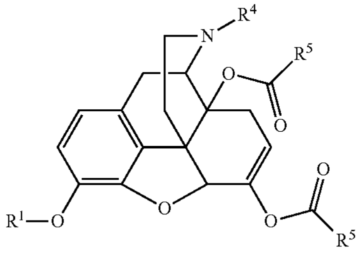

or a pharmaceutically acceptable salt or solvate thereof, wherein $R^1$, $R^4$, and $R^5$ are as defined in Embodiment 1.

Embodiment 6. The compound of Embodiment 1, having the Formula VI:

VI

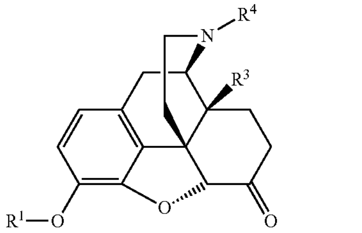

or a pharmaceutically acceptable salt or solvate thereof, wherein $R^1$ and $R^4$ are as defined in claim 1 and $R^3$ is $-OC(=O)R^6$, wherein $R^6$ is as defined in Embodiment 1.

Embodiment 7. The compound of any one of Embodiments 1-6, or a pharmaceutically acceptable salt or solvate thereof, wherein $R^1$ is H or alkyl optionally substituted with 1, 2, or 3 substituents, each independently selected from the group consisting of hydroxy, halo, haloalkyl, amino, alkylamino, dialkylamino, carboxy, alkoxy, and alkoxycarbonyl.

Embodiment 8. The compound of Embodiment 7, or a pharmaceutically acceptable salt or solvate thereof, wherein $R^1$ is H or unsubstituted $C_{1-6}$ alkyl.

Embodiment 9. The compound of any one of Embodiments 1-6, or a pharmaceutically acceptable salt or solvate thereof, wherein $R^1$ is -PEG-$R^7$, wherein $R^7$ is as defined in claim 1 and PEG is $-(CH_2CH_2O)_q-$, wherein q varies from 1 to 50.

Embodiment 10. The compound of any one of Embodiments 1-6, or a pharmaceutically acceptable salt or solvate thereof, wherein $R^1$ is PG and said PG is selected from the group consisting of methyl, tert-butyl, optionally substituted benzyl, optionally substituted benzoyl, acetyl, trimethyl silyl, tert-butyldimethyl silyl, tert-butyldiphenyl silyl, and tri-isopropyl silyl.

Embodiment 11. The compound of any one of Embodiments 1-3 and 7-10, or a pharmaceutically acceptable salt or solvate thereof, wherein $R^3$ is hydrogen.

Embodiment 12. The compound of any one of Embodiments 1-3 and 7-10, or a pharmaceutically acceptable salt or solvate thereof, wherein $R^3$ is OH.

Embodiment 13. The compound of any one of Embodiments 1-3 and 7-10, or a pharmaceutically acceptable salt thereof, wherein $R^3$ is —Y-PEG-$R^7$ and $R^2$ is $-C(=O)R^5$, wherein Y, PEG, $R^7$ and $R^5$ are as defined in Embodiment 1.

Embodiment 14. The compound of any one of Embodiments 1-3 and 7-10, or a pharmaceutically acceptable salt or solvate thereof, wherein $R^3$ is $-OC(=O)R^6$, wherein $R^6$ is as defined in Embodiment 1.

Embodiment 15. The compound of any one of Embodiments 1-14, or a pharmaceutically acceptable salt or solvate thereof, wherein $R^4$ is unsubstituted $C_{1-6}$ alkyl.

Embodiment 16. The compound of any one of Embodiments 1-15, or a pharmaceutically acceptable salt or solvate thereof, wherein $R^4$ is methyl.

Embodiment 17. The compound of any one of Embodiments 6 and 14-16, or a pharmaceutically acceptable salt or solvate thereof, wherein $R^6$ is unsubstituted $C_{1-6}$ alkyl, provided that the compound is not

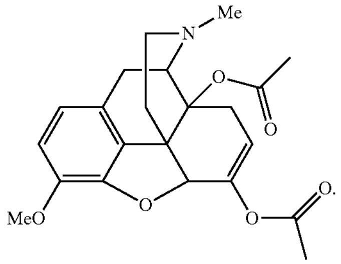 [SMILES: COc1ccc2c3c1OC1C(OC(C)=O)=CCC4(OC(C)=O)C(C2)N(C)CCC314]

Embodiment 18. The compound of Embodiment 6 or 17, or a pharmaceutically acceptable salt or solvate thereof, wherein $R^6$ is methyl.

Embodiment 19. The compound of any one of Embodiments 6 and 14-16, or a pharmaceutically acceptable salt or solvate thereof, wherein $R^6$ is unsubstituted $C_{7-12}$ alkyl.

Embodiment 20. The compound of any one of Embodiments 1-5 and 7-19, or a pharmaceutically acceptable salt or solvate thereof, wherein $R^5$ is unsubstituted $C_{1-6}$ alkyl.

Embodiment 21. The compound of any one of Embodiments 1-5 and 7-19, or a pharmaceutically acceptable salt or solvate thereof, wherein $R^5$ is unsubstituted $C_{7-12}$ alkyl.

Embodiment 22. The compound of any one of Embodiments 1-5 and 7-19, or a pharmaceutically acceptable salt or solvate thereof, wherein $R^5$ is $-CH_2-O-(CH_2CH_2O)_m-CH_3$, wherein m is 1, 2, or 3.

Embodiment 23. The compound of any one of Embodiments 1-3, 6-10, and 14-16, or a pharmaceutically acceptable salt or solvate thereof, wherein $R^6$ is —$CH_2$—O—$(CH_2CH_2O)_m$—$CH_3$, wherein m is 1, 2, or 3.

Embodiment 24. The compound of Embodiment 4, wherein $R^{31}$ is OH.

Embodiment 25. The compound of Embodiment 2, or a pharmaceutically acceptable salt or solvate thereof, wherein $R^1$ is H or unsubstituted $C_{1-6}$ alkyl;

$R^2$ is —C(O)($C_{1-6}$)alkyl;

$R^3$ is H or OH; and $R^4$ is unsubstituted $C_{1-6}$ alkyl, provided that the compound is not

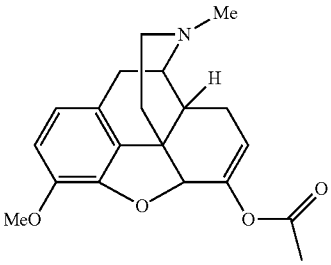

or

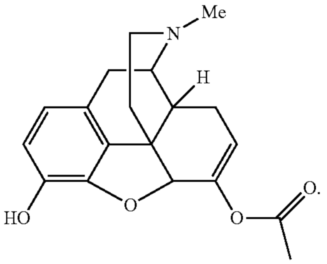

Embodiment 26. The compound of Embodiment 2, which is

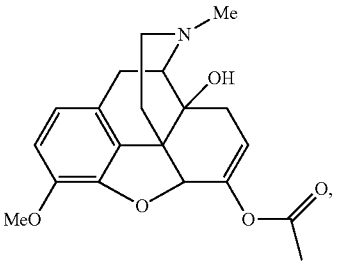 [SMILES: COc1ccc2c3c1OC1C(OC(C)=O)=CCC4(O)C(C2)N(C)CCC314]

or a pharmaceutically acceptable salt or solvate thereof.

Embodiment 27. The compound of Embodiment 26, which is

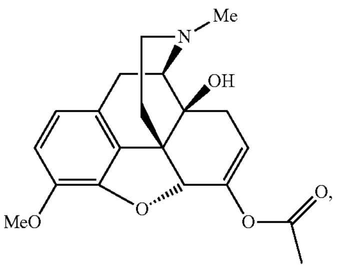

or a pharmaceutically acceptable salt or solvate thereof.

Embodiment 28. The compound of Embodiment 1, which is selected from the group consisting of

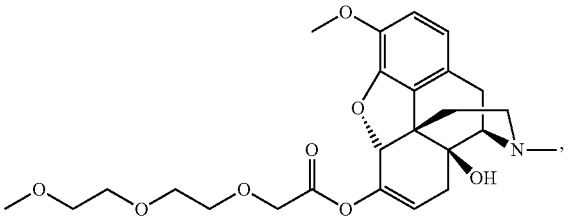

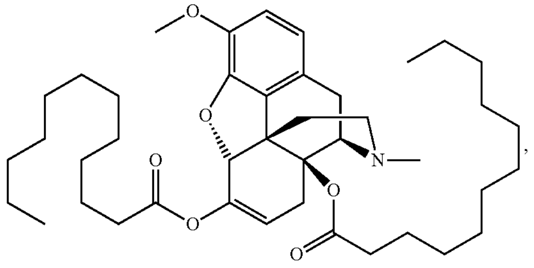

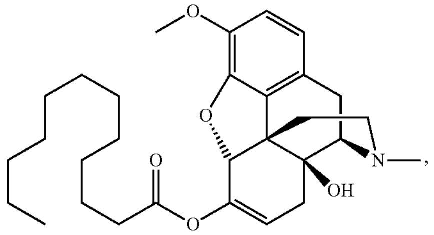

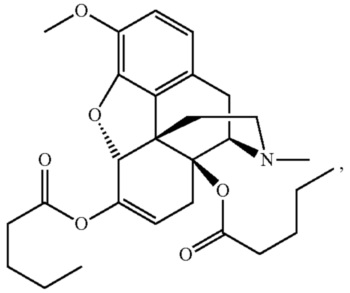

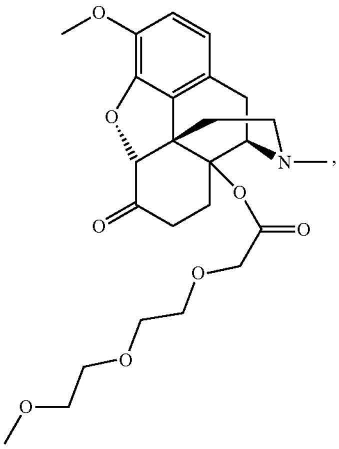

and

-continued

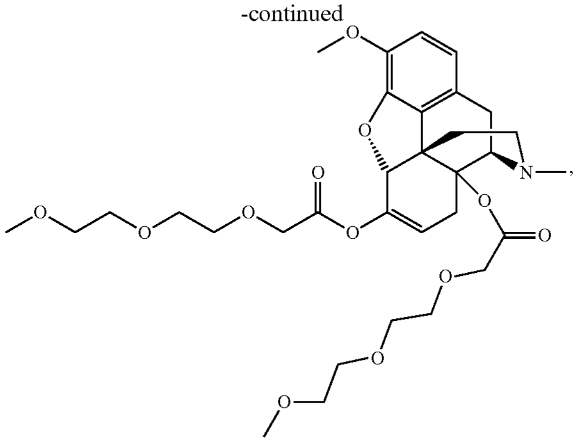

or a pharmaceutically acceptable salt or solvate thereof.

Embodiment 29. A pharmaceutical composition, comprising a compound of any one of Embodiments 1-28, or a pharmaceutically acceptable salt or solvate thereof, and one or more pharmaceutically acceptable carriers.

Embodiment 30. A method of treating or preventing a disorder responsive to the modulation of one or more opioid receptors in a patient, comprising administering to the patient in need of such treatment or prevention an effective amount of a compound of any one of Embodiments 1-28, or a pharmaceutically acceptable salt or solvate thereof.

Embodiment 31. The method of Embodiment 30, wherein the disorder is pain.

Embodiment 32. A method of treating, ameliorating or preventing pain, constipation, diarrhea, withdrawal from alcohol addiction or withdrawal from drug addiction in a patient, comprising administering an effective amount of a compound of any one of Embodiments 1-28, or a pharmaceutically acceptable salt or solvate thereof, to the patient in need of such treatment or prevention.

Embodiment 33. The method of Embodiment 32, wherein the method is for treating pain.

Embodiment 34. The method of Embodiment 33, wherein said pain is acute pain, chronic pain or surgical pain.

Embodiment 35. The method of Embodiment 34, wherein said pain is chronic pain.

Embodiment 36. The method of Embodiment 35, wherein said chronic pain is neuropathic pain, postoperative pain, or inflammatory pain.

Embodiment 37. A pharmaceutical composition, comprising the compound as claimed in of any one of Embodiments 1-28, or a pharmaceutically acceptable salt or solvate, for use in treating a disorder responsive to the modulation of one or more opioid receptors.

Embodiment 38. The compound as claimed in any one of Embodiments 1-28, or a pharmaceutically acceptable salt or solvate thereof, for use in treating a disorder responsive to the modulation of one or more opioid receptors.

Embodiment 39. A method of preparing a pharmaceutical composition, comprising admixing a compound of any one of Embodiments 1-28, or a pharmaceutically acceptable salt or solvate thereof, with a pharmaceutically acceptable carrier.

Embodiment 40. A kit, comprising a container containing an effective amount of the compound of any one of Embodiments 1-28, or a pharmaceutically acceptable salt or solvate thereof, and instructions for therapeutic use.

Embodiment 41. A method of slowing the onset of activity of an opioid in a mammal in need of opioid therapy, comprising orally administering to the mammal a therapeutically effective amount of the compound or a mixture of the compounds according to any one of Embodiments 1-28, or a pharmaceutically acceptable salt or solvate thereof.

Embodiment 42. The method according to Embodiment 41, further comprising co-administering one or more other therapeutic agents.

Embodiment 43. The method according to Embodiment 42, wherein said one or more other therapeutic agents are one or more non-steroidal anti-inflammatory agents.

Embodiment 44. The method according to Embodiment 42, wherein said one or more other therapeutic agents are one or more opioid agonists.

Embodiment 45. The method according to Embodiment 42, wherein said one or more other therapeutic agents are one or more opioid antagonists.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound of Formula IV:

IV

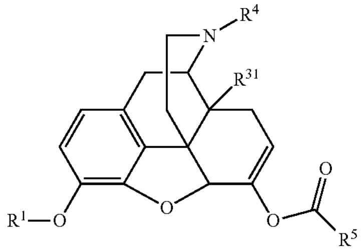

or a pharmaceutically acceptable salt or solvate thereof, wherein:

- $R^1$ is hydrogen; $C_{1-6}$ alkyl optionally substituted with 1, 2, or 3 substituents, each substituent independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;
- $R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each substituent independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl;
- $R^5$ is selected from the group consisting of unsubstituted $C_{1-6}$ alkyl, $—CH_2—O—(CH_2CH_2O)_m—R^7$, $—O—(CH_2CH_2O)_n—R^7$, and $—NH—(CH_2CH_2O)_p—R^7$;

$R^7$ is selected from the group consisting of hydrogen and $C_{1-6}$ alkyl;

$R^{31}$ is hydrogen or hydroxy;

m is an integer between 1 and 9;

n and p are each independently an integer between 1 and 20; and

PEG is one ethylene oxide unit or an oligomer of 2 to about 10 ethylene oxide subunits, provided that the compound is not

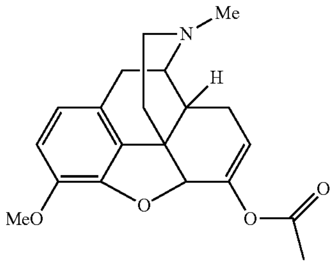

or

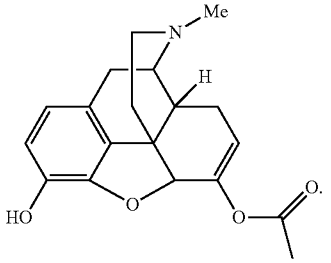

2. The compound of claim 1, which is

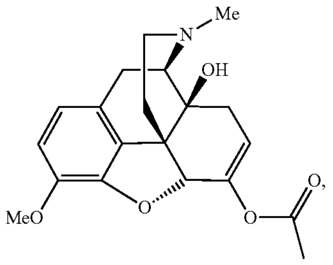

or a pharmaceutically acceptable salt or solvate thereof.

3. The compound of claim 1, which is

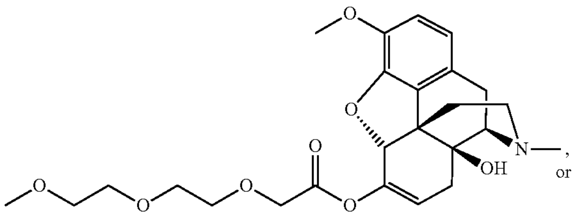

or

-continued

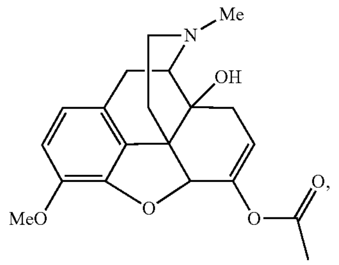

or a pharmaceutically acceptable salt or solvate thereof.

4. A compound of Formula II:

II

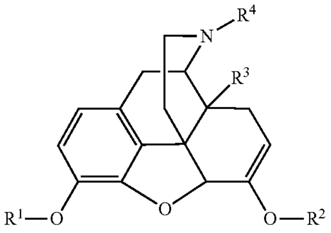

or a pharmaceutically acceptable salt or solvate thereof, wherein:

$R^1$ is hydrogen; $C_{1-6}$ alkyl optionally substituted with 1, 2, or 3 substituents, each substituent independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di(Ci-4) alkylamino, carboxy, $C_{1-4}$ alkoxy, and $C_{1-4}$ alkoxycarbonyl;

$R^2$ is —C(=O)$R^5$ and $R^3$ is —OC(=O)$R^6$, wherein $R^5$ is selected from the group consisting of a straight-chain unsubstituted $C_{7-9}$ alkyl, —$CH_2$—O—$(CH_2CH_2O)_m$—$R^7$, —O—$(CH_2CH_2O)_n$—$R^7$, and —NH—$(CH_2CH_2O)_p$—$R^7$;

$R^6$ is selected from the group consisting of a straight-chain unsubstituted $C_{7-9}$ alkyl, a straight-chain unsubstituted $C_{7-9}$ alkenyl, a straight-chain unsubstituted $C_{7-9}$ alkynyl, —$CH_2$—O—$(CH_2CH_2O)_m$—$R^7$, —O—$(CH_2CH_2O)_n$—$R^7$, and —NH—$(CH_2CH_2O)_p$—$R^7$;

$R^7$ is selected form the group consisting of hydrogen and $C_{1-6}$ alkyl;

m is 2 or 3;

n and p are each independently 2, 3, or 4; and

PEG is one ethylene oxide unit or an oligomer of 2 to about 10 ethylene oxide subunits.

5. The compound of claim 4, which is

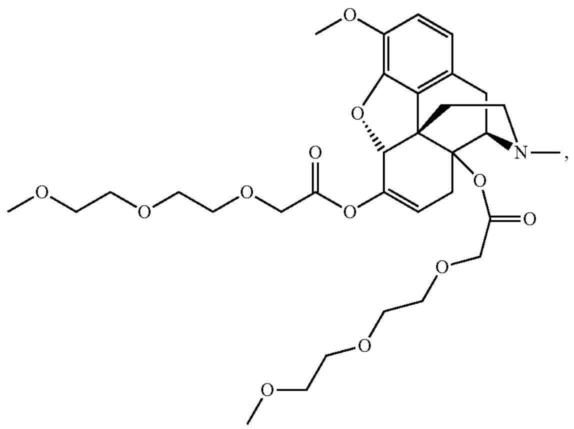

or a pharmaceutically acceptable salt or solvate thereof.

6. A compound of Formula II:

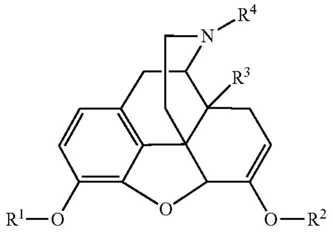

II or a pharmaceutically acceptable salt or solvate thereof, wherein:

$R^1$ is hydrogen; $C_{1-6}$ alkyl optionally substituted with 1, 2, or 3 substituents, each substituent independently selected from the group consisting of hydroxy, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl; or -PEG-$R^7$;

$R^4$ is selected from the group consisting of hydrogen, $C_{1-6}$ alkyl, $C_{2-6}$ alkenyl, $C_{2-6}$ alkynyl, $C_{3-6}$ cycloalkyl, and ($C_{3-6}$ cycloalkyl)($C_{1-4}$)alkyl, any of which is optionally substituted with 1, 2, or 3 substituents, each independently selected from the group consisting of hydroxy, halo, halo($C_{1-4}$)alkyl, amino, $C_{1-4}$ alkylamino, di(Ci-4) alkylamino, carboxy, $C_{1-4}$ alkoxy, and $C_{1-4}$ alkoxycarbonyl;

$R^2$ is —C(═O)$R^5$ and $R^3$ is —OC(═O)$R^6$, wherein $R^5$ is selected from the group consisting of a straight-chain unsubstituted $C_{10-12}$ alkyl, —$CH_2$—O—$(CH_2CH_2O)_m$—$R^7$, —O—$(CH_2CH_2O)_n$—$R^7$, and —NH—$(CH_2CH_2O)_p$—$R^7$;

$R^6$ is selected from the group consisting of a straight-chain unsubstituted $C_{10-12}$ alkyl, a straight-chain unsubstituted $C_{10-12}$ alkenyl, a straight-chain unsubstituted $C_{10-12}$ alkynyl, —$CH_2$—O—$(CH_2CH_2O)_m$—$R^7$, —O—$(CH_2CH_2O)_n$—$R^7$, and —NH—$(CH_2CH_2O)_p$—$R^7$;

$R^7$ is selected form the group consisting of hydrogen and $C_{1-6}$ alkyl;

m is an integer between 4 and 9;

n and p are each independently an integer between 4 and 20; and

PEG is one ethylene oxide unit or an oligomer of 2 to about 10 ethylene oxide subunits.

7. The compound of claim 6, which is

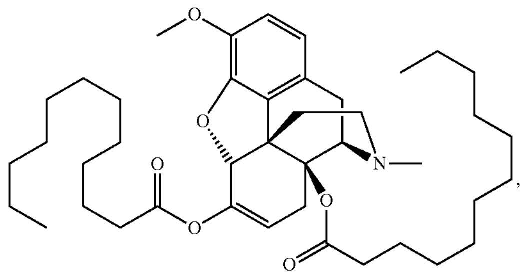

or a pharmaceutically acceptable salt or solvate thereof.

8. A compound, which is

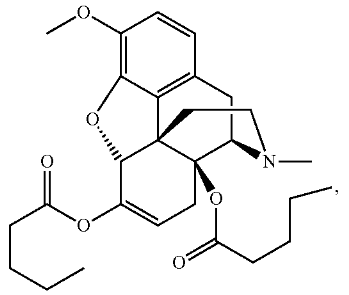

or a pharmaceutically acceptable salt or solvate thereof.

9. A composition, comprising one or more compounds of claim 1, or a pharmaceutically acceptable salt or solvate thereof, and at least one parent opioid.

10. A method of treating or ameliorating pain in a patient, comprising administering an effective amount of a compound of claim 1, or a pharmaceutically acceptable salt or solvate thereof, to the patient in need of such treatment or amelioration.

11. A method of slowing the onset of activity of an opioid in a mammal in need of opioid therapy, comprising orally administering to the mammal a therapeutically effective amount of the compound or a mixture of the compounds according to claim 1, or a pharmaceutically acceptable salt or solvate thereof.

12. A method of slowing the onset of activity of an opioid in a mammal in need of opioid therapy, comprising orally administering to the mammal a therapeutically effective amount of the compound or a mixture of the compounds according to claim 6, or a pharmaceutically acceptable salt or solvate thereof.

13. A method of treating or ameliorating pain in a patient in need thereof, comprising administering an effective amount of a compound of

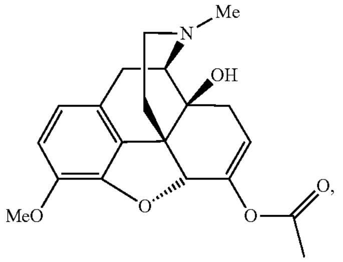

or a pharmaceutically acceptable salt or solvate thereof, to provide the patient a slowed onset of an oxycodone treatment.

14. The method of claim 12, comprising orally administering a compound or a mixture of compounds having Formula V:

V

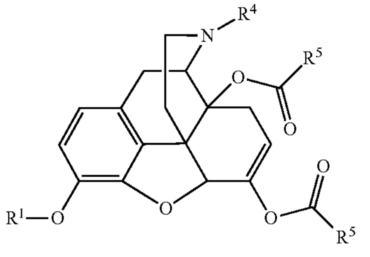

or a pharmaceutically acceptable salt or solvate thereof, wherein $R^1$ is hydrogen H or unsubstituted $C_{1-6}$ alkyl;

$R^4$ is unsubstituted $C_{1-6}$ alkyl; and $R^5$ is decyl, undecyl, or dodecyl.

15. A pharmaceutical composition comprising the compound of claim 1 and one or more pharmaceutically acceptable carriers.

16. The compound of claim 1, or a pharmaceutically acceptable salt or solvate thereof, wherein $R^1$ is hydrogen or unsubstituted $C_{1-6}$ alkyl and $R^4$ is unsubstituted $C_{1-6}$ alkyl.

17. The compound of claim 1, or a pharmaceutically acceptable salt thereof, wherein $R^{31}$ is hydroxy.

18. The compound of claim 1, or a pharmaceutically acceptable salt thereof, wherein $R^5$ is unsubstituted $C_{1-6}$ alkyl.

19. The compound of claim 1, or a pharmaceutically acceptable salt thereof, wherein $R^5$ is selected from the group consisting of $-CH_2-O-(CH_2CH_2O)_m-R^7$, $-O-(CH_2CH_2O)_n-R^7$, and $-NH-(CH_2CH_2O)_p-R^7$;

$R^7$ is hydrogen or $C_{1-4}$ alkyl;

m is 1, 2, 3, 4, or 5;

n and p are each independently selected from the group consisting of 1, 2, 3, 4, 5, 6, 7, 8, 9, and 10.

20. The compound of claim 19, or a pharmaceutically acceptable salt thereof, wherein $R^7$ is hydrogen or methyl.

21. The compound of claim 19, or a pharmaceutically acceptable salt thereof, wherein $R^5$ is $-CH_2-O-(CH_2CH_2O)_m-R^7$.

22. The compound of claim 19, or a pharmaceutically acceptable salt thereof, wherein m is 1, 2, or 3.

23. The compound of claim 4, wherein $R^5$ and $R^6$ are the same, having the Formula V:

V

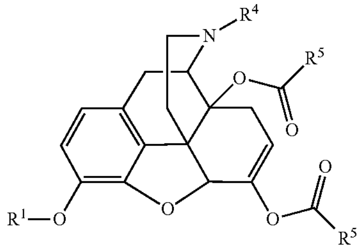

or a pharmaceutically acceptable salt or solvate thereof.

24. The compound of claim 23, or a pharmaceutically acceptable salt or solvate thereof, wherein $R^5$ is $-CH_2-O-(CH_2CH_2O)_m-R^7$, wherein $R^7$ is hydrogen or methyl.

25. The compound of claim 4, or a pharmaceutically acceptable salt or solvate thereof, wherein $R_1$ is hydrogen or unsubstituted $C_{1-6}$ alkyl and $R^4$ is unsubstituted $C_{1-6}$ alkyl.

26. The compound of claim 4, or a pharmaceutically acceptable salt or solvate thereof, wherein $R^1$ and $R^4$ are methyl.

* * * * *